US012173075B2

(12) United States Patent
Sofronova et al.

(10) Patent No.: US 12,173,075 B2
(45) Date of Patent: Dec. 24, 2024

(54) ANTI-IL-5RALPHA MONOCLONAL ANTIBODY

(71) Applicant: JOINT STOCK COMPANY "BIOCAD", St. Petersburg (RU)

(72) Inventors: Ekaterina Vladimirovna Sofronova, g. Kazan' (RU); Aleksei Konstantinovich Misorin, St. Petersburg (RU); Aleksandr Nikolaevich Doronin, Moscow (RU); Timofey Aleksandrovich Nemankin, St. Petersburg (RU); Aleksandra Aleksandrovna Sozonova, g. Severodvinsk (RU); Galina Stepanovna Zhirivskaia, St. Petersburg (RU); Sergey Aleksandrovich Legotsky, Moscow (RU); Anna Konstantinovna Vladimirova, St. Petersburg (RU); Alina Valerevna Beliasnikova, St. Petersburg (RU); Mariia Aleksandrovna Shchemeleva, St. Petersburg (RU); Pavel Andreevich Iakovlev, St. Petersburg (RU); Valery Vladimirovich Solovyev, Pushchino (RU); Elena Andreevna Krendeleva, St. Petersburg (RU); Natalia Evgenevna Pestova, St. Petersburg (RU); Dmitry Valentinovich Morozov, St. Petersburg (RU)

(*) Notice: Subject to any disclaimer, the term of this patent is extended or adjusted under 35 U.S.C. 154(b) by 1121 days.

(21) Appl. No.: 16/753,488

(22) PCT Filed: Oct. 2, 2018

(86) PCT No.: PCT/RU2018/050118
§ 371 (c)(1),
(2) Date: Apr. 3, 2020

(87) PCT Pub. No.: WO2019/070164
PCT Pub. Date: Apr. 11, 2019

(65) Prior Publication Data
US 2020/0291121 A1 Sep. 17, 2020

(30) Foreign Application Priority Data
Oct. 3, 2017 (RU) ................. 2017134413

(51) Int. Cl.
C12N 15/64 (2006.01)
C07K 16/28 (2006.01)
A61K 39/00 (2006.01)
A61K 45/06 (2006.01)

(52) U.S. Cl.
CPC .......... *C07K 16/2866* (2013.01); *C12N 15/64* (2013.01); *A61K 2039/505* (2013.01); *A61K 45/06* (2013.01); *C07K 2317/56* (2013.01)

(58) Field of Classification Search
None
See application file for complete search history.

(56) References Cited

U.S. PATENT DOCUMENTS

| | | |
|---|---|---|
| 4,120,649 A | 10/1978 | Schechter |
| 4,399,216 A | 8/1983 | Axel et al. |
| 4,510,245 A | 4/1985 | Cousens et al. |
| 4,634,665 A | 1/1987 | Axel et al. |
| 4,665,077 A | 5/1987 | Stringfellow et al. |
| 4,676,980 A | 6/1987 | Segal et al. |
| 4,740,461 A | 4/1988 | Kaufman |
| 4,816,567 A | 3/1989 | Cabilly et al. |
| 4,912,040 A | 3/1990 | Kaufman et al. |
| 4,959,455 A | 9/1990 | Clark et al. |
| 4,968,615 A | 11/1990 | Koszinowski et al. |
| 5,114,721 A | 5/1992 | Cohen et al. |
| 5,168,062 A | 12/1992 | Stinski |
| 5,179,017 A | 1/1993 | Axel et al. |
| 5,229,275 A | 7/1993 | Goroff |
| 5,500,362 A | 3/1996 | Robinson et al. |
| 5,545,806 A | 8/1996 | Lonberg et al. |
| 5,545,807 A | 8/1996 | Surani et al. |
| 5,567,610 A | 10/1996 | Borrebaeck et al. |
| 5,569,825 A | 10/1996 | Lonberg et al. |
| 5,571,894 A | 11/1996 | Wells et al. |
| 5,587,458 A | 12/1996 | King et al. |
| 5,591,669 A | 1/1997 | Krimpenfort et al. |
| 5,641,870 A | 6/1997 | Rinderknecht et al. |
| 5,731,168 A | 3/1998 | Carter et al. |
| 5,821,337 A | 10/1998 | Carter et al. |

(Continued)

FOREIGN PATENT DOCUMENTS

| | | |
|---|---|---|
| EP | 0256055 B1 | 8/1991 |
| EP | 0323997 B1 | 4/1993 |

(Continued)

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Kaji et al, (Journal of Experimental Medicine; 2012; vol. 209, pp. 2079-2097).*
Poosarla et al. (2017, Biotechn. Bioeng. 114(6): 1331-1342).*
Rabia, et al. (2018, Biochemical Engineering Journal 137:365-374).*

(Continued)

*Primary Examiner* — Daniel E Kolker
*Assistant Examiner* — James Ryland Melchior
(74) *Attorney, Agent, or Firm* — Anglehart et al.

(57) ABSTRACT

The present disclosure relates to biotechnology and provides antibodies that specifically bind to IL-5Rα. The disclosure also relates to DNA encoding the antibodies, the corresponding expression vectors and methods of production thereof, as well as methods of treatment using the antibodies.

26 Claims, 17 Drawing Sheets

Specification includes a Sequence Listing.

(56) References Cited

U.S. PATENT DOCUMENTS

| | | | |
|---|---|---|---|
| 5,869,046 | A | 2/1999 | Presta et al. |
| 6,517,529 | B1 | 2/2003 | Quinn |
| 9,334,331 | B2 * | 5/2016 | Igawa .................... C07K 16/40 |
| 10,421,807 | B2 * | 9/2019 | Gonzales ................ A61P 11/00 |
| 2005/0226867 | A1 | 10/2005 | Iida et al. |
| 2008/0095765 | A1 | 4/2008 | Ilda et al. |

FOREIGN PATENT DOCUMENTS

| | | |
|---|---|---|
| EP | 0338841 B1 | 3/1995 |
| EP | 0216846 B2 | 4/1995 |
| EP | 0340109 B1 | 5/1997 |
| EP | 1688437 A1 | 8/2006 |
| FR | 2783326 A1 | 3/2000 |
| JP | 2002-525580 A | 8/2002 |
| JP | 2010-527356 A | 8/2010 |
| NO | 90/08187 A1 | 7/1990 |
| RU | 2280255 C2 | 7/2006 |
| WO | 90/11294 A1 | 10/1990 |
| WO | 91/00360 A1 | 1/1991 |
| WO | 91/01133 A1 | 2/1991 |
| WO | 92/00373 A1 | 1/1992 |
| WO | 93/08829 A1 | 5/1993 |
| WO | 93/16185 A2 | 8/1993 |
| WO | 94/04690 A1 | 3/1994 |
| WO | 97/10354 A1 | 3/1997 |
| WO | 97/17852 A1 | 5/1997 |
| WO | 2000/061739 A1 | 10/2000 |
| WO | 2001/060405 A1 | 8/2001 |
| WO | 02/22805 A2 | 3/2002 |
| WO | 2002/031140 A1 | 2/2004 |
| WO | 2005/035583 A1 | 11/2007 |
| WO | 2008/143878 A1 | 11/2008 |
| WO | 2015/058861 A1 | 4/2015 |
| WO | 2015/172800 A1 | 11/2015 |
| WO | 2015/191861 A1 | 12/2015 |
| WO | 2016/194897 A1 | 3/2018 |

OTHER PUBLICATIONS

Brummell et al., Biochemistry; 1993; vol. 32, pp. 1180-1187.*
Kobayashi et al. Protein Engineering; 1999; vol. 12, pp. 879-844.*
Brorson et al. J. Immunol; 1999; vol. 163, pp. 6694-6701.*
Coleman Research in Immunol; 1994; vol. 145; pp. 33-36.*
Rudikoff, et al. (Proc. Natl. Acad. Sci. USA, 79(6):1979-1983, 1982).*
Casset et al; Biochemical and Biophysical Research Communications, 2003; 307:198-205.*
Burks et al. (PNAS; 1997; vol. 94, pp. 412-417).*
Foster, (J. Exp. Med, vol. 183 Jan. 1996 195-201).*
Shi et al, (American Journal of Respiratory and Critical Care Medicine.; 1998, vol. 157, pp. 204-209).*
Khorasanizadeh, (International Reviews of Immunology, 35:294-311, 2016).*
European application No. 18864122.9 extended European search report dated May 27, 2021.
Kolbeck R et al., MEDI-563, MEDI-563, a humanized anti-IL-5 receptor α mAb with enhanced antibody-dependent cell-mediated cytotoxicity function. Journal of Allergy and Clinical Immunology. vol. 125, Issue 6, Jun. 2010, pp. 1344-1353.e2.
Lotvall J. et al., Treating asthma with Anti-IgE or Anti IL-5. Curr Pharm Des. 1999; 5:757-770.
Tetsuya A. et al., The mechanism of IL-5 signal transduction. American Journal of Physiology—Cell Physiology Published Sep. 1, 1998 vol. 275 No. 3, C623-C633.
Shinkawa T.et al. The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity. J Biol Chem 2003, 278(5):3466-3473.

Ward et al., Binding activities of a repertoire of single immunoglobulin variable domains secreted from *Escherichia coli*. (1989) Nature 341:544-546.
Bird et al. Single-Chain Antigen-Binding Proteins. (1988) Science 242:423-426.
Huston et al. Protein engineering of antibody binding sites: recovery of specific activity in an anti-digoxin single-chain Fv analogue produced in *Escherichia coli*. (1988) Proc. Natl. Acad. Sci. USA 85:5879-5883.
Burks et al., In vitro scanning saturation mutagenesis of an antibody binding pocket. Proc Natl Acad Sci USA, 94:412-417 (1997).
Wu et al., Stepwise in vitro affinity maturation of Vitaxin, an αvβ3-specific humanized mAb. Proc Natl Acad Sci USA 95:6037-6042 (1998).
Chen, Y., et al., Selection and analysis of an optimized anti-VEGF antibody: crystal structure of an affinity-matured fab in complex with antigen. (1999) J. Mol. Biol. 293: 865-881.
Magdelaine-Beuzelin et al., Structure-function relationships of the variable domains of monoclonal antibodies approved for cancer treatment. Critical Reviews in Oncology/Hematology. vol. 64, Issue 3, Dec. 2007, pp. 210-225.
Lefranc et al., IMGT unique numbering for immunoglobulin and T cell receptor variable domains and Ig superfamily V-like domains. Developmental & Comparative Immunology. vol. 27, Issue 1, Jan. 2003, pp. 55-77.
Sheets MD, et al. Efficient construction of a large nonimmune phage antibody library: The production of high-affinity human single-chain antibodies to protein antigens. Proc Natl Acad Sci U S A 1998,95:6157-6162.
Hans, et al. A large non-immunized human Fab fragment phage library that permits rapid isolation and kinetic analysis of high affinity antibodies. J Biol Chem 1999,274:18218-18230.
Vaughan TJ et al. Human antibodies with sub-nanomolar affinities isolated from a large non-immunized phage display library. Nat Biotechnol 1996, 14:309-314.
Ulitin AB et al. The library of human miniantibodies in the phage display format: Designing and testing DAN: Izd-vo "Nauka"; 2005.
Marks et al., By-passing immunization: Human antibodies from V-gene libraries displayed on phage. J. Mol. Biol., 222:581-597 (1991).
Smith GP, Filamentous fusion phage: novel expression vectors that display cloned antigens on the virion surface. Science 1985, 228:1315-1317.
Lonberg N, et al.: Antigen-specific human antibodies from mice comprising four distinct genetic modifications. Nature 1994, 368:856-859.
Ravetch and Kinet, Fc Receptors. Annual Review of Immunology. vol. 9:457-492 (Volume publication date Apr. 1991).
Clynes et al. Fc receptors are required in passive and active immunity to melanoma. PNAS (USA) 95: 652-656 (1998).
Daëron, Annu. Fc Receptor Biology. Annual Review of Immunology. vol. 15:203-234 (Volume publication date Apr. 1997).
Gazzano-Santoro et al., A non-radioactive complement-dependent cytotoxicity assay for anti-CD20 monoclonal antibody. Journal of Immunological Methods vol. 202, Issue 2, Mar. 28, 1997, pp. 163-171.
Kohler, et al. Continuous cultures of fused cells secreting antibody of predefined specificity. Nature 256, 1975, p. 495-497.
Munson et al., LIGAND : A Versatile Computerized Approach for Characterization of Ligand-Binding Systems. Analytical Biochemstry, 107:220-239 (1980).
McCafferty et al., Phage antibodies: filamentous phage displaying antibody variable domains. Nature, 348:552-554 (1990).
Clackson et al., Making antibody fragments using phage display libraries. Nature, 352:624-628 (1991).
Marks et al., By-passing immunization: Building High Affinity Human Antibodies by Chain Shuffling. Bio/Technology, 10:779-783 (1992).
Waterhouse et al., Combinatorial infection and in vivo recombination: a strategy for making large phage antibody repertoires. Nucl. Acids. Res. 21:2265-2266 (1993).

(56) References Cited

OTHER PUBLICATIONS

Morrison, et al., Chimeric human antibody molecules: mouse antigen-binding domains with human constant region domains. Proc. Natl. Acad. Sci. USA: 81:6851 (1984).
Jones et al., Replacing the complementarity-determining regions in a human antibody with those from a mouse. Nature, 321:522-525 (1986).
Carter et al., Humanization of an anti-p185HER2 antibody for human cancer therapy. Proc. Natl. Acad. Sci. USA: 89:4285 (1992).
Carter et al., High Level *Escherichia coli* Expression and Production of a Bivalent Humanized Antibody Fragment. Bio/ Technology 10:163-167 (1992).
Suresh et al., [17] Bispecific monoclonal antibodies from hybrid hybridomas. Methods in Enzymology 121:210 (1986).
Brennan et al., Preparation of Bispecific Antibodies by Chemical Recombination of Monoclonal Immunoglobulin G1 Fragments. Science 229:81 (1985).
Kostelny et al, Formation of a bispecific antibody by the use of leucine zippers. J. Immunol. 148(5):1547-1553 (1992).
Hollinger et al., "Diabodies": Small bivalent and bispecific antibody fragments. Proc. Natl. Acad. Sci. USA 90:6444-6448 (1993).
Offner et al, T Cell Receptor Peptide Therapy Triggers Autoregulation of Experimental Encephalomyelitis. Science 251:430-432 (1991).
Edelman, G.M., et al., The Covalent Structure of an Entire yG Immunoglobulin Molecule. Proc. Natl. Acad. Sci. Natl. Acad. Sci. USA 63 (1969) 78-85.
Sachdev S.Sidhu et al., [21] Phage display for selection of novel binding peptides. Methods in Enzymology. vol. 328, 2000, pp. 333-363, IN5.
Tristan J. Vaughan et al., Human Antibodies with Sub-nanomolar Affinities Isolated from a Large Non-immunized Phage Display Library. Nat Biotechnol. Mar. 1996;14(3):309-314.
BissanAl-Lazikani et al. Standard conformations for the canonical structures of immunoglobulins. Journal of Molecular Biology. vol. 273, Issue 4, Nov. 7, 1997, pp. 927-948.
Kozbor, A human hybrid myeloma for production of human monoclonal antibodies. J Immunol Dec. 1, 1984, 133(6) 3001-3005 (Abstract).
Sims et al., A humanized CD18 antibody can block function without cell destruction. J. Immunol. 151:2296 (1993) (Abstract).
Gruber et al., Efficient tumor cell lysis mediated by a bispecific single chain antibody expressed in *Escherichia coli*. J. Immunol., 152:5368-5374 (1994) (Abstract).
Koike M. et.al. Establishment of humanized anti-interleukin-5 receptor alpha chain monoclonal antibodies having a potent neutralizing activity. Hum Antibodies 2009, 18(1-2):17-27(Abstract).
International application No. PCT/RU2018/050118 International Search Report dated Feb. 14, 2019.
International application No. PCT/RU2018/050118 Translation of the ISR dated Feb. 14, 2019.
International application No. PCT/RU2018/050118 Written Opinion of the International Searching Authority dated Feb. 14, 2019.
International application No. PCT/RU2018/050118 English Translation of the Written Opinion of the International Searching Authority dated Feb. 14, 2019.
Corresponding Japanese patent application No. 2020-0519415 Notice of Reasons for Refusal dated Aug. 16, 2022 (Translation provided).
Corresponding Japanese patent application No. 2020-0519415 Search report dated Aug. 24, 2022 (Translation provided).
*Office action regarding—Corresponding European patent application No. 18864122.9 dated May 11, 2023.

* cited by examiner

ANTI-IL-5RALPHA MONOCLONAL ANTIBODY

FIELD OF INVENTION

The present invention relates to biotechnology, in particular to antibodies or antigen-binding fragments thereof, and to use thereof. More specifically, the present invention relates to monoclonal antibodies that specifically bind to IL-5Rα (interleukin 5 receptor α-chain). The invention also relates to a nucleic acid encoding said antibody or antigen-binding fragment thereof, an expression vector, a method for preparing said antibody, and use of said antibody in treatment of diseases or disorders associated with IL-5Rα.

BACKGROUND OF THE INVENTION

Interleukin 5 (IL-5), a proinflammatory cytokine, the granulocyte-macrophage colony-stimulating factor group, which is a four-helix protein. Interleukin 5 is generally produced by Th2 cells and mast cells. IL-5 stimulates the proliferation and differentiation of activated B-lymphocytes, induces a switch of the synthesis of immunoglobulins to IgA. Many functions of eosinophils and basophils are mediated by the action of interleukin-5 (IL-5). It is known that IL-5 promotes the differentiation and activation of eosinophils, and also increases viability thereof by inhibiting apoptosis [Lotvall J., Pullertis T. Treating asthma with Anti-IgE or Anti IL-5. Curr Pharm Des. 1999; 5:757-70 and Kolbeck R., Kozhich A., Koike M. et al. Medi-563, a humanized anti-IL-5 receptor alpha mAb with enhanced antibody-dependent cell mediated cytotoxicity function. J Allergy Clin Immunol. 2010; 125(1):1344-53].

IL-5 acts through a specific receptor (IL-5R) expressed on human eosinophil/basophil precursors and on mature eosinophils/basophils. IL-5R consists of a unique α-chain (IL-5Ra/CD125, extracellular domain) and IL-3/GM-CSF receptor common β-chain (bc/CD131), which itself does not bind a ligand, but increases the affinity of IL-5 to the homonymous receptor and is directly involved in signal transduction [Tetsuya A., Rafeul A. The mechanism of IL-5 signal transduction American Journal of Physiology—Cell Physiology Published 1 Sep. 1998 Vol. 275 no. 3, C623-C633].

Development of eosinophilia is associated with selective expression of IL-5R on early bone marrow eosinophil precursor cells. Thus, inhibiting the interaction between IL-5 and the cellular receptor thereof seems to be most preferred for suppressing eosinophilia.

The therapeutic significance of eosinophilia suppression is due to the high levels of eosinophil granulocytes in a number of pathological processes. Thus, an increase in eosinophil count in the respiratory tract in patients with bronchial asthma, and in the esophageal epithelium in patients with eosinophilic esophagitis underlies the pathophysiology of said diseases. Eosinophils release proinflammatory mediators, such as eosinophil cationic protein (ECP) and leukotrienes.

A monoclonal antibody benralisumab is known from the prior art, which binds IL-5Rα and thereby inhibits the interaction of the receptor with a ligand. Said monoclonal antibody significantly depletes eosinophils in blood and lungs tissue. Benralizumab is a humanized monoclonal antibody (IgG1/k) derived from a murine antibody produced using hybridoma technology [Koike M., Nakamura K. et. al. Establishment of humanized anti-interleukin-5 receptor alpha chain monoclonal antibodies having a potent neutralizing activity. Hum Antibodies 2009, 18(1-2):17-27]. Said antibody binds with high affinity (KD=11 pm) to IL-5Rα and inhibits IL-5 dependent cell proliferation (IC50=0.3 nm) [Kolbeck R., Kozhich A et. al. MEDI-563, a humanized anti-interleukin 5 receptor-alpha monoclonal antibody, with enhanced antibody-dependent cell-mediated cytotoxicity function. J Allergy Clin Immunol 2010, 125(6): 1344-53.e2]. Benralizumab is produced in an afucosylated cell line, and the absence of fucose in the olicosaccharide nucleus achieved doing so results in a 5-10 fold improvement in binding to soluble human FcγRIIIa, and thereby increases antibody-dependent cellular cytotoxicity [Shinkawa T., Nakamura K. et al. The absence of fucose but not the presence of galactose or bisecting N-acetylglucosamine of human IgG1 complex-type oligosaccharides shows the critical role of enhancing antibody-dependent cellular cytotoxicity. J Biol Chem 2003, 278(5):3466-73]. Said antibody is in phase 3 clinical trials. Antibody benralizumab has been described in international application WO9710354 (A1).

A bispecific antibody that binds to IL-5R and to human CD3e (ND003) is also known in the prior art. Said antibody is at the preclinical research stage and is described in international applications WO2015172800 and WO2015058861.

It follows from the above that the creation of new antibodies that effectively bind to IL-5Rα and inhibit IL-5Rα-mediated activation is important.

We have developed a fully human monoclonal antibody mAb (BCD-133), which binds human IL-5Rα with an affinity comparable to that of benralisumab and inhibits IL-5Rα-mediated activation. As is the case with benralizumab, BCD-133 has enhanced antibody-dependent cytotoxicity, thus allowing activating an immune response to cells bearing the IL-5 receptor. Antibody BCD-133 selectively binds to IL-5Rα and is an effective inhibitor of IL-5Rα-mediated activation of immune competent cells and the associated specific inflammation. A cell test shows antibody BCD-133 activity that exceeds the action of benralizumab. Furthermore, BCD-133 is a fully human antibody obtained de novo; this fact allows to reduce immunogenicity risk and does not require further genetic transformations directed to increase in affinity to a human protein, which can lead to loss of binding affinity.

BRIEF SUMMARY OF INVENTION

The present invention relates to binding molecules, for example, antibodies directed to binding to IL-5Rα. Such antibodies can be used to treat a disease or disorder mediated by the interaction of IL-5 and cellular receptor thereof.

In one aspect, the present invention relates to a monoclonal antibody or antigen-binding fragment thereof that specifically binds to IL-5Rα and comprise a heavy chain variable domain comprising an amino acid sequence that is at least 80% homologous to the sequence of SEQ ID NO: 3 and a light chain variable domain comprising an amino acid sequence that is at least 80% homologous to the sequence of SEQ ID NO: 8, i.e. the amino acid sequences of SEQ ID NOs: 3 and 8 may comprise 1 or 2 amino acid amino acid substitutions.

In one embodiment, a monoclonal antibody or antigen-binding fragment thereof comprises a heavy chain variable domain comprising the amino acid sequence of SEQ ID NO: 3.

In one embodiment, a monoclonal antibody or antigen-binding fragment thereof contains a light chain variable domain comprising the amino acid sequence of SEQ ID NO: 8.

In one embodiment, a monoclonal antibody or antigen-binding fragment thereof comprises a heavy chain variable domain comprising amino acid sequences that are at least 80% homologous to the sequences of SEQ ID NOs: 1-3, i.e. the amino acid sequences of SEQ ID NOs: 1-3 may comprise 1 or 2 amino acid amino acid substitutions.

In one embodiment, a monoclonal antibody or antigen-binding fragment thereof comprises a heavy chain variable domain comprising the amino acid sequences represented by SEQ ID NOs: 1-3.

In one embodiment, a monoclonal antibody or antigen-binding fragment thereof comprise a light chain variable domain comprising amino acid sequences that are at least 80% homologous to the sequences of SEQ ID NOs: 6-8, i.e. the amino acid sequences of SEQ ID NOs: 6-8 may comprise 1 or 2 amino acid substitutions.

In one embodiment, a monoclonal antibody or antigen-binding fragment thereof comprises a light chain variable domain comprising the amino acid sequences represented by SEQ ID NOs: 6-8.

In one embodiment, a monoclonal antibody or antigen-binding fragment thereof comprises a heavy chain variable domain comprising amino acid sequences that are at least 80% homologous to the sequences of SEQ ID NOs: 1-3, and a light chain variable domain comprising amino acid sequences that are at least 80% homologous to the sequences of SEQ ID NOs: 6-8, i.e. the amino acid sequences of SEQ ID NOs: 1-3 and 6-8 may comprise 1 or 2 amino acid substitutions.

In one embodiment, a monoclonal antibody or antigen-binding fragment thereof comprises a heavy chain variable domain comprising the amino acid sequences of SEQ ID NOs: 1-3, and a light chain variable domain comprising the amino acid sequences of SEQ ID NOs: 6-8.

In one embodiment, a monoclonal antibody or antigen-binding fragment thereof comprises a heavy chain variable domain comprising an amino acid sequence that is at least 90% homologous to an amino acid sequence selected from the group comprising SEQ ID NOs: 4-5.

In one embodiment, a monoclonal antibody or antigen-binding fragment thereof comprises a heavy chain variable domain comprising an amino acid sequence selected from the group comprising SEQ ID NOs: 4-5.

In one embodiment, a monoclonal antibody or antigen-binding fragment thereof comprises a light chain variable domain comprising amino acid sequence that is at least 90% homologous to an amino acid sequence selected from the group comprising SEQ ID NOs: 9-10.

In one embodiment, a monoclonal antibody or antigen-binding fragment thereof comprises a light chain variable domain comprising an amino acid sequence selected from the group comprising SEQ ID NOs: 9-10.

In one embodiment, a monoclonal antibody or antigen-binding fragment thereof comprises a heavy chain variable domain comprising an amino acid sequence that is at least 90% homologous to an amino acid sequence selected from the group comprising SEQ ID NOs: 4-5, and a light chain variable domain comprising an amino acid sequence that is at least 90% homologous to an amino acid sequence selected from the group comprising SEQ ID NOs: 9-10.

In one embodiment, a monoclonal antibody or antigen-binding fragment thereof comprises a heavy chain variable domain comprising an amino acid sequence selected from the group comprising SEQ ID NOs: 4-5, and a light chain variable domain comprising an amino acid sequence selected from the group comprising SEQ ID NOs: 9-10.

In one embodiment, a monoclonal antibody or antigen-binding fragment thereof comprises a heavy chain comprising an amino acid sequence that is at least 90% homologous to an amino acid sequence selected from the group comprising SEQ ID NOs: 11-12, and a light chain comprising an amino acid sequence that is at least 90% homologous to an amino acid sequence selected from the group comprising SEQ ID NOs: 13-14.

In one embodiment, a monoclonal antibody or antigen-binding fragment thereof comprises a heavy chain comprising an amino acid sequence selected from the group comprising SEQ ID NOs: 11-12, and a light chain comprising an amino acid sequence selected from the group comprising SEQ ID NOs: 13-14.

In one embodiment, an IL-5Rα-specific antibody is a full length IgG antibody.

In one embodiment, the IL-5Rα-specific full length IgG monoclonal antibody is of human IgG1, IgG2, IgG3 or IgG4 isotype.

In one embodiment, the IL-5Rα-specific full length IgG monoclonal antibody is of human IgG1 isotype.

In one aspect, the present invention relates to a nucleic acid that encodes said antibody or antigen-binding fragment thereof.

In one embodiment, a nucleic acid is DNA.

In one embodiment, a nucleic acid comprises a nucleotide sequence encoding the heavy chain of an antibody and being at least 90% homologous to a sequence selected from the group comprising SEQ ID NOs: 15-16, and/or a nucleotide sequence encoding the light chain of an antibody and being at least 90% homologous to a sequence selected from the group comprising SEQ ID NOs: 17-18.

In one embodiment, a nucleic acid comprises a nucleotide sequence encoding the heavy chain of antibodies, said heavy chain being selected from the group comprising SEQ ID NOs: 15-16, and/or a nucleotide sequence selected from the group comprising SEQ ID NOs: 17-18, encoding the light chain of an antibody.

In one aspect, the present invention relates to an expression vector that comprises said nucleic acid.

In one aspect, the present invention relates to a method for producing a host cell that is used to produce said antibody or antigen-binding fragment thereof, which comprises transformation of a cell with said vector.

In one aspect, the present invention relates to a host cell that is used for preparing said antibody or antigen-binding fragment thereof, and comprises said nucleic acid.

In one aspect, the present invention relates to a method for producing said antibody or antigen-binding fragment thereof and comprises culturing said host cell in a growth medium under conditions sufficient to produce said antibody, if necessary, followed by isolation and purification of the obtained antibody.

In one aspect, the present invention relates to a pharmaceutical composition used for preventing or treating a disease or disorder mediated by IL-5Rα, which comprises said antibody or antigen-binding fragment thereof, in combination with one or more pharmaceutically acceptable excipients.

In one embodiment, a pharmaceutical composition is intended to be used for preventing or treating a disease or disorder mediated by IL-5Rα, said disease or disorder being selected from asthma, for example, eosinophilic asthma (atopic asthma), for example, severe eosinophilic asthma (atopic asthma); COPD (chronic obstructive pulmonary disease); Churg-Strauss syndrome; eosinophilic esophagitis; eosinophilic gastroenteritis.

In one aspect, the present invention relates to a pharmaceutical combination intended to be used for preventing or treating a disease or disorder mediated by IL-5Rα, said pharmaceutical combination comprising said antibody or antigen-binding fragment thereof and at least one different therapeutically active compound.

In one embodiment, a pharmaceutical combination is intended to be used for preventing or treating a disease or disorder mediated by IL-5Rα, said disease or disorder being selected from asthma, for example, eosinophilic asthma (atopic asthma), for example, severe eosinophilic asthma (atopic asthma); COPD (chronic obstructive pulmonary disease); Churg-Strauss syndrome; eosinophilic esophagitis; eosinophilic gastroenteritis.

In one embodiment, a pharmaceutical combination comprises a therapeutically active compound being selected from a small molecule, antibody or steroid hormones, such as corticosteroids.

In one aspect, the present invention relates to a method for inhibiting the biological activity of IL-5Rα in a subject in need of such inhibition, which comprises administering an effective amount of said antibody or antigen-binding fragment thereof.

In one aspect, the present invention relates to a method for treatment of a disease or disorder mediated by IL-5Rα, which comprises administering in a subject in need of such treatment said antibody or antigen-binding fragment thereof or said pharmaceutical composition, in a therapeutically effective amount.

In one embodiment, the disease or disorder is selected from asthma, for example, eosinophilic asthma (atopic asthma), for example, severe eosinophilic asthma (atopic asthma); COPD (chronic obstructive pulmonary disease); Churg-Strauss syndrome; eosinophilic esophagitis; eosinophilic gastroenteritis, hypereosinophilic syndrome.

In one aspect, the present invention relates to the use of said antibody or antigen-binding fragment thereof or said pharmaceutical composition for treatment of a subject in need of such treatment, of a disease or disorder mediated by IL-5Rα.

In one embodiment, the disease or disorder is selected from asthma, for example, eosinophilic asthma (atopic asthma), for example, severe eosinophilic asthma (atopic asthma); COPD (chronic obstructive pulmonary disease); Churg-Strauss syndrome; eosinophilic esophagitis; eosinophilic gastroenteritis, hypereosinophilic syndrome.

DISCLOSURE OF THE INVENTION

Definitions and General Methods

Figure 1:
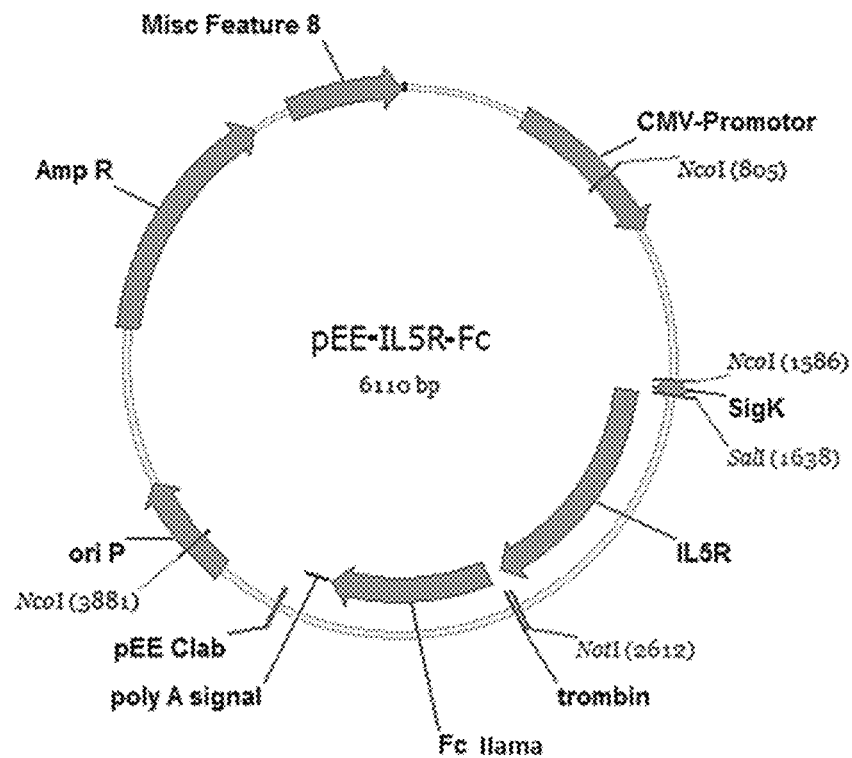
FIG. 1. Plasmid map for transient generation of antigens with Fc fusion protein.
Figure 2:
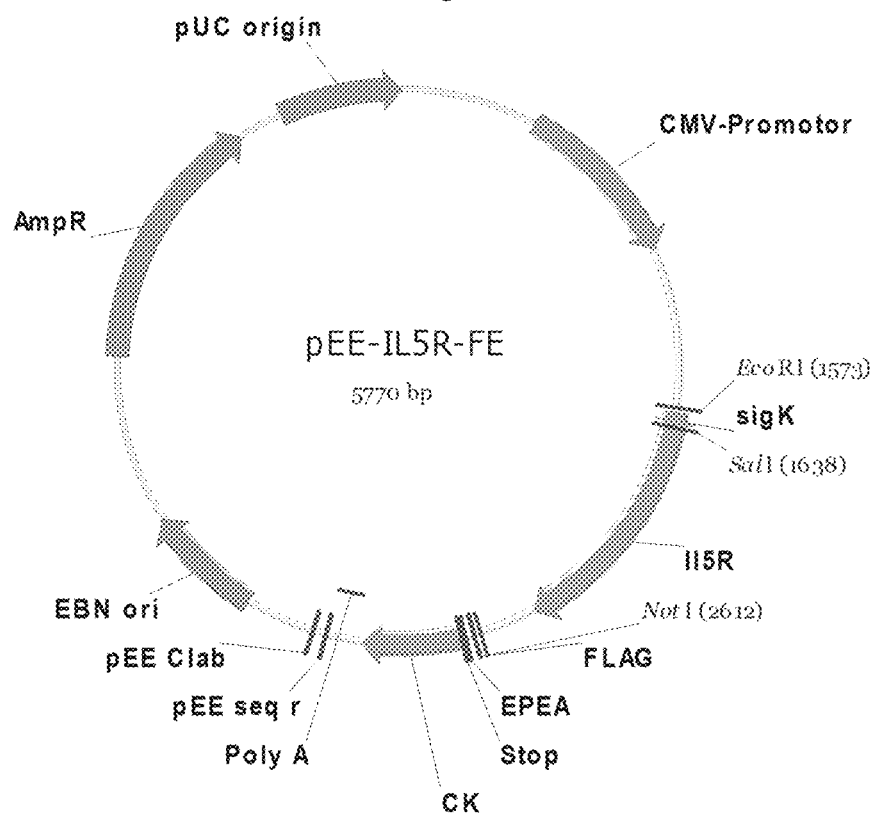
FIG. 2. Plasmid map for transient generation of antigens with C-terminal tag EPE A (FE).

Unless defined otherwise, all technical and scientific terms used herein have the same meaning as is commonly understood by one of ordinary skill in the art.

Further, unless otherwise required by context, singular terms shall include pluralities and plural terms shall include the singular. Typically, the classification and methods of cell culture, molecular biology, immunology, microbiology, genetics, analytical chemistry, organic synthesis chemistry, medical and pharmaceutical chemistry, as well as hybridization and chemistry of protein and nucleic acids described herein are well known and widely used by those skilled in the art. Enzyme reactions and purification methods are performed according to the manufacturer's instructions, as is common in the art, or as described herein.

Definitions Related to Antibody

The term IL-5R or "interleukin 5 receptor", as used herein, is a protein which binds interleukin 5 (IL-5). Interleukin-5 receptor (IL-5R) expression is mainly observed only on the surface of eosinophils, basophils and mast cells. IL-5R consists of a unique α-chain (IL-5Ra/CD125, extracellular domain) and shared with IL-3 and GM-CSF receptors β-chain (bc/CD131), which itself does not bind a ligand, but increases the affinity of IL-5 to the homonymous receptor and is directly involved in signal transduction.

Amplification of this gene and/or hyperexpression of protein thereof has been found in many autoimmune diseases, including asthma, for example, eosinophilic asthma (atopic asthma), for example, severe eosinophilic asthma (atopic asthma); COPD (chronic obstructive pulmonary disease); Churg-Strauss syndrome; eosinophilic esophagitis; eosinophilic gastroenteritis or hypereosinophilic syndrome.

The term "binding molecule" includes antibodies and immunoglobulins.

The term "antibody" or "immunoglobulin" (Ig) as used herein includes whole antibodies and any antigen binding fragment (i.e., "antigen-binding portion") or single chains. The term "antibody" refers to a glycoprotein comprising at least two heavy (H) chains and two light (L) chains interconnected by disulfide bonds, or an antigen-binding portion. Each heavy chain comprises a heavy chain variable region (abbreviated referred to herein as VH) and a heavy chain constant region. Known are five types of mammalian Ig heavy chain denoted by Greek letters: α, δ, ε, γ and μ. The type of a heavy chain present defines the class of an antibody; these chains are found in IgA, IgD, IgE, IgG, and IgM antibodies, respectively. Distinct heavy chains differ in size and composition; α and γ contain approximately 450 amino acids, while μ and ε have approximately 550 amino acids. Each heavy chain has two regions, the constant region and the variable region. The constant region is identical in all antibodies of the same isotype, but differs in antibodies of different isotypes. Heavy chains γ, α and δ have a constant region composed of three constant domains CH1, CH2 and CH3 (in a line), and a hinge region for added flexibility (Woof J., Burton D., Nat Rev Immunol 4, 2004, cc. 89-99); heavy chains μ and ε have a constant region composed of four constant domains CH1, CH2, CH3 and CH4. In mammals, known are only two types of light chain denoted by lambda (λ) and kappa (κ). Each light chain consists of a light chain variable region (abbreviated referred to herein as VL) and light chain constant region. The approximate length of a light chain is 211 to 217 amino acids. Preferably the light chain is a kappa (κ) light chain, and the constant domain CL is preferably C kappa (κ).

"Antibodies" according to the invention can be of any class (e.g., IgA, IgD, IgE, IgG, and IgM, preferably IgG), or subclass (e.g., IgG1, IgG2, IgG3, IgG4, IgA1 and IgA2, preferably IgG1).

VL and VH regions can be further subdivided into hypervariability regions called complementarity determining regions (CDRs), interspersed between regions that are more conserved, termed framework regions (FR). Each VH and VL is composed of three CDR and four FR, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody or "antigen-binding fragment" (or simply "antibody portion" or "antibody fragment"), as used herein, refers to one or more fragments of an antibody that retain the ability to specifically bind to an antigen. It has been shown that the antigen-binding function of an antibody can be performed by fragments of a full length antibody Examples of binding fragments which are included within the term "antigen-binding portion" of an antibody include (i) Fab-fragment monovalent fragment consisting of the VL, VH, CL and CH1 domains; (ii) F(ab') 2 fragment, a bivalent fragment comprising two Fab-fragments linked by a disulfide bridge at the hinge region; (iii) Fd-fragment consisting of the VH and CH1 domains; (iv) Fv-fragment consisting of the VL and VH domains of a single arm of an antibody; (v) dAb-fragment (Ward et al., (1989) Nature 341:544-546), which consists of a VH/VHH domain; and (vi) extracted complementarity determining region (CDR). In addition, two regions of the Fv-fragment, VL and VH, are encoded by separate genes, they can be joined using recombinant methods using a synthetic linker that enables them to receive a single protein chain in which the VL and VH region are paired to form monovalent molecules (known as single chain Fv (scFv); see e.g., Bird et al. (1988) Science 242: 423-426; H Huston et al. (1988) Proc. Natl. Acad. Sci. USA 85:5879-5883). It is assumed that such single-stranded molecules are also included within the term "antigen-binding portion" of an antibody. These antibody fragments are obtained using conventional techniques known to those skilled in the art, and the fragments are screened in the same manner as are intact antibodies.

Preferably, the CDR of antigen-binding portion or the whole antibody antigen binding portion of the invention is derived from mouse, lama or human donor library or substantially of human origin with certain amino acid residues altered, e.g., substituted with different amino acid residues in order to optimize the properties of the specific antibodies, e.g., KD, koff, IC50, EC50, ED50. Preferably the framework regions of antibodies of the invention are of human origin or substantially of human origin (at least 80, 85, 90, 95, 96, 97, 98 or 99% of human origin).

In other embodiments, the antigen binding portion of the invention may be derived from other non-human species including mouse, lama, rabbit, rat or hamster, but not limited to. Alternatively, the antigen-binding region can be derived from the human species.

The term "variable domain" refers to the fact that certain portions of the variable domains greatly differ in sequence among antibodies. The V domain mediates antigen binding and determines specificity of each particular antibody for its particular antigen. However, the variability is not evenly distributed across the 110-amino acid span of the variable domains. Instead, the V regions consist of invariant fragments called framework regions (FRs) of 15-30 amino acids separated by shorter regions of extreme variability called "hypervariable regions" or CDR. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies. The constant domains are not involved directly in binding an antibody to an antigen, but exhibit various effector functions, such as participation of the antibody in antibody-dependent cellular cytotoxicity (ADCC).

The term "hypervariable region" as used herein refers to the amino acid residues of an antibody which are responsible for antigen binding. The hypervariable region generally comprises amino acid residues from a "complementarity determining region" or "CDR" and/or those residues from a "hypervariable loop".

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., Proc Natl Acad Sci USA, 94:412-417 (1997) and the stepwise in vitro affinity maturation method by Wu et al., Proc Natl Acad Sci USA 95:6037 6042 (1998).

"Framework regions" (FR) are those variable domain residues other than the CDR residues. Each variable domain typically has four FRs identified as FR1, FR2, FR3 and FR4. If the CDRs are defined according to Kabat, the light chain FR residues are positioned about at residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

An antibody of the present invention "which binds" a target antigen refers to an antibody capable of binding the antigen with sufficient affinity such that the antibody can be used as a diagnostic and/or therapeutic agent targeting a protein or cell expressing said antigen, and slightly cross-reacts with other proteins. According to analytical methods: fluorescence-activated cell sorting (FACS), radioimmunoassay (RIA) or ELISA, in such embodiments, the degree of antibody binding to a non-target protein is less than 10% of antibody binding to a specific target protein. With regard to the binding of an antibody to a target molecule, the term "specific binding" or "specifically binds to" or is "specific for" a particular polypeptide or an epitope on a particular polypeptide target means binding that is noticeably (measurably) different from a non-specific interaction (for example, in the case of bH1-44 or bH1-81, a non-specific interaction is binding to bovine serum albumin, casein, fetal bovine serum or neutravidin).

Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. As used herein, the term "specific binding" or "specifically binds to" or is "specific for" a particular polypeptide or an epitope on a particular polypeptide target can be described by a molecule having a Kd for the target of at least about 200 nM, or at least about 150 nM, or at least about 100 nM, or at least about 60 nM, or at least about 50 nM, or at least about 40 nM, or at least about 30 nM, or at least about 20 nM, or at least about 10 nM, or at least about 8 nM, or at least about 6 nM, or at least about 4 nM, or at least about 2 nM, or at least about 1 nM, or greater. In one embodiment, the term "specific binding" refers to binding where a molecule binds to a particular polypeptide or epitope on a particular polypeptide without substantially binding to any other polypeptide or polypeptide epitope.

The term "Ka" as used herein is intended to refer to the association rate of a particular antibody-antigen interaction, whereas the term "Kd" is intended to refer to the dissociation rate of a particular antibody-antigen interaction.

"Binding affinity" generally refers to the strength of the sum total of noncovalent interactions between a single binding site of a molecule (e.g., an antibody) and its binding partner (e.g., an antigen). Unless indicated otherwise, "binding affinity" refers to intrinsic (characteristic, true) binding affinity which reflects a 1:1 interaction between members of a binding pair (e.g., antibody and antigen). The affinity of a molecule X for its binding partner Y can generally be represented by the dissociation constant (Kd). The preferred Kd value is about 200 nM, 150 nM, 100 nM, 60 nM, 50 nM, 40 nM, 30 nM, 20 nM, 10 nM, 8 nM, 6 nM, 4 nM, 2 nM, 1 nM, or less. Affinity can be measured by common methods known in the art, including those described herein. Low-affinity antibodies generally bind an antigen slowly and tend to dissociate readily, whereas high-affinity antibodies generally bind an antigen faster and tend to remain bound longer. A variety of methods of measuring binding affinity are known in the art, any of which can be used for purposes of the present invention.

In one embodiment, "Kd" or "Kd value" is measured by using surface plasmon resonance assays using BIAcore™-2000 or BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the manufacturer's instructions. Antigen is diluted with 10 mM sodium acetate, pH 4.8, into 5 µg/ml (~0.2 µM) and then injected at a flow rate of 5 µl/minute to achieve approximately 10 response units (RU) of coupled protein. Following the injection of antigen, 1M ethanolamine solution is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. On-rates (kon) and off-rates (koff) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g., Chen, Y., et al., (1999) J. Mol. Biol. 293: 865-881. If the on rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody solution (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The term "koff" refers to the off rate constant of a particular interaction between a binding molecule and antigen. The off rate constant koff can be measured using bio-layer interferometry, for example, using Octet™ system.

"On-rate" or "kon" according to the present invention can be also measured by using the above surface plasmon resonance assays using BIAcore™-2000 or BIAcore™-3000 (BIAcore, Inc., Piscataway, N.J.) at 25° C. with immobilized antigen CM5 chips at ~10 relative units (response units, RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the manufacturer's instructions. Antigen is diluted with 10 mM sodium acetate, pH 4.8, into 5 μg/ml (~0.2 μM) and then injected at a flow rate of 5 μl/minute to achieve approximately 10 response units (RU) of coupled protein. Following the injection of antigen, 1M ethanolamine solution is injected to block unreacted groups.

Unless specified otherwise, the term "biologically active" and "biological activity" and "biological characteristics" with respect to a polypeptide of the invention means having the ability to bind to a biological molecule.

The term "biological molecule" refers to a nucleic acid, a protein, a carbohydrate, a lipid, and combinations thereof. In one embodiment, the biological molecule exists in nature.

Antibody fragments, such as Fab and F(ab')2 fragments, can be prepared from whole antibodies using conventional techniques, such as papain or pepsin digestion of whole antibodies. Moreover, antibodies, portions thereof and immunoadhesion molecules can be prepared using standard recombinant DNA techniques, for example, as described herein.

The term "recombinant antibody" is intended to refer to an antibody that is expressed in a cell or cell line comprising nucleotide sequence(s) encoding antibodies, wherein said nucleotide sequence(s) is not naturally associated with the cell.

As used herein, the term "variant antibody" is intended to refer to an antibody which has an amino acid sequence which differs from the amino acid sequence of a "parental" antibody thereof by virtue of adding, deleting and/or substituting one or more amino acid residues as compared to the sequence of a parental antibody. In a preferred embodiment, a variant antibody comprises at least one or more (e.g., one to twelve, e.g., two, three, four, five, six, seven, eight or nine, ten, eleven or twelve; in some embodiments, a variant antibody comprises from one to about ten) additions, deletions, and/or substitutions of amino acids as compared to a parental antibody. In some embodiments, such additions, deletions and/or substitutions are made in the CDRs of a variant antibody. Identity or homology with respect to the sequence of a variant antibody is defined herein as the percentage of amino acid residues in the variant antibody sequence that are identical to the parental antibody residues, after aligning the sequences and introducing gaps, if necessary, to achieve the maximum percent of sequence identity. A variant antibody retains the ability to bind to the same antigen, and preferably to an epytope, to which the parental antibody binds; and in some embodiments, at least one property or biological activity are superior to those of a parental antibody. For example, a variant antibody may have, e.g., a stronger binding affinity, longer half-life, lower IC50, or enhanced ability to inhibit antigen biological activity as compared to a parental antibody. The variant antibody of particular interest herein is one which displays at least 2 fold, (preferably at least 5 fold, 10 fold or 20 fold) enhancement in biological activity as compared to a parental antibody.

The term "bispecific antibody" refers to an antibody having an antigen-binding domain(s) that are capable of specific binding to two different epitopes on a single biological molecule or capable of specific binding to epitopes on two different biological molecules. The bispecific antibody is also referred to herein as having "dual specificity" or as being a "dual specificity" antibody.

In a broad sense, the term "chimeric antibody" is intended to refer to an antibody that comprises one or more regions of one antibody, and one or more regions of one or several other antibodies, typically, a partially human and partially non-human antibody, i.e. derived partially from a non-human animal, such as mice, rats, or the like vermin, or the Camelidae such as llama and alpaca. Chimeric antibodies are generally preferred over non-human antibodies in order to reduce the risk of a human anti-antibody immune response, e.g. a human anti-mouse antibody immune response in the case of a murine antibody. An example of a typical chimeric antibody is one in which the variable region sequences are murine sequences, while the constant region sequences are human. In the case of a chimeric antibody, the non-human parts may be subjected to further alteration in order to humanize the antibody.

The term "humanization" is intended to refer to the fact that when an antibody has a fully or partially non-human origin, for example, a mouse or llama antibody obtained by immunizing mice or lamas, respectively, with an antigen of interest, or is a chimeric antibody based on such an antibody of a mouse or llama, it is possible to substitute certain amino acids, in particular in the framework regions and constant domains of heavy and light chains, in order to avoid or minimize the immune response in humans. Antibodies interact with target antigens predominantly through amino acid residues that are located in the six heavy and light chain CDRs. For this reason, amino acid sequences within CDRs are far more variable between individual antibodies than those outside of CDRs. Because CDR sequences are responsible for most antibody-antigen interactions, it is possible to express recombinant antibodies that mimic the properties of a specific naturally occurring antibody, or more generally, of any specific antibody with said amino acid sequence, e.g., by constructing expression vectors that express CDR sequences from the specific antibody and framework sequences from a different antibody. As a result, it is possible to "humanize" a non-human antibody and, to a large extent, preserve binding specificity and affinity of the initial antibody. Although it is not possible to precisely predict the immunogenicity and thereby the human anti-antibody response of a particular antibody, non-human antibodies are typically more immunogenic than human antibodies. Chimeric antibodies, where the foreign (e.g. vermin or Camelidae) constant regions have been substituted with sequences of human origin, have shown to be generally less immunogenic than those of fully foreign origin, and the trend in therapeutic antibodies is towards humanized or fully human antibodies. Therefore, chimeric antibodies or other antibodies of non-human origin can be humanized to reduce the risk of a human anti-antibody response.

For chimeric antibodies, humanization typically involves modification of the framework regions of variable region sequences. Amino acid residues that are part of complementarity determining regions (CDRs) will be most often not modified by virtue of humanization, although in some cases it may be desirable in order to modify individual amino acid residues of a CDR, for example, in order to delete a glycosylation site, deamidation site, aspartate isomerization site, or undesired cysteine or methionine residues. N-linked glycosylation is made by virtue of attaching an oligosaccharide chain to an asparagine residue in a tripeptide sequence Asn-X-Ser or Asn-X-Thr, where X can be any amino acid except Pro. Removal of an N-glycosylation site may be achieved by mutating either the Asn or Ser/Thr residue by a different residue, preferably by way of conservative substitution. Deamidation of asparagine and glutamine residues can occur depending on such factors as pH and surface exposure. Asparagine residues are especially susceptible to deamidation, primarily when present in sequence Asn-Gly, and in a lesser degree in other dipeptide sequences such as Asn-Ala. Provided a CDR sequence comprises such a deamidation site, in particular Asn-Gly, it may be desirable to remove this site, typically by virtue of conservative substitution to delete one of the implicated residues.

Numerous methods for humanization of an antibody sequence are known in the art. One commonly used method is CDR grafting. CDR grafting may be based on the CDR definitions by Kabat, although the last edition (Magdelaine-Beuzelin et al., Crit Rev. Oncol Hematol. 64:210 225 (2007)) suggests that the IMGT® (the international ImMunoGeneTics information System®) definition may improve humanization results (see Lefranc et al., Dev. Comp Immunol. 27:55-77 (2003)). In some cases, CDR grafting may reduce the binding specificity and affinity, and thus the biological activity, of a CDR grafted non-human antibody, as compared to a parental antibody from which the CDRs were obtained. Back mutations (which are sometimes referred to as "framework region repair" may be introduced at selected positions of a CDR grafted antibody, typically in framework regions, in order to restore the binding specificity and affinity of a parental antibody. Identification of positions for possible back mutations can be performed using information available in the literature and in antibody databases. Amino acid residues that are candidates for back mutations are typically those that are located at the surface of an antibody molecule, whereas residues that are buried or that have a low degree of surface exposure will not normally be altered. An alternative humanization technique to CDR grafting and back mutation is resurfacing, in which non-surface exposed residues of non-human origin are retained, whereas surface residues are altered to human residues.

Fully human antibodies can be generated using two techniques: using in vitro collected phage libraries or in vivo immunization of humanized animals (mice, rats, etc.).

Construction of combinatorial phage antibody libraries begins with selection of a source of gene repertoire, depending on which several antibody library types can be distinguished: naive, immune and synthetic. Naive and immune libraries are constructed using naturally reorganized genes, which encode the variable immunoglobulin domains of healthy donors or donors immunized with a certain antigen, respectively. mRNA from the antibody-producing lymphoid cell line is isolated for this purpose. Peripheral blood lymphocytes are mainly used, but splenocytes have been used as well [Sheets M D, Amersdorfer P, Finnern R, Sargent P, Lindquist E, Schier R, et al. Efficient construction of a large nonimmune phage antibody library: the production of high-affinity human single-chain antibodies to protein antigens. Proc Natl Acad Sci USA 1998, 95:6157-6162 and de Haard H J, van Neer N, Reurs A, Hufton S E, Roovers R C, Henderikx P, et al. A large non-immunized human Fab fragment phage library that permits rapid isolation and kinetic analysis of high affinity antibodies. J Biol Chem 1999, 274:18218-18230.], клетки миндалин или лимфоциты костного мозга [Vaughan T J, Williams A J, Pritchard K, Osbourn J K, Pope A R, Earnshaw J C, et al. Human antibodies with sub-nanomolar affinities isolated from a large non-immunized phage display library. Nat Biotechnol 1996, 14:309-314.]. cDNA is then synthesized on the base of mRNA, and both oligo-dT primers and statistically devised hexanucleotides can be used that yield cDNA copies of all the possible variants of genes encoding the variable domains of antibodies [Ulitin A B, Kapralova M V, Laman A G, Shepelyakovskaya A O, Bulgakova E B, Fursova K K, et al. The library of human miniantibodies in the phage display format: Designing and testing DAN: Izd-vo "Nauka"; 2005.].

One or several primers can be simultaneously used to limit the range of amplified genes to one or several variable domain gene families or antibody isotypes, now at cDNA level [Marks J D, Hoogenboom H R, Bonnert T P, McCafferty J, Griffiths A D, Winter G. Bypassing immunization. Human antibodies from V-gene libraries displayed on phage. J Mol Biol 1991, 222:581-597]. The primers used for amplification of genes encoding immunoglobulins are complementary to their most conservative regions. Their sequences are selected from gene collections that are organized into databases, such as Kabat or V BASE databases. The primer design also provides for internal restriction sites for cloning the PCR-products into the appropriate vectors.

Construction of synthetic libraries is based on replacement of natural CDRs with a set of random sequences. In this case, it is possible to generate a vast variety of antigen-binding sites.

Phage display is one of the most powerful and widely used in vitro technique for search for antibodies. In 1985, Smith found that foreign DNA sequences could be cloned into filamentous bacteriophage M13 and that such cloned sequence can be expressed on the surface of phage particles as fusion proteins (Smith G P: Filamentous fusion phage: novel expression vectors that display cloned antigens on the virion surface. Science 1985, 228:1315-1317.). Thus, it is possible to select the fusion proteins of interest based on their ability to bind other proteins. This discovery was combined with PCR amplification methods, which made it possible to clone the cDNA repertoire of immunoglobulin genes to create a variety of phage libraries containing variable domains that can be used to quickly search for target-specific monoclonal antibodies. Phage library repertoire reflects repertoire of B-cell antibody of each person or animal whose blood was used to create the library. In 1995, two papers described the production of genetically engineered mice which were capable of expression of fully human antibodies, the repertoires of which are comparable to those obtained by the hybridoma technology (Lonberg N, Taylor L D, Harding F A, Trounstine M, Higgins K M, Schramm S R, Kuo C C, Mashayekh R, Wymore K, McCabe J G et al.: Antigen-specific human antibodies from mice comprising four distinct genetic modifications. Nature 1994, 368:856-859). In these animals, their own endogenous heavy and k light immunoglobulin chain genes were deliberately destroyed, followed by introduction of transgenes, which are the segments of human heavy and k light chain genes. It turned out that human gene repertoire can be used by the mouse immune system to produce high specificity and high affinity antibodies against a greater variety of antigens. Despite the fact that transgenic mice express B-cell receptors that are essentially hybrids of mouse and human components (human immunoglobulin, mouse Iga, IgR, and other signaling molecules), their B-cells develop and mature normally.

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., Proc Natl Acad Sci USA, 94:412-417 (1997) and the stepwise in vitro affinity maturation method by Wu et al., Proc Natl Acad Sci USA 95:6037 6042 (1998).

The term "monoclonal antibody" or "mAb" refers to an antibody that is synthesized and isolated by a separate clonal population of cells. The clonal population can be a clonal population of immortalized cells. In some embodiments, the immortalized cells in a clonal population are hybrid cells—hybridomas—typically produced by the fusion of individual B lymphocytes from immunized animals with individual cells from a lymphocytic tumor. Hybridomas are a type of constructed cells and do not exist in nature.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "isolated" used to describe various antibodies in this description refers to an antibody which has been identified and separated and/or regenerated from a cell or cell culture, in which the antibody is expressed. Impurities (contaminant components) from its natural environment are materials which would interfere with diagnostic or therapeutic uses of the polypeptide, and may include enzymes, hormones, and other proteinaceous or nonproteinaceous solutes. In preferred embodiments, an antibody is purified (1) to a degree sufficient to obtain at least 15 residues of N-terminal or internal amino acid sequence by use of a spinning cup sequenator (Edman sequenator), or (2) to homogeneity by SDS-PAGE under nonreducing or reducing conditions using Coomassie Brilliant Blue, or preferably silver stain. Isolated antibody includes the antibody in situ within recombinant cells since at least one component of the polypeptide's natural environment will not be present. Isolated polypeptide is typically prepared by at least one purification step.

An "isolated" nucleic acid molecule is one which is identified and separated from at least one nucleic acid molecule-impurity, which the former is bound to in the natural source of antibody nucleic acid. An isolated nucleic acid molecule is different from the form or set in which it is found under natural conditions. Thus, an isolated nucleic acid molecule is different from a nucleic acid molecule that exists in cells under natural conditions. An isolated nucleic acid molecule however includes a nucleic acid molecule located in cells in which the antibody is normally expressed, for example, if the nucleic acid molecule has a chromosomal localization that is different from its localization in cells under natural conditions.

The term "epitope" as used herein is intended to refer to a portion (determinant) of an antigen that specifically binds to a binding molecule (for example, an antibody or a related molecule, such as a bispecific binding molecule). Epitope determinants usually consist of chemically active surface groupings of molecules such as amino acids or carbohydrates or sugar side chains and typically comprise specific three dimensional structural characteristics, as well as specific charge characteristics. Epitopes can be either "linear" or "conformational". In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope of an antigen is determined, it is possible to generate antibodies to that epitope using techniques well known in the art. In addition, generation and characterization of antibodies or other binding molecules may elucidate information about desirable epitopes. From this information, it is then possible to competitively screen antibodies for binding to the same or identical epitopes, e.g., by conducting competition studies to find binding molecules that compete with one another for binding to the antigen.

The term "peptide linker" as used herein is intended to mean any peptide having the ability to combine domains, with a length which depends on the domains which it binds to each other, and comprising any amino acid sequence. Preferably, the peptide linker has a length of more than 5 amino acids and consists of any set of amino acids selected from G, A, S, P, E, T, D, K.

The term "in vitro" refers to a biological entity, a biological process, or a biological reaction outside the body under artificial conditions. For example, a cell grown in vitro is to be understood as a cell grown in an environment outside the body, e.g., in a test tube, a culture vial, or a microtiter plate.

The term "$IC_{50}$" (50% inhibitory concentration) refers to drug concentration and indicates inhibitor volume required to inhibit a biological process by 50%. $IC_{50}$ value can be calculated using appropriate dose-response curves, using special statistical software for curve fitting.

The term "ED50" (EC50) (50% effective dose/concentration) refers to drug concentration to produce a 50% biological effect (which may include cytoxicity).

The term antibody "effector function" refers to biological activities attributable to the Fc-region (native Fc-region sequence or Fc-region amino acid variants) of an antibody, which vary with the antibody isotype. Examples of antibody effector functions include: $Cl_q$ binding and complement dependent cytotoxicity; Fc receptor binding; antibody-dependent cell-mediated cytotoxicity (ADCC); phagocytosis; down regulation of cell surface receptors (e.g., B-cell receptor, BCR), and B-cell activation.

"Antibody-dependent cellular cytotoxicity" or "ADCC" refers to an immunocompetent effector cell-mediated (T-killers, natural killers, etc.) response, in which nonspecific cytotoxic cells that express Fc receptors (FcR) (for example, natural killer (NK) cells, neutrophils, and macrophages) recognize bound antibody on a target cell and subsequently cause lysis or phagocytosis of the target cell.

The primary cells for mediating ADCC, NK cells, express FcγRJII only, whereas monocytes express FcγRI, FcγRII and FcγRIII. FcR expression on hematopoietic cells is summarized in Table 3 on page 464 of Ravetch and Kinet, Annu. Rev. Immunol 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95: 652-656 (1998).

"Human effector cells" are leukocytes which express one or more Fc receptors and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g., from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA ("activating receptor") and FcγRIIB ("inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daeron, Annu. Rev. Immunol. 15: 203-234 (1997)). FcRs are reviewed in Ravetch and Kinet, Annu. Rev. Immunol 9: 457-92 (1991). Other FcRs, including those to be identified in the future, are encompassed by the term "FcR" herein. The term also includes the neonatal receptor, FcRn, which is responsible for the transfer of maternal IgGs to the fetus.

"Complement dependent cytotoxicity" or "CDC" refers to the ability of a molecule to lyse a target in the presence of complement. The complement activation pathway is initiated by the binding of the first component of the complement system (C1q) to a molecule {e.g., an antibody) complexed with a cognate antigen. To assess complement activation, a CDC assay, e.g., as described in Gazzano-Santoro et al., J. Immunol. Methods 202: 163 (1996) may be performed.

The term "identity" or "homology" is construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions will be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, 1710 University Ave., Madison, WI 53705). This software matches similar sequences by assigning a degree of homology to various substitutions, deletions (eliminations), and other modifications.

The term "homologous" with regard to a polypeptide sequence of an antibody should be construed as an antibody exhibiting at least 70%, preferably 80%, more preferably 90% and most preferably 95% sequence identity relative to a polypeptide sequence. The term in relation to a nucleic acid sequence should be construed as a sequence of nucleotides exhibiting at least 85%, preferably 90%, more preferably 95% and most preferably 97% sequence identity relative to a nucleic acid sequence.

Modification(s) of amino acid sequences of antibodies described herein are provided. For example, it may be desirable to improve the binding affinity and/or other biological properties of the antibody. Amino acid sequence variants of antibody are prepared by introducing appropriate nucleotide changes into the antibody nucleic acid, or by peptide synthesis. Such modifications include, for example, deletions, and/or insertions and/or substitutions of residues within the amino acid sequences of antibody. Any combination of deletion, insertion, and substitution is made to arrive at the final construct, provided that the final construct possesses the desired characteristics. The amino acid changes also may alter post-translational processes in the antibody, such as changing the number or position of glycosylation sites.

Variant of modification of amino acid sequences of antibodies using amino acid substitutions. Such a variant is substitution of at least one amino acid residue in the antibody molecule with a different residue. The sites of greatest interest for substitutional mutagenesis include hypervariable regions or CDRs, but FR or Fc alterations are also contemplated. Conservative substitutions are shown in Table 1 under "preferred substitutions" If such substitutions cause alteration of the biological activity, further substantial changes can be made, which are denoted as "exemplary substitutions" set forth in Table A, or alterations described in more detail below when describing amino acid classes, and also product screening may be performed.

TABLE 1

| Original residue | Exemplary substitutions | Preferred substitutions |
| --- | --- | --- |
| Ala (A) | Val; Leu; Ile | Val |
| Arg (R) | Lys; Gin; Asn | Lys |
| Asn (N) | Gin; His; Asp, Lys; Arg | Gin |
| Asp (D) | Glu; Asn | Glu |
| Cys (C) | Ser; Ala | Ser |
| Gln (Q) | Asn; Glu | Asn |
| Glu (E) | Asp; Gin | Asp |
| Gly (G) | Ala | Ala |
| His (H) | Asn; Gin; Lys; Arg | Arg |
| Ile (I) | Leu; Val; Met; Ala; Phe; Norleucine | Leu |
| Leu (L) | Norleucine; Ile; Val; Met; Ala; | Ile |
| | | Phe |
| Lys (K) | Arg; Gin; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, determining a fragment or a region of a nucleic acid, containing unnatural nucleotides or not, and being either a double-strand DNA or RNA, a single-strand DNA or RNA, or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Thus, isolated nucleic acids obtained by recombinant genetics, by means, for example, of host cells, or obtained by chemical synthesis should also be mentioned here.

A reference to a nucleotide sequence encompasses the complement thereof unless otherwise specified. Thus, a reference to a nucleic acid having a particular sequence should be understood as one which encompasses the complementary strand thereof with the complementary sequence thereof.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader sequence is operably linked to DNA for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

The term "vector" as used herein means a nucleic acid molecule capable of transporting another nucleic acid to which it has been linked. In some embodiments, a vector is a plasmid, i.e., a circular double stranded piece of DNA into which additional DNA segments may be ligated. In some embodiments, a vector is a viral vector, wherein additional DNA segments may be ligated into the viral genome. In some embodiments, vectors are capable of autonomous replication in a host cell into which they are introduced (e.g., bacterial vectors having a bacterial origin site of replication and episomal mammalian vectors). In further embodiments, vectors (e.g., non-episomal mammalian vectors) can be integrated into the genome of a host cell upon introduction into a host cell, and thereby are replicated along with the host gene. Moreover, certain vectors are capable of directing the expression of genes to which they are operatively linked. Such vectors are referred to herein as "recombinant expression vectors" (or simply, "expression vectors").

The term "recombinant host cell" (or simply "host cell") as used herein is intended to refer to a cell into which a recombinant expression vector has been introduced. The present invention relates to host cells, which may include, for example, a vector according to the invention described above. The present invention also relates to host cells that comprise, for example, a nucleotide sequence encoding a heavy chain or antigen-binding portions thereof, a light chain-encoding nucleotide sequence or antigen-binding portions thereof, or both, of the first binding domain and/or second binding domain of a binding molecule of the invention. It should be understood that "recombinant host cell" and "host cell" are intended to refer not only to a particular subject cell but to the progeny of such a cell as well. Since modifications may occur in succeeding generations due to either mutation or environmental influences, such progeny may not, in fact, be identical to a parental cell, however, such cells are still included within the scope of the term "host cell" as used herein.

The term "excipient" is used herein to describe any ingredient other than the compound(s) of the invention.

"Pharmaceutical composition" refers to a composition comprising an antibody of the present invention and at least one of components selected from the group comprising pharmaceutically acceptable and pharmacologically compatible fillers, solvents, diluents, carriers, auxiliary, distributing and sensing agents, delivery agents, such as preservatives, stabilizers, filler, disintegrators, moisteners, emulsifiers, suspending agents, thickeners, sweeteners, flavouring agents, aromatizing agents, antibacterial agents, fungicides, lubricants, and prolonged delivery controllers, the choice and suitable proportions of which depend on the type and way of administration and dosage. Examples of suitable suspending agents are ethoxylated isostearyl alcohol, polyoxyethene, sorbitol and sorbitol ether, microcrystalline cellulose, aluminum metahydroxide, bentonite, agar-agar and tragacant and their mixtures as well. Protection against action of microorganisms can be provided by various antibacterial and antifungal agents, such as, for example, parabens, chlorobutanole, sorbic acid, and similar compounds. Composition may also contain isotonic agents, such as, for example, sugars, polyols, sodium chloride, and the like. Prolonged action of composition may be achieved by agents slowing down absorption of active ingredient, for example, aluminum monostearate and gelatin. Examples of suitable carriers, solvents, diluents and delivery agents include water, ethanol, polyalcohols and their mixtures, natural oils (such as olive oil) and organic esters (such as ethyl oleate) for injections. Examples of fillers are lactose, milk-sugar, sodium citrate, calcium carbonate, calcium phosphate and the like. Examples of disintegrators and distributors are starch, alginic acid and its salts, silicates. Examples of suitable lubricants are magnesium stearate, sodium lauryl sulfate, talc and polyethylene glycol of high molecular weight. Pharmaceutical composition for peroral, sublingual, transdermal, intraocular, intramuscular, intravenous, subcutaneous, local or rectal administration of active ingredient, alone or in combination with another active compound may be administered to human and animals in a standard administration form, in a mixture with traditional pharmaceutical carriers. Suitable standard administration forms include peroral forms such as tablets, gelatin capsules, pills, powders, granules, chewing-gums and peroral solutions or suspensions; sublingual and transbuccal administration forms; aerosols; implants; local, transdermal, subcutaneous, intramuscular, intravenous, intranasal or intraocular forms and rectal administration forms.

"Medicament"—is a compound (or a mixture of compounds as a pharmaceutical composition) in the form of tablets, capsules, solutions, ointments and other ready forms intended for restoration, improvement or modification of physiological functions in humans and animals, and for treatment and prophylaxis of diseases, for diagnostics, anesthesia, contraception, cosmetology and others.

The term "disease or disorder mediated by the interaction between IL-5 and cellular receptor thereof" refers to any disease or disorder that is either directly, or indirectly associated with IL-5 and IL-5R, including etiology, development, progression, persistence or pathology of a disease or disorder. "Treat", "treating" and "treatment" refer to a method of alleviating or abrogating a biological disorder and/or at least one of attendant symptoms thereof. As used herein, to "alleviate" a disease, disorder or condition means reducing the severity and/or occurrence frequency of the symptoms of a disease, disorder, or condition. Further, references herein to "treatment" include references to curative, palliative and prophylactic treatment.

In one aspect, the subject of treatment, or patient, is a mammal, preferably a human subject. Said subject may be either male or female, of any age.

The term "disorder" means any condition that would benefit from treatment with the compound of the present invention. This includes chronic and acute disorders or diseases including those pathological conditions that predispose the mammal to the disorder in question. The preferred disorder to be treated herein is autoimmune diseases.

The terms "immune response", "autoimmune response" and "autoimmune inflammation" refer, for example, to the action of lymphocytes, antigen-presenting cells, phagocytic cells, granulocytes and soluble macromolecules produced by said cells or liver cells (including antibodies, cytokines and complement produced in the result of selective damage, destruction or elimination of invasive pathogens, cells or tissues infected with pathogens, cancer cells or, in cases of autoimmunity or pathological inflammation, normal cells or tissues from the human body).

The term "autoimmune disease" as used herein refers to a non-malignant disease or disorder arising from and directed against an individual's own (auto) antigens and/or tissues.

The term encompasses, but is not limited to, rheumatoid arthritis, osteoarthritis, juvenile chronic arthritis, septic arthritis, Lyme osteoarthritis, psoriatic arthritis, reactive arthritis, spondyloarthropathy, systemic lupus erythematosus, Crohn's disease, ulcerative colitis, inflammatory bowel disease, diabetes mellitus, thyroiditis, asthma, allergic diseases, psoriasis, atopic dermatitis, scleroderma, reaction "graft versus host", organ transplant rejection, acute or chronic immune disease associated with organ transplantation, sarcoidosis, Kawasaki disease, Graves disease, nephrotic syndrome, chronic fatigue syndrome, Wegener's granulomatosis, Henoch-Schonlein purpura, microscopic renal vasculitis, chronic active hepatitis, uvenita, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, adult (acute) respiratory distress syndrome, alopecia, alopecia areata, seronegative arthropathy, arthropathy, Reiter's disease, psoriatic arthropathy associated with ulcerative colitis arthropathy, atopic allergy, autoimmune bullous diseases, pemphigus vulgaris, sheet-like pemphigus, pemphigoid disease, linear IgA, an autoimmune hemolytic anemia, Coombs-positive hemolytic anemia, pernicious anemia, juvenile pernicious anemia, arthritis, primary sclerosing hepatitis A, cryptogenic autoimmune hepatitis, fibrosis lung disease, cryptogenic fibrosis alveolitis, post-inflammatory interstitial lung disease, interstitial pneumonitis, chronic eosinophilic pneumonia, post-infectious interstitial lung disease, gouty arthritis, autoimmune hepatitis, autoimmune hepatitis type I (classical autoimmune hepatitis or lupoid), autoimmune hepatitis type II, osteoarthritis, primary sclerosing cholangitis, psoriasis type I, psoriasis type II, idiopathic leucopenia, autoimmune neutropenia, renal NOS-disease, glomerulonephritis, microscopic renal vasculitis, discoid lupus erythematosus, idiopathic or NOS-male infertility, autoimmunity to sperm, multiple sclerosis (all subtypes), sympathetic ophthalmia, pulmonary hypertension secondary to connective tissue disease, Goodpasture syndrome, pulmonary manifestations of polyarthritis nodosa, acute rheumatic fever, rheumatoid spondylitis, ankylosing spondylitis, Still's disease, systemic sclerosis, Sjögren syndrome, Takayasu's disease/arteritis, autoimmune thrombocytopenia, idiopathic thrombocytopenia, autoimmune thyroid disease, hyperthyroidism, goiter autoimmune hypothyroidism (Hashimoto's disease), autoimmune atrophic hypothyroidism, primary myxedema, phacogenic uveitis, primary vasculitis, vitiligo, acute liver disease, chronic liver disease, allergies, asthma, psychiatric disorders (including depression and schizophrenia), type Th2/type Th1-mediated diseases, conjunctivitis, allergic contact dermatitis, allergic rhinitis, deficiency of alpha-1-antitrypsin, amyotrophic lateral sclerosis, anemia, cystic fibrosis, disorders associated with cytokine therapy, demyelinating disease, dermatitis, iridocyclitis/uveitis/optic neuritis, ischemia-reperfusion injury, ischemic stroke, juvenile rheumatoid arthritis, autoimmune enteropathy, autoimmune hearing loss, autoimmune lymphoproliferative syndrome, autoimmune myocarditis, autoimmune premature ovarian failure, and blepharitis. The antibody can also treat any combination of the above disorders.

"Therapeutically effective amount" is intended to refer to that amount of the therapeutic agent being administered which will relieve to some extent one or more of the symptoms of the disorder being treated.

The term "chronic" use refers to continued (uninterrupted) use of agent(s) as opposed to acute (short-term) route of administration so as to sustain the initial therapeutic effect (activity) for a long period of time.

"Intermittent" use refers to treatment that is not carried out consistently without interruptions, but which is rather periodic in nature.

As used herein, the words "comprise," "have," "include," or variations such as "comprises," "comprising," "has," "having," "includes" or "including", and all grammatical variations thereof will be understood to imply the inclusion of a stated integer or group of integers but not the exclusion of any other integer or group of integers.

DETAILED DESCRIPTION OF THE INVENTION

Antibody

The present invention relates to antibodies or antigen-binding fragment that specifically bind to IL-5Rα.

In one embodiment, the present invention relates to an isolated antibody or antigen-binding fragment thereof, which specifically binds to IL-5Rα, and comprises:
(a) a heavy chain variable region comprising CDR3 comprising an amino acid sequence that is at least 80%, 85% or 92% homologous or identical to the sequence DYATNYGVPYFGS (SEQ ID NO: 3), i.e. CDR3 is the sequence DYATNYGVPYFGS (SEQ ID NO: 3) or the sequence DYATNYGVPYFGS (SEQ ID NO: 3) with 1 or 2 substitutions, and (b) a light chain variable region comprising CDR3 comprising an amino acid sequence that is at least 80%, 83% or 91% homologous or identical to the sequence QSYDSSLSGHVV (SEQ ID NO:8), i.e. CDR3 is the sequence QSYDSSLSGHVV (SEQ ID NO:8) or the sequence QSYDSSLSGHVV (SEQ ID NO:8) with 1 or 2 substitutions.

In one embodiment, the present invention relates to an isolated antibody or antigen-binding fragment thereof, which specifically binds to IL-5Rα, and comprises a heavy chain variable region comprising CDR3 comprising the amino acid sequence DYATNYGVPYFGS (SEQ ID NO: 3).

In one embodiment, the present invention relates to an isolated antibody or antigen-binding fragment thereof, which specifically binds to IL-5Rα, and comprises a light chain variable region comprising CDR3 comprising the amino acid sequence QSYDSSLSGHVV (SEQ ID NO:8).

In one embodiment, the present invention relates to an isolated antibody or antigen-binding fragment thereof, which specifically binds to IL-5Rα, and comprises:
(a) a heavy chain variable region comprising CDR3 comprising the amino acid sequence DYATNYGVPYFGS (SEQ ID NO: 3), and
(b) a light chain variable region comprising CDR3 comprising the amino acid sequence QSYDSSLSGHVV (SEQ ID NO:8).

In one embodiment, the present invention relates to an isolated antibody or antigen-binding fragment thereof, which specifically binds to IL-5Rα, and comprises:
(a) a heavy chain variable region comprising:
(i) CDR1 comprising an amino acid sequence that is at least 80% homologous or identical to the sequence NYAMS (SEQ ID NO: 1), i.e. CDR1 is the sequence NYAMS (SEQ ID NO: 1) or the sequence NYAMS (SEQ ID NO: 1) with 1 substitution;
(ii) CDR2 comprising an amino acid sequence that is at least 80%, 88%, or 94% homologous or identical to the sequence AINSGGKSTNYADSVKG (SEQ ID NO: 2), i.e. CDR2 is the sequence DYATNYGVPYFGS (SEQ ID NO: 2) or the sequence AINSGGKSTNYADSVKG (SEQ ID NO: 2) with 1 or 2 substitutions;
(iii) CDR3 comprising an amino acid sequence that is at least 80%, 85%, or 92% homologous or identical to the sequence DYATNYGVPYFGS (SEQ ID NO: 3), i.e. CDR3 is the sequence DYATNYGVPYFGS (SEQ ID NO: 3) or the sequence DYATNYGVPYFGS (SEQ ID NO: 3) with 1 or 2 substitutions;
and/or
(b) a light chain variable region comprising:
(i) CDR1 comprising an amino acid sequence that is at least 80%, 85%, or 92% homologous or identical to the sequence SGSRSNIGSGYDVH (SEQ ID NO: 6), i.e. CDR1 is the sequence SGSRSNIGSGYDVH (SEQ ID NO: 6) or the sequence SGSRSNIGSGYDVH (SEQ ID NO: 6) with 1 or 2 substitutions;
(ii) CDR2 comprising an amino acid sequence that is at least 80% or 85% homologous or identical to the sequence DDNNRPS (SEQ ID NO: 7), i.e. CDR2 is the sequence DDNNRPS (SEQ ID NO: 7) or the sequence DDNNRPS (SEQ ID NO: 7) with 1 substitution;
(iii) CDR3 comprising an amino acid sequence that is at least 80%, 83%, or 91% homologous or identical to the sequence QSYDSSLSGHVV (SEQ ID NO:8), i.e. CDR3 is the sequence QSYDSSLSGHVV (SEQ ID NO:8) or the sequence QSYDSSLSGHVV (SEQ ID NO:8) with 1 or 2 substitutions.

In one embodiment, the present invention relates to an isolated antibody or antigen-binding fragment thereof, which specifically binds to IL-5Rα, and comprises:
(a) a heavy chain variable region comprising:
(i) CDR1 comprising the amino acid sequence NYAMS (SEQ ID NO: 1),
(ii) CDR2 comprising the amino acid sequence AINSGGKSTNYADSVKG (SEQ ID NO: 2),
(iii) CDR3 comprising the amino acid sequence DYATNYGVPYFGS (SEQ ID NO: 3), and/or
(b) a light chain variable region comprising:
(i) CDR1 comprising the amino acid sequence SGSRSNIGSGYDVH (SEQ ID NO: 6),
(ii) CDR2 comprising the amino acid sequence DDNNRPS (SEQ ID NO: 7),
(iii) CDR3 comprising the amino acid sequence QSYDSSLSGHVV (SEQ ID NO:8).

In one embodiment, the present invention relates to an isolated antibody or antigen-binding fragment thereof, which specifically binds to IL-5Rα, and comprises:
(a) a heavy chain variable region comprising an amino acid sequence that is at least 90%, 91%, 92%, 93%, 94%, 95%, 96%, 97%, 98% or 99% homologous or identical to a sequence selected from the group:

```
                                            (SEQ ID NO: 4)
QVTLKESGGGLVQPGGSLRLSCAASGFTFSNYAMSWVRQAPGKGLEWVSA

INSGGKSTNYADSVKGRFTISRDNAKNTLYLQMNSLRAEDTAVYYCADYA

TNYGVPYFGSWGQGTTVTVSS
or (SEQ ID NO: 5)
QVQLQESGGGLVQPGGSLRLSCAASGFTFSNYAMSWVRQAPGKGLEWVSA

INSGGKSTNYADSVKGRFTISRDNAKNTLYLQMNSLRAEDTAVYYCADYA

TNYGVPYFGSWGQGTMVTVSS,
``` and/or
(b) a light chain variable region comprising an amino acid sequence that is at least 90%, 91%, 92%, 93%, 94%, 95%, 96%, 97%, 98% or 99% homologous or identical to a sequence selected from the group:

```
                                            (SEQ ID NO: 9)
QAGLTQPPSVSAAPGQRVTISCSGSRSNIGSGYDVHWYQQVPGTAPKLLI

FDDNNRPSGVPDRFSGSKSGTSASLAITGLQAEDEADYYCQSYDSSLSGH

VVFGGGTKLTVL
or (SEQ ID NO: 10)
QSVLTQPPSVSAAPGQRVTISCSGSRSNIGSGYDVHWYQQLPGTAPKLLI

YDDNNRPSGVPDRFSGSKSGTSASLAITGLQAEDEADYYCQSYDSSLSGH

VVFGGGTKLTVL.
```

In one embodiment, the present invention relates to an isolated antibody or antigen-binding fragment thereof, which specifically binds to IL-5Rα, and comprises:

(a) a heavy chain variable region comprising an amino acid sequence selected from the group:

(SEQ ID NO: 4)
QVTLKESGGGLVQPGGSLRLSCAASGFTFSNYAMSWVRQAPGKGLEWVSA

INSGGKSTNYADSVKGRFTISRDNAKNTLYLQMNSLRAEDTAVYYCADYA

TNYGVPYFGSWGQGTTVTVSS
or (SEQ ID NO: 5)
QVQLQESGGGLVQPGGSLRLSCAASGFTFSNYAMSWVRQAPGKGLEWVSA

INSGGKSTNYADSVKGRFTISRDNAKNTLYLQMNSLRAEDTAVYYCADYA

TNYGVPYFGSWGQGTMVTVSS, and/or
(b) a light chain variable region comprising an amino acid sequence selected from the group:

(SEQ ID NO: 9)
QAGLTQPPSVSAAPGQRVTISCSGSRSNIGSGYDVHWYQQVPGTAPKLLI

FDDNNRPSGVPDRFSGSKSGTSASLAITGLQAEDEADYYCQSYDSSLSGH

VVFGGGTKLTVL
or (SEQ ID NO: 10)
QSVLTQPPSVSAAPGQRVTISCSGSRSNIGSGYDVHWYQQLPGTAPKLLI

YDDNNRPSGVPDRFSGSKSGTSASLAITGLQAEDEADYYCQSYDSSLSGH

VVFGGGTKLTVL.

In one embodiment, the present invention relates to an isolated antibody or antigen-binding fragment thereof, which specifically binds to IL-5Rα, and comprises:
(a) a heavy chain comprising an amino acid sequence that is at least 90%, 91%, 92%, 93%, 94%, 95%, 96%, 97%, 98% or 99% homologous or identical to a sequence selected from the group:

(SEQ ID NO: 11)
QVTLKESGGGLVQPGGSLRLSCAASGFTFSNYAMSWVRQAPGKGLEWVSA

INSGGKSTNYADSVKGRFTISRDNAKNTLYLQMNSLRAEDTAVYYCADYA

TNYGVPYFGSWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K
or (SEQ ID NO: 12)
QVQLQESGGGLVQPGGSLRLSCAASGFTFSNYAMSWVRQAPGKGLEWVSA

INSGGKSTNYADSVKGRFTISRDNAKNTLYLQMNSLRAEDTAVYYCADYA

TNYGVPYFGSWGQGTMVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K, and/or
(b) a light chain comprising an amino acid sequence that is at least 90%, 91%, 92%, 93%, 94%, 95%, 96%, 97%, 98% or 99% homologous or identical to the sequence (SEQ ID NO: 13)
QAGLTQPPSVSAAPGQRVTISCSGSRSNIGSGYDVHWYQQVPGTAPKLLI

FDDNNRPSGVPDRFSGSKSGTSASLAITGLQAEDEADYYCQSYDSSLSGH

VVFGGGTKLTVLRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC
or (SEQ ID NO: 14)
QSVLTQPPSVSAAPGQRVTISCSGSRSNIGSGYDVHWYQQLPGTAPKLLI

YDDNNRPSGVPDRFSGSKSGTSASLAITGLQAEDEADYYCQSYDSSLSGH

VVFGGGTKLTVLRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

In one embodiment, the present invention relates to an isolated antibody or antigen-binding fragment thereof, which specifically binds to IL-5Rα, and comprises:
(a) a heavy chain comprising an amino acid sequence selected from the group:

(SEQ ID NO: 11)
QVTLKESGGGLVQPGGSLRLSCAASGFTFSNYAMSWVRQAPGKGLEWVSA

INSGGKSTNYADSVKGRFTISRDNAKNTLYLQMNSLRAEDTAVYYCADYA

TNYGVPYFGSWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K
or (SEQ ID NO: 12)
QVQLQESGGGLVQPGGSLRLSCAASGFTFSNYAMSWVRQAPGKGLEWVSA

INSGGKSTNYADSVKGRFTISRDNAKNTLYLQMNSLRAEDTAVYYCADYA

TNYGVPYFGSWGQGTMVTVSSASTKGPSVFPLAPSSKSTSGGTAALGCLV

-continued
KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K, and/or
(b) a light chain comprising the amino acid sequence (SEQ ID NO: 13)
QAGLTQPPSVSAAPGQRVTISCSGSRSNIGSGYDVHWYQQVPGTAPKLLI

FDDNNRPSGVPDRFSGSKSGTSASLAITGLQAEDEADYYCQSYDSSLSGH

VVFGGGTKLTVLRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC or (SEQ ID NO: 14)
QSVLTQPPSVSAAPGQRVTISCSGSRSNIGSGYDVHWYQQLPGTAPKLLI

YDDNNRPSGVPDRFSGSKSGTSASLAITGLQAEDEADYYCQSYDSSLSGH

VVFGGGTKLTVLRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

In one embodiment, the isolated antibody, which specifically binds to IL-5Rα, is a monoclonal antibody:

In one embodiment, the monoclonal antibody, which specifically binds to IL-5Rα, is a full-length IgG antibody:

In one embodiment, the full-length IgG antibody, which specifically binds to IL-5Rα, is of human IgG1, IgG2, IgG3 or IgG4 isotype.

In one embodiment, the full-length IgG antibody, which specifically binds to IL-5Rα, is of human IgG1 isotype.

In one embodiment, the isolated antibody is antibody BCD133-03-002, which specifically binds to IL-5Rα, and comprises a heavy chain variable fragment comprising the amino acid sequence QVTLKESGGGLVQPGGSLRLSCAASGFTFSNYAMSWVRQAPGKGLEWVSAINSGGKSTNYADSVKGRFTISRDNAKNTLYLQMNSLRAEDTAVYYCADYATNY GVPYFGSWGQGTTVTVSS (SEQ ID NO: 19) and a light chain variable fragment comprising the amino acid sequence QAGLTQPPSVSAAPGQRVTISCSGSRSNIGSGYDVHW YQQVPGTAPKLLIFDD NNRPSGVPDRFSGSKSGTSASLAITGLQAEDEADYYCQSYDSSLSGHVVFGGG TKLTVL (SEQ ID NO: 20).

In one embodiment, the isolated antibody is antibody BCD133-03-020, which specifically binds to IL-5Rα, and comprises a heavy chain variable fragment comprising the amino acid sequence QVQLQESGGGLVQPGGSLRLSCAASGFTFSNYAMSWVRQAPGKGLEWVSAINSGGKSTNYADSVKGRFTISRDNAKNTLYLQMNSLRAEDTAVYYCADYATNY GVPYFGSWGQGTMVTVSS (SEQ ID NO: 21) and a light chain variable fragment comprising the amino acid sequence QAGLTQPPSVSAAPGQRVTISCSGSRSNIGSGYDVHW YQQVPGTAPKLLIFDD NNRPSGVPDRFSGSKSGTSASLAITGLQAEDEADYYCQSYDSSLSGHVVFGGG TKLTVL (SEQ ID NO: 22).

In one embodiment, the isolated antibody is antibody BCD133-03-021, which specifically binds to IL-5Rα, and comprises a heavy chain variable fragment comprising the amino acid sequence QVQLQESGGGLVQPGGSLRLSCAASGFTFSNYAMSWVRQAPGKGLEWVSAINSGGKSTNYADSVKGRFTISRDNAKNTLYLQMNSLRAEDTAVYYCADYATNY GVPYFGSWGQGTMVTVSS (SEQ ID NO: 23) and a light chain variable fragment comprising the amino acid sequence QSVLTQPPSVSAAPGQRVTISCSGSRSNIGSGYDVHW YQQLPGTAPKLLIYDD NNRPSGVPDRFSGSKSGTSASLAITGLQAEDEADYYCQSYDSSLSGHVVFGGG TKLTVL (SEQ ID NO: 24).

In one embodiment, the isolated antibody is antibody BCD133-03-002, which specifically binds to IL-5Rα, and comprises a heavy chain variable fragment comprising the amino acid sequence QVTLKESGGGLVQPGGSLRLSCAASGFTFSNYAMSWVRQAPGKGLEWVSAINSGGKSTNYADSVKGRFTISRDNAKNTLYLQMNSLRAEDTAVYYCADYATNY GVPYFGSWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHK PSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 25) and a light chain variable fragment comprising the amino acid sequence QAGLTQPPSVSAAPGQRVTISCSGSRSNIGSGYDVHW YQQVPGTAPKLLIFDD NNRPSGVPDRFSGSKSGTSASLAITGLQAEDEADYYCQSYDSSLSGHVVFGGG TKLTVLRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTK SFNRGEC (SEQ ID NO: 26).

In one embodiment, the isolated antibody is antibody BCD133-03-020, which specifically binds to IL-5Rα, and comprises a heavy chain comprising the amino acid sequence QVQLQESGGGLVQPGGSLRLSCAASGFTFSNYAMSWVRQAPGKGLEWVSAINSGGKSTNYADSVKGRFTISRDNAKNTLYLQMNSLRAEDTAVYYCADYATNY GVPYFGSWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHK PSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 27) and a light chain comprising the amino acid sequence QAGLTQPPSVSAAPGQRVTISCSGSRSNIGSGYDVHW YQQVPGTAPKLLIFDD NNRPSGVPDRFSGSKSGT-
SASLAITGLQAEDEADYYCQSYDSSLSGHVVFGGG
TKLTVLRTVAAPSVFIFPPSDEQLKSG-
TASVVCLLNNFYPREAKVQWKVDNAL
QSGNSQESVTEQDSKDSTYSLSSTLTL-
SKADYEKHKVYACEVTHQGLSSPVTK SFNRGEC
(SEQ ID NO: 28).

In one embodiment, the isolated antibody is antibody BCD133-03-021, which specifically binds to IL-5Rα, and comprises a heavy chain comprising the amino acid sequence QVQLQESGGGLVQPGGSLRLS-
CAASGFTFSNYAMSWVRQAPGKGLEWVSAI
NSGGKSTNYADSVKGRFTISRDNAKNTLYLQMNSL-
RAEDTAVYYCADYATNY GVPYFGSWGQGTMVTVS-
SASTKGPSVFPLAPSSKSTSGGTAALGCLVKDYFPE
PVTVSWNSGALTSGVHTFPAVLQSSGLYS-
LSSVVTVPSSSLGTQTYICNVNHK PSNTKVDKRVE-
PKSCDKTHTCPPCPA-
PELLGGPSVFLFPPKPKDTLMISRTPE
VTCVVVDVSHEDPE-
VKFNWYVDGVEVHNAKTKPREEQYN-
STYRVVSVLTVL HQDWLNGKEYKCKVSNKALPA-
PIEKTISKAKGQPREPQVYTLPPSREEMTKN
QVSLTCLVKGFYPSDIAVEWESNGQPEN-
NYKTTPPVLDSDGSFFLYSKLTVDK
SRWQQGNVFSCSVMHEALHNHYTQKSLSLSPGK
(SEQ ID NO: 29) and a light chain comprising the amino acid sequence
QSVLTQPPSVSAAPGQRVTISCSGSRSNIGSGYDVHW
YQQLPGTAPKLLIYDD NNRPSGVPDRFSGSKSGT-
SASLAITGLQAEDEADYYCQSYDSSLSGHVVFGGG
TKLTVLRTVAAPSVFIFPPSDEQLKSG-
TASVVCLLNNFYPREAKVQWKVDNAL
QSGNSQESVTEQDSKDSTYSLSSTLTL-
SKADYEKHKVYACEVTHQGLSSPVTK SFNRGEC
(SEQ ID NO: 30).

Nucleic Acid Molecules

The present invention also relates to nucleic acid molecules, in particular to sequences encoding antibody against IL-5Rα (interleukin 5 receptor α-chain) of the present invention, or any of fragments thereof, and their various combinations, which are described herein, optionally including any peptide linker sequence, which are connected therewith.

A reference to a nucleotide sequence encompasses the complement thereof unless otherwise specified. Thus, a reference to a nucleic acid having a particular sequence should be understood as one which encompasses the complementary strand thereof with the complementary sequence thereof. The term "polynucleotide" as used herein means a polymeric form of either nucleotides that are at least 10 bases in length, or ribonucleotides, or deoxyribonucleotides or a modified form of either type of nucleotide. The term includes single and double stranded forms.

The present invention also relates to nucleotide sequences that are at least 75%, 80%, 85%, 90%, 95%, 97%, 98%, or 99% homologous or identical to one or more of said nucleotide sequences or a nucleotide sequence encoding an amino acid sequence selected from the group consisting of SEQ ID NOs: 1-3, 6-8. In certain embodiments, nucleotide sequences are at least 90%, 91%, 92%, 93%, 94%, 95%, 96%, 97%, 98%, or 99% homologous or identical to a nucleotide sequence encoding the amino acid sequence of SEQ ID NOs: 4-5, 9-10. The present invention also relates to nucleotide sequences that are at least 80%, 85%, 90%, 95%, 97%, 98%, or 99% identical to one or more of said nucleotide sequences or a nucleotide sequence encoding an amino acid sequence selected from the group consisting of SEQ ID NOs: 11-14.

In one aspect, the present invention relates to a nucleic acid molecule comprising a nucleotide sequence encoding an amino acid sequence selected from SEQ ID NOs: 1-14. A nucleic acid molecule can also comprise any combination of said nucleotide sequences. In one embodiment, a nucleic acid molecule comprises a nucleotide sequence encoding SEQ ID NOs: 3. In another embodiment, a nucleic acid molecule comprises a nucleotide sequence encoding SEQ ID NOs: 8. In one embodiment, a nucleic acid molecule comprises a nucleotide sequence encoding SEQ ID NOs: 1-3. In another embodiment, a nucleic acid molecule comprises a nucleotide sequence encoding SEQ ID NOs: 6-8. In another embodiment, a nucleic acid molecule comprises a nucleotide sequence encoding SEQ ID NOs: 4 or 5. In another embodiment, a nucleic acid molecule comprises a nucleotide sequence encoding SEQ ID NOs: 9 or 10. In another embodiment, a nucleic acid molecule comprises a nucleotide sequence encoding SEQ ID NOs: 4 or 5, and nucleotide sequences encoding SEQ ID NOs: 9 or 10. In another embodiment, a nucleic acid molecule comprises a nucleotide sequence encoding SEQ ID NOs: 11 or 12. In another embodiment, a nucleic acid molecule comprises a nucleotide sequence encoding SEQ ID NOs: 13 or 14. In another embodiment, a nucleic acid molecule comprises a nucleotide sequence encoding SEQ ID NOs: 11 or 12, and nucleotide sequences encoding SEQ ID NOs: 13 or 14.

In one aspect, the present invention relates to a nucleic acid molecule which encodes a heavy chain and comprises a nucleotide sequence that is at least 90%, 91%, 92%, 93%, 94%, 95%, 96%, 97%, 98% or 99% homologous or identical to a sequence selected from the group:

(SEQ ID NO: 15)
CAAGTAACCCTAAAGGAAAGTGGAGGAGGACTTGTCCAACCCGGCGGCAG

TTTAAGACTTAGCTGTGCTGCTTCTGGCTTTACTTTTAGCAACTATGCTA

TGTCGTGGGTGCGTCAAGCGCCAGGAAAGGGCCTAGAATGGGTGAGCGCT

ATCAATAGCGGCGGAAAAAGCACTAACTACGCGGACAGCGTGAAAGGCCG

CTTCACTATAAGTCGGGACAATGCTAAAAACACACTGTACCTCCAGATGA

ACTCCCTAAGAGCTGAGGACACGGCTGTGTACTACTGCGCTGATTATGCG

ACTAACTATGGAGTGCCATACTTCGGAAGCTGGGGCCAGGGAACGACCGT

AACTGTGAGTAGTGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCTTGGGCACCCAG

ACCTACATCTGCAACGTGAATCACAAGCCCAGCAACACCAAGGTGGACAA

GAGAGTTGAGCCCAAATCTTGTGACAAAACTCACACATGCCCACCGTGCC

CAGCACCTGAACTCCTGGGGGGACCGTCAGTCTTCCTCTTCCCCCCAAAA

CCCAAGGACACCCTCATGATCTCCCGGACCCCTGAGGTCACATGCGTGGT

GGTGGACGTGAGCCACGAAGACCCTGAGGTCAAGTTCAACTGGTACGTGG

ACGGCGTGGAGGTGCATAATGCCAAGACAAAGCCGCGGGAGGAGCAGTAC

AACAGCACGTACCGTGTGGTCAGCGTCCTCACCGTCCTGCACCAGGACTG

GCTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACCA

CAGGTGTACACCCTGCCCCCATCCCGGGAGGAGATGACCAAGAACCAGGT

CAGCCTGACCTGCCTGGTCAAAGGCTTCTATCCCAGCGACATCGCCGTGG

AGTGGGAGAGCAATGGGCAGCCGGAGAACAACTACAAGACCACGCCTCCC

GTGCTGGACTCCGACGGCTCCTTCTTCCTCTATAGCAAGCTCACCGTGGA

CAAGAGCAGGTGGCAGCAGGGGAACGTCTTCTCATGCTCCGTGATGCATG

AGGCTCTGCACAACCACTACACGCAGAAAAGCCTCTCCCTGTCCCCGGGT

AAA
or (SEQ ID NO: 16)
CAAGTACAACTACAGGAAAGTGGAGGAGGACTTGTCCAACCCGGCGGCAG

TTTAAGACTTAGCTGTGCTGCTTCTGGCTTTACTTTTAGCAACTATGCTA

TGTCGTGGGTGCGTCAAGCGCCAGGAAAGGGCCTAGAATGGGTGAGCGCT

ATCAATAGCGGCGGAAAAAGCACTAACTACGCGGACAGCGTGAAAGGCCG

CTTCACTATAAGTCGGGACAATGCTAAAAACACACTGTACCTCCAGATGA

ACTCCCTAAGAGCTGAGGACACGGCTGTGTACTACTGCGCTGATTATGCG

ACTAACTATGGAGTGCCATACTTCGGAAGCTGGGGCCAGGGAACGATGGT

AACTGTGAGTAGTGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCTTGGGCACCCAG

ACCTACATCTGCAACGTGAATCACAAGCCCAGCAACACCAAGGTGGACAA

GAGAGTTGAGCCCAAATCTTGTGACAAAACTCACACATGCCCACCGTGCC

CAGCACCTGAACTCCTGGGGGGACCGTCAGTCTTCCTCTTCCCCCCAAAA

CCCAAGGACACCCTCATGATCTCCCGGACCCCTGAGGTCACATGCGTGGT

GGTGGACGTGAGCCACGAAGACCCTGAGGTCAAGTTCAACTGGTACGTGG

ACGGCGTGGAGGTGCATAATGCCAAGACAAAGCCGCGGGAGGAGCAGTAC

AACAGCACGTACCGTGTGGTCAGCGTCCTCACCGTCCTGCACCAGGACTG

GCTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACCA

CAGGTGTACACCCTGCCCCCATCCCGGGAGGAGATGACCAAGAACCAGGT

CAGCCTGACCTGCCTGGTCAAAGGCTTCTATCCCAGCGACATCGCCGTGG

AGTGGGAGAGCAATGGGCAGCCGGAGAACAACTACAAGACCACGCCTCCC

GTGCTGGACTCCGACGGCTCCTTCTTCCTCTATAGCAAGCTCACCGTGGA

CAAGAGCAGGTGGCAGCAGGGGAACGTCTTCTCATGCTCCGTGATGCATG

AGGCTCTGCACAACCACTACACGCAGAAAAGCCTCTCCCTGTCCCCGGGT

AAA.

In one aspect, the present invention relates to a nucleic acid molecule which encodes a heavy chain and comprises a nucleotide sequence selected from the group:

(SEQ ID NO: 15)
CAAGTAACCCTAAAGGAAAGTGGAGGAGGACTTGTCCAACCCGGCGGCAG

TTTAAGACTTAGCTGTGCTGCTTCTGGCTTTACTTTTAGCAACTATGCTA

TGTCGTGGGTGCGTCAAGCGCCAGGAAAGGGCCTAGAATGGGTGAGCGCT

ATCAATAGCGGCGGAAAAAGCACTAACTACGCGGACAGCGTGAAAGGCCG

CTTCACTATAAGTCGGGACAATGCTAAAAACACACTGTACCTCCAGATGA

ACTCCCTAAGAGCTGAGGACACGGCTGTGTACTACTGCGCTGATTATGCG

ACTAACTATGGAGTGCCATACTTCGGAAGCTGGGGCCAGGGAACGACCGT

AACTGTGAGTAGTGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCTTGGGCACCCAG

ACCTACATCTGCAACGTGAATCACAAGCCCAGCAACACCAAGGTGGACAA

GAGAGTTGAGCCCAAATCTTGTGACAAAACTCACACATGCCCACCGTGCC

CAGCACCTGAACTCCTGGGGGGACCGTCAGTCTTCCTCTTCCCCCCAAAA

CCCAAGGACACCCTCATGATCTCCCGGACCCCTGAGGTCACATGCGTGGT

GGTGGACGTGAGCCACGAAGACCCTGAGGTCAAGTTCAACTGGTACGTGG

ACGGCGTGGAGGTGCATAATGCCAAGACAAAGCCGCGGGAGGAGCAGTAC

AACAGCACGTACCGTGTGGTCAGCGTCCTCACCGTCCTGCACCAGGACTG

GCTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACCA

CAGGTGTACACCCTGCCCCCATCCCGGGAGGAGATGACCAAGAACCAGGT

CAGCCTGACCTGCCTGGTCAAAGGCTTCTATCCCAGCGACATCGCCGTGG

AGTGGGAGAGCAATGGGCAGCCGGAGAACAACTACAAGACCACGCCTCCC

GTGCTGGACTCCGACGGCTCCTTCTTCCTCTATAGCAAGCTCACCGTGGA

CAAGAGCAGGTGGCAGCAGGGGAACGTCTTCTCATGCTCCGTGATGCATG

AGGCTCTGCACAACCACTACACGCAGAAAAGCCTCTCCCTGTCCCCGGGT

AAA
or (SEQ ID NO: 16)
CAAGTACAACTACAGGAAAGTGGAGGAGGACTTGTCCAACCCGGCGGCAG

TTTAAGACTTAGCTGTGCTGCTTCTGGCTTTACTTTTAGCAACTATGCTA

TGTCGTGGGTGCGTCAAGCGCCAGGAAAGGGCCTAGAATGGGTGAGCGCT

ATCAATAGCGGCGGAAAAAGCACTAACTACGCGGACAGCGTGAAAGGCCG

CTTCACTATAAGTCGGGACAATGCTAAAAACACACTGTACCTCCAGATGA

ACTCCCTAAGAGCTGAGGACACGGCTGTGTACTACTGCGCTGATTATGCG

ACTAACTATGGAGTGCCATACTTCGGAAGCTGGGGCCAGGGAACGATGGT

AACTGTGAGTAGTGCTAGCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

-continued
ACTCCCTCAGCAGCGTGGTGACCGTGCCCTCCAGCAGCTTGGGCACCCAG

ACCTACATCTGCAACGTGAATCACAAGCCCAGCAACACCAAGGTGGACAA

GAGAGTTGAGCCCAAATCTTGTGACAAAACTCACACATGCCCACCGTGCC

CAGCACCTGAACTCCTGGGGGGACCGTCAGTCTTCCTCTTCCCCCCAAAA

CCCAAGGACACCCTCATGATCTCCCGGACCCCTGAGGTCACATGCGTGGT

GGTGGACGTGAGCCACGAAGACCCTGAGGTCAAGTTCAACTGGTACGTGG

ACGGCGTGGAGGTGCATAATGCCAAGACAAAGCCGCGGGAGGAGCAGTAC

AACAGCACGTACCGTGTGGTCAGCGTCCTCACCGTCCTGCACCAGGACTG

GCTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACCA

CAGGTGTACACCCTGCCCCCATCCCGGGAGGAGATGACCAAGAACCAGGT

CAGCCTGACCTGCCTGGTCAAAGGCTTCTATCCCAGCGACATCGCCGTGG

AGTGGGAGAGCAATGGGCAGCCGGAGAACAACTACAAGACCACGCCTCCC

GTGCTGGACTCCGACGGCTCCTTCTTCCTCTATAGCAAGCTCACCGTGGA

CAAGAGCAGGTGGCAGCAGGGGAACGTCTTCTCATGCTCCGTGATGCATG

AGGCTCTGCACAACCACTACACGCAGAAAAGCCTCTCCCTGTCCCCGGGT

AAA.

In one aspect, the present invention relates to a nucleic acid molecule which encodes a light chain and comprises a nucleotide sequence that is at least 90%, 91%, 92%, 93%, 94%, 95%, 96%, 97%, 98% or 99% homologous or identical to a sequence selected from the group:

(SEQ ID NO: 17)
CAGGCTGGACTGACGCAACCGCCATCTGTGAGTGCGGCTCCAGGACAACG

GGTGACTATAAGCTGCAGCGGAAGCAGAAGCAACATAGGCAGTGGATACG

ACGTACATTGGTACCAACAAGTACCGGGGACGGCTCCGAAACTACTGATA

TTTGACGATAATAATAGACCGAGCGGCGTACCAGACCGTTTTAGCGGAAG

CAAAAGTGGAACGAGTGCCTCTTTAGCCATAACTGGCCTGCAAGCTGAAG

ATGAAGCTGATTATTACTGTCAGAGCTACGACAGCAGTCTGAGTGGACAC

GTAGTGTTTGGAGGAGGAACGAAGCTGACGGTATTACGTACGGTGGCTGC

ACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGT
or (SEQ ID NO: 18)
CAGAGTGTGCTGACGCAACCGCCATCTGTGAGTGCGGCTCCAGGACAACG

GGTGACTATAAGCTGCAGCGGAAGCAGAAGCAACATAGGCAGTGGATACG

ACGTACATTGGTACCAACAACTACCGGGGACGGCTCCGAAACTACTGATA

TACGACGATAATAATAGACCGAGCGGCGTACCAGACCGTTTTAGCGGAAG

CAAAAGTGGAACGAGTGCCTCTTTAGCCATAACTGGCCTGCAAGCTGAAG

ATGAAGCTGATTATTACTGTCAGAGCTACGACAGCAGTCTGAGTGGACAC

GTAGTGTTTGGAGGAGGAACGAAGCTGACGGTATTACGTACGGTGGCTGC

ACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGT.

In one aspect, the present invention relates to a nucleic acid molecule which encodes a light chain and comprises a nucleotide sequence selected from the group:

(SEQ ID NO: 17)
CAGGCTGGACTGACGCAACCGCCATCTGTGAGTGCGGCTCCAGGACAACG

GGTGACTATAAGCTGCAGCGGAAGCAGAAGCAACATAGGCAGTGGATACG

ACGTACATTGGTACCAACAAGTACCGGGGACGGCTCCGAAACTACTGATA

TTTGACGATAATAATAGACCGAGCGGCGTACCAGACCGTTTTAGCGGAAG

CAAAAGTGGAACGAGTGCCTCTTTAGCCATAACTGGCCTGCAAGCTGAAG

ATGAAGCTGATTATTACTGTCAGAGCTACGACAGCAGTCTGAGTGGACAC

GTAGTGTTTGGAGGAGGAACGAAGCTGACGGTATTACGTACGGTGGCTGC

ACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGT
or (SEQ ID NO: 18)
CAGAGTGTGCTGACGCAACCGCCATCTGTGAGTGCGGCTCCAGGACAACG

GGTGACTATAAGCTGCAGCGGAAGCAGAAGCAACATAGGCAGTGGATACG

ACGTACATTGGTACCAACAACTACCGGGGACGGCTCCGAAACTACTGATA

TACGACGATAATAATAGACCGAGCGGCGTACCAGACCGTTTTAGCGGAAG

CAAAAGTGGAACGAGTGCCTCTTTAGCCATAACTGGCCTGCAAGCTGAAG

ATGAAGCTGATTATTACTGTCAGAGCTACGACAGCAGTCTGAGTGGACAC

GTAGTGTTTGGAGGAGGAACGAAGCTGACGGTATTACGTACGGTGGCTGC

ACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

```
GTCACCCATCAGGGCCTGAGCTCGCCCGTCACAAAGAGCTTCAACAGGGG
AGAGTGT.
```

In one aspect, the present invention relates to a nucleic acid molecule comprising any combinations of the above nucleic acid sequences.

In any of the above embodiments, nucleic acid molecules can be isolated.

A nucleic acid molecule of the invention can be isolated from any source that produces anti-IL-5Rα antibody or portion thereof. In certain embodiments, a nucleic acid molecule of the invention can be synthesized, rather than isolated.

In some embodiments, a nucleic acid molecule of the invention can comprise a nucleotide sequence encoding a VH domain from the first or second domain of an antibody of the invention, joined in-frame to a nucleotide sequence encoding a heavy chain constant domain from any source. Similarly, a nucleic acid molecule of the invention can comprise a nucleotide sequence encoding a VL domain from the first or second region of an antibody of the invention, joined in-frame to a nucleotide sequence encoding a light chain constant domain from any source.

In a further aspect of the invention, nucleic acid molecules encoding the variable domain of heavy (VH) and/or light (VL) chains of a first or second binding domain may be "converted" throughout the length of antibody genes. In one embodiment, nucleic acid molecules encoding VH or VL domains are converted to antibody genes throughout the length by virtue of insertion into an expression vector already encoding heavy chain constant (CH) or light chain constant (CL) domains, respectively, such that the VH segment is operatively linked to the CH segment(s) within the vector, and/or the VL segment is operatively linked to the CL segment within the vector. In another embodiment, nucleic acid molecules encoding the VH and/or VL domains are converted into antibody genes throughout the length by virtue of linking, e.g., ligating, a nucleic acid molecule encoding VH and/or VL domains to a nucleic acid molecule encoding CH and/or CL domains using standard molecular biological techniques. Nucleic acid molecules encoding heavy and/or light chains throughout the length may then be expressed from a cell into which they have been introduced.

Nucleic acid molecules may be used to express large quantities of recombinant anti-IL-5Rα antibodies. Nucleic acid molecules may also be used to produce human antibodies, humanized antibodies, chimeric antibodies, bispecific antibodies, single chain antibodies, immunoadhesins, diabodies, mutated antibodies and antibody derivatives, as described herein.

Vector

In another aspect, the present invention relates to a vector suitable for the expression of any of nucleotide sequences described herein.

The present invention relates to vectors comprising nucleic acid molecules that encode any of the amino acid sequences of anti-IL-5Rα antibodies or portions thereof (e.g., heavy and/or light chain sequences of a first binding domain and/or heavy and/or light chain sequences of a second binding domain), as described herein. The invention further provides vectors comprising nucleic acid molecules encoding fusion proteins, modified antibodies, antibody fragments.

In another embodiment, nucleic acid molecules and vectors may be used to make mutated anti-IL-5Rα antibodies. Antibodies may be mutated in the variable domains of the heavy and/or light chains of a first binding domain and/or heavy and/or light chains of a second binding domain, e.g., to alter a binding property of anti-IL-5Rα antibodies. For example, a mutation may be made in one or more CDRs to increase or decrease the $K_D$ of antibodies, to increase or decrease $k_{off}$, or to alter the binding specificity of an antibody with respect to IL-5Rα. In another embodiment, one or more mutations are made at an amino acid residue in the first or second binding domain of anti-IL-5Rα antibody of the invention. Such mutations may be made in the CDR or framework region of a variable domain, or in a constant domain. In a preferred embodiment, mutations are made in a variable domain. In another embodiment, one or more mutations are made at an amino acid residue that is known to be changed compared to the germinal line in the CDR or framework region of a variable domain of an antibody of the invention.

In some embodiments, the anti-IL-5Rα antibodies of the invention are expressed by inserting a DNA partially or fully encoding the sequence of a first or second binding domain (e.g., light and heavy chain sequences where a binding domain comprises light and heavy chain sequences), obtained as described above, in expression vectors such that the genes are operatively linked to necessary expression control sequences, such as transcriptional and translational control sequences. Expression vectors include plasmids, retroviruses, adenoviruses, adeno-associated viruses (AAV), plant viruses, such as cauliflower mosaic virus, tobacco mosaic virus, cosmids, YACs, EBV derived episomes, and the like. DNA molecules may be ligated into a vector such that transcriptional and translational control sequences within the vector serve their intended function of regulating the transcription and translation of the DNA. An expression vector and expression control sequences may be chosen to be compatible with the expression host cell used. DNA molecules partially or fully encoding the sequences of first and second binding domains (for example, heavy and light chain sequences where a binding domain comprises a heavy and light chain sequence) can be introduced into individual vectors. In one embodiment, any combination of said DNA molecules is introduced into the same expression vector. DNA molecules can be introduced into an expression vector by standard methods (e.g., ligation of complementary restriction sites on an antibody gene fragment and vector, or blunt end ligation if no restriction sites are present).

A suitable vector is one that encodes functionally complete human CH or CL immunoglobulin sequences, with appropriate restriction site engineering so that any VH or VL sequence can easily be inserted and expressed, as described above. HC- and LC-encoding genes in such vectors may contain intron sequences that results in enhanced overall antibody protein yields by stabilizing the corresponding mRNA. The intron sequences are flanked by splice donor and splice acceptor sites, which determine where RNA splicing will occur. Location of intron sequences can be either in variable or constant regions of antibody chains, or in both variable and constant regions when multiple introns are used. Polyadenylation and transcription termination may occur at a native chromosomal site downstream of coding regions. A recombinant expression vector can also encode a signal peptide that facilitates secretion of an antibody chain from a host cell. An antibody chain gene may be cloned into a vector such that the signal peptide is linked in-frame to the amino terminus of an immunoglobulin chain. The signal peptide can be an immunoglobulin signal peptide or a heterologous signal peptide (i.e., a signal peptide from a non-immunoglobulin protein).

In addition to antibody chain genes, the recombinant vector expression of the invention can carry regulatory sequences that control the expression of antibody chain genes in a host cell. It will be understood by those skilled in the art that the design of an expression vector, including the selection of regulatory sequences, may depend on such factors as the choice of a host cell to be transformed, the level of expression of a desired protein, and so forth. Preferred control sequences for an expression host cell in mammals include viral elements that ensure high levels of protein expression in mammalian cells, such as promoters and/or enhancers derived from a retroviral LTR, cytomegalovirus (CMV) (such as a CMV promoter/enhancer), simian virus 40 (SV40) (such as a SV40 promoter/enhancer), adenovirus, (e.g., the major late promoter adenovirus (AdMLP)), polyomavirus and strong mammalian promoters such as native immunoglobulin promoter or actin promoter. For further description of viral control elements and sequences thereof, see, e.g., U.S. Pat. Nos. 5,168,062, 4,510,245 and 4,968,615. Methods for expressing binding molecules, such as antibodies in plants, including a description of promoters and vectors, as well as transformation of plants are known in the art. See, e.g., U.S. Pat. No. 6,517,529. Methods for expressing polypeptides in bacterial cells or fungal cells, e.g., yeast cells, are also well known in the art.

In addition to antibody chain genes and regulatory sequences, the recombinant expression vectors of the invention may carry additional sequences, such as sequences that regulate replication of a vector in host cells (e.g., origins of replication) and selectable marker genes. The selectable marker gene facilitates the selection of host cells into which a vector has been introduced (see e.g., U.S. Pat. Nos. 4,399,216, 4,634,665 and 5,179,017). For example, typically the selectable marker gene confers resistance to medicinal agents, such as G418, hygromycin or methotrexate, on a host cell into which a vector has been introduced. For example, selectable marker genes include a dihydrofolate reductase (DHFR) gene (for use in dhfr-host cells during methotrexate selection/amplification), a neo gene (for G418 selection), and a glutamate synthetase gene.

The term "expression control sequence" as used herein is intended to refer to polynucleotide sequences that are necessary to affect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include the promoter of ribosome binding site, and transcription termination sequences; in eukaryotes, typically, such control sequences include promoters and transcription termination sequences. The term "control sequences" is intended to include at least all components, the presence of which is essential for expression and processing, and can also include additional components, the presence of which is advantageous, for example, leader sequences and fusion partner sequences.

Host Cells

A further aspect of the invention relates to methods for producing anti-IL-5Rα antibodies of the invention. One embodiment of the invention relates to a method for producing antibodies as defined herein, comprising introducing/preparing a recombinant host cell capable of expressing antibodies, cultivating said host cells under conditions suitable for expression/production of the antibodies, and isolating the obtained antibody. Anti-IL-5Rα antibodies produced by such expression in such recombinant host cells are referred to herein as "recombinant anti-IL-5Rα antibodies." The invention also relates to the progeny of cells from such host cells and anti-IL-5Rα antibodies obtained analogously.

Nucleic acid molecules encoding anti-IL-5Rα antibodies of the invention and vectors comprising these nucleic acid molecules can be used for transfection of a suitable mammalian or cell thereof, plant or cell thereof, bacterial or yeast host cell. Transformation can be by any known technique for introducing polynucleotides into a host-cell. Methods for introduction of heterologous polynucleotides into mammalian cells are well known in the art and include dextran-mediated transfection, cationic polymer-nucleic acid complex transfection, calcium phosphate precipitation, polybrene-mediated transfection, protoplast fusion, encapsulation of the polynucleotide(s) in liposomes, and direct microinjection of DNA into nuclei. In addition, nucleic acid molecules may be introduced into mammalian cells by viral vectors. Methods for transfecting cells are well known in the art. See, e.g., U.S. Pat. Nos. 4,399,216, 4,912,040, 4,740,461 and 4,959,455. Methods for transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines used as hosts for transformation are well known in the art and include a plurality of immortalized cell lines available. These include, e.g., Chinese hamster ovary (CHO) cells, NSO cells, SP2 cells, HEK-293T cells, FreeStyle 293 cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines are selected by determining which cell lines have high expression levels and provide for necessary characteristics of protein produced. Other cell lines that may be used are insect cell lines, such as Sf9 or Sf21 cells. When recombinant expression vectors encoding anti-IL-5R antibodies are introduced into mammalian host cells, the antibodies are produced by culturing the host cells for a period of time sufficient to allow for expression of the antibodies in host cells or, more preferably, secretion of the antibodies into the culture medium in which the host cells are grown. Anti-IL-5Rα antibodies can be reconstituted from the culture medium using standard protein purification techniques. Plant host cells include, e.g., *Nicotiana, Arabidopsis*, duckweed, corn, wheat, potato, etc. Bacterial host cells include *Escherichia* and *Streptomyces* species. Yeast host cells include *Schizosaccharomyces pombe, Saccharomyces cerevisiae* and *Pichia pastoris*.

Furthermore, level of production of anti-IL-5Rα antibodies of the invention from production cell lines can be enhanced using a number of known techniques. For example, the glutamine synthetase gene expression system (the GS system) is a common approach for enhancing expression under certain conditions. The GS system is discussed in whole or part in connection with EP Nos. 0216846, 0256055, 0323997 and 0338841.

It is likely that anti-IL-5Rα antibodies expressed by different cell lines or in transgenic animals will have a different glycosylation profile as compared to each other. However, all anti-IL-5Rα antibodies encoded by the nucleic acid molecules described herein, or comprising the amino acid sequences provided herein are part of the present invention, regardless of the glycosylation of the binding molecules, and, in general, regardless of the presence or absence of post-translational modifications.

Preparation of Antibodies

The invention also relates to methods and processes for producing anti-IL-5Rα antibodies and antigen-binding fragment thereof.

Monoclonal Antibodies

Monoclonal antibodies may be prepared using the hybridoma method first described by Kohler, et al. Nature 256, 1975, p. 495, or may be prepared using recombinant DNA methods (U.S. Pat. No. 4,816,567).

In a hybridoma method, a mouse, or other appropriate host animal, such as a hamster, is immunized according to the above method to elicit lymphocytes that produce or are capable of producing antibodies that will specifically bind to protein used for immunization. According to another embodiment, lymphocytes can be produced by in vitro immunization. After immunization, the lymphocytes are fused with a myeloma cell line using a suitable fusing agent, such as polyethylene glycol, to produce a hybridoma cell.

The hybridoma cells, produced in the above manner, may be cultured in a suitable culture medium that preferably contains one or more substances that inhibit the growth or survival of the unfused parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), i.e. substances which prevent the growth of HGPRT-deficient cells.

Preferred cells, used as component for myeloma cell fusion, are those that fuse efficiently, support stable high level production of antibodies by the selected antibody-producing cells, and are sensitive to a medium where the unfused parental cells are selected. Preferred myeloma cell lines are murine myeloma lines, such as those derived from MOPC-21 and MPC-11 mouse tumors available from the Salk Institute Cell Distribution Center, San Diego, California, USA, and SP-2 or X63-Ag8-653 cells available from the American Type Culture Collection, Rockville, Maryland, USA. Human myeloma and mouse-human heteromyeloma cell lines also have been described for the production of monoclonal antibodies (Kozbor, J. Immunol., 133, 1984, p. 3001).

Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods. Suitable culture media for this purpose include, for example, D-MEM or RPMI-1640 medium. In addition, the hybridoma cells may be grown in vivo as ascites tumors in an animal, e.g. by intraperitoneal (i.p.) injection of the cells into mice.

The monoclonal antibodies secreted by the subclones can be separated from the culture medium, ascites fluid, or serum by conventional antibody purification techniques such as, for example, affinity chromatography (e.g., using protein A- or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of specific binding to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not produce antibody protein without being transfected, to obtain the synthesis of monoclonal antibodies in the recombinant host cells.

In a further embodiment, monoclonal antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992), as well as combinatorial infection and in vivo recombination as a strategy for constructing very large phage libraries (Waterhouse et al., Nucl. Acids. Res. 21:2265-2266 (1993). Thus, these techniques are viable alternatives to traditional monoclonal antibody hybridoma techniques for isolation of monoclonal antibodies.

The DNA that encodes the antibody may be modified, for example, so as to produce chimeric or fusion antibody polypeptides, for example, by substituting heavy chain and light chain (CH and CL) constant region sequences for the homologous murine sequences (U.S. Pat. No. 4,816,567 and Morrison, et al., Proc. Natl. Acad. Sci. USA: 81:6851 (1984), or by covalently fusing the immunoglobulin coding sequence with all or part of the coding sequence of a non-immunoglobulin polypeptide (heterologous polypeptide). The non-immunoglobulin polypeptide sequences can be substituted for the constant regions of an antibody, or they can be substituted for the variable domains of one antigen-binding center of an antibody to create a chimeric bivalent antibody comprising one antigen-binding site having specificity for an antigen and another antigen-binding site having specificity for a different antigen.

Humanized Antibodies

Methods for producing "humanized" non-human animal antibodies are well known in the art. Preferably, a humanized antibody has one or more integral amino acid residues introduced into it from a source which is non-human. These non-human amino acid residues are often referred to as "import" residues because they are typically taken from an "import" variable region. Humanization can be essentially performed following the method of Winter and co-authors (Jones et al., Nature, 321:522-525 (1986) by substituting hypervariable region sequences for the corresponding sequences of a human antibody. Accordingly, such "humanized" antibodies are chimeric antibodies (U.S. Pat. No. 4,816,567) in which a region, which is substantially less than an intact human variable region, has been substituted by the corresponding sequence from a non-human species. In practice, humanized antibodies are typically human antibodies in which some hypervariable region residues and possibly some FR residues are substituted by residues from analogous regions in rodent antibodies.

The choice of human variable regions, both light and heavy, to be used in producing the humanized antibodies is very important to reduce antigenicity and HAMA response (human anti-mouse antibody) when the antibody is intended for human therapeutic use. According to the so-called "best-fit" method, the sequence of the variable region of a rodent antibody is screened against the entire library of known human variable domain sequences. The human V domain sequence which is closest to that of the rodent is identified and the human framework region (FR) within it is selected, which is suitable for use in the humanized antibody (Sims et al., J. Immunol. 151:2296 (1993). Another method uses a particular framework region derived from the consensus sequence of a particular subgroup of light or heavy chains of all human antibodies. The same framework may be used for several different humanized antibodies (Carter et al., Proc. Natl. Acad. Sci. USA: 89:4285 (1992).

It is also important that antibodies be humanized with retention of high binding affinity for the antigen and other significant biological properties. To this end, according to a preferred method, humanized antibodies are prepared by analysis of the parental sequences and various humanized products using conceptual three-dimensional models of the parental and humanized sequences. Three-dimensional immunoglobulin models are commonly available and are familiar to those skilled in the art. Computer programs are available which illustrate and display possible three-dimensional conformational structures of selected candidate immunoglobulin sequences. Inspection of these images permits analysis of the possible role of the residues in the functioning of the candidate immunoglobulin sequence, i.e., the analysis of residues that influence the ability of the candidate immunoglobulin to bind to antigen. In this fashion, FR residues can be selected and combined with recipient and import sequences to achieve the desired antibody characteristics, such as increased affinity for the target antigen(s). In general, the hypervariable region residues are directly and most substantially involved in influencing antigen binding.

The humanized antibody may be an antibody fragment, such as Fab, which is optionally conjugated with one or more cytotoxic agent(s) in order to generate an immunoconjugate. Alternatively, the humanized antibody may be a full-length antibody, such as a full-length IgG1 antibody.

Human Antibodies and Methodology Based on Phage Display Library

As an alternative to humanization, human antibodies can be generated. For example, it is now possible to produce transgenic animals (e.g., mice) that are capable, after immunization, of producing a full range of human antibodies without endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice results in the production of human antibodies after antigen challenge (U.S. Pat. Nos. 5,545,806, 5,569,825, 5,591,669 (all of GenPharm); 5545807; and WO 97/17852).

Alternatively, phage display technology (McCafferty et al., Nature, 348:552-553 (1990) can be used to produce human antibodies and antibody fragments in vitro from immunoglobulin variable (V) region gene repertoire from immunized donor bodies. According to this technique, antibody V-region genes are cloned in-frame with either a major or minor coat protein gene of a filamentous bacteriophage, such as M13 or fd, and displayed as functional antibody fragments on the surface of a phage particle. Because the filamentous particle contains a single-stranded DNA copy of the phage genome, selections based on the functional properties of the antibody also result in selection of a gene encoding an antibody exhibiting said properties. Thus, the phage mimics some of B-cell properties. Phage display can be performed in a variety of formats. Several sources of V-gene segments can be used for phage display. Clackson et al., Nature, 352:624-628 (1991) isolated various arrays of anti-oxazolone antibodies from a small random combinatorial library of V genes derived from the spleen of immunized mice. A repertoire of V genes from unimmunized human donors can be constructed and antibodies against a diverse array of antigens (including self-antigens) can be isolated essentially following the techniques described by Marks et al., J. Mol. Biol. 222:581-597 (1991).

As described above, human antibodies may also be generated by in vitro activated B cells (see U.S. Pat. Nos. 5,567,610 and 5,229,275).

Antibody Fragments

In certain circumstances, it is advisable to use antibody fragments rather than whole antibodies. The small size of the fragments contributes to rapid clearance thereof and may contribute to better penetration into dense tumors.

Various techniques have been developed for the production of antibody fragments. Traditionally, these fragments were derived via proteolytic digestion of intact antibodies. However, these fragments can now be produced directly by recombinant host cells. Fab, Fv and ScFv antibody fragments can be expressed in and secreted from E. coli, thus allowing to facilitate the production of large amounts of these fragments. Antibody fragments can be isolated from the antibody phage libraries described above. According to another embodiment, Fab'-SH fragments can be directly isolated from E. coli and chemically coupled to form $F(ab')_2$ fragments (Carter et al., Bio/Technology 10:163-167 (1992). According to another approach, $F(ab')_2$ fragments can be isolated directly from recombinant host cell culture. Fab and $F(ab')_2$ fragment with increased in vivo half-life retaining epitope binding receptor residues are described in U.S. Pat. No. 5,869,046. Other techniques for the production of antibody fragments will be apparent to those skilled in the art. In other embodiments, the antibody of choice is a single chain Fv fragment (scFv) (see WO 93/16185; U.S. Pat. Nos. 5,571,894 and 5,587,458). Fv and scFv are the only species with intact binding sites that are devoid of constant regions; as a result, they are suitable for reduced nonspecific binding during in vivo use. scFv fusion proteins may be constructed to yield fusion of an effector protein at either N- or C-terminus of an scFv. The antibody fragment may also be a "linear antibody", e.g., as described in U.S. Pat. No. 5,641,870. Such linear antibody fragments may be monospecific or bispecific.

Bispecific Antibodies

Bispecific antibodies are antibodies that have binding specificity for at least two different epitopes. For example, bispecific antibodies may bind to two different epitopes of anti-IL-5Rα antibody protein. Other bispecific antibodies may combine an anti-IL-5Rα antibody binding site in combination with a binding site for another protein. Bispecific antibodies can be prepared as full length antibodies or antibody fragments (e.g., $F(ab')_2$ of bispecific antibodies).

Methods for producing bispecific antibodies are known in the art. Traditional production of full length bispecific antibodies is based on the co-expression of two immunoglobulin heavy chain/light chain pairs, where the two chains have different specificities. Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography in several steps, is rather cumbersome, and the product yield is low. Similar procedures are disclosed in WO 93/08829.

According to a different approach, antibody variable domains with the desired binding specificity (antigen-binding sites of an antibody) are fused to immunoglobulin constant domain sequences. Preferably, the fusion is made with an Ig heavy chain constant region, comprising at least a portion of the hinge, $C_H2$, and $C_H3$ regions. Preferably, the first heavy chain constant region ($C_H1$) containing the site necessary for light chain binding is present in at least one of the fusions. DNAs encoding the immunoglobulin heavy chain fusions and, if desired, the immunoglobulin light chain, are inserted into various expression vectors, and are co-transfected into a suitable host cell. This provides for greater flexibility in selecting mutual proportions of the three polypeptide fragments in embodiments when unequal ratios of the three polypeptide chains are used in the construction to provide optimum yields. It is, however, possible to insert the coding sequences into two or all three polypeptide chains in a single expression vector when the expression of at least two polypeptide chains in equal ratios results in high yields, or when the ratios have no significant affect.

In a preferred embodiment of this approach, the bispecific antibodies are a hybrid immunoglobulin heavy chain providing for a first binding specificity in a first arm, and a hybrid immunoglobulin heavy chain/light chain pair (providing for a second binding specificity) in a second arm. It was found that this asymmetric structure facilitates the separation of the desired bispecific molecule from unwanted immunoglobulin chain combinations, as the presence of an immunoglobulin light chain in only one half of the bispecific molecule facilitates separation. This approach is disclosed in WO 94/04690. For more details in regard to producing bispecific antibodies see, for example, Suresh et al., Methods in Enzymology 121:210 (1986).

According to another approach described in U.S. Pat. No. 5,731,168, the interface between a pair of antibody molecules can be constructed to maximize the percentage of heterodimers which are obtained from recombinant cell culture. The preferred interface comprises at least a portion of the $C_H3$ region. According to this method, one or more small amino acids with side chains from the interface of the first antibody molecule are replaced with larger side chains (e.g., tyrosine or tryptophan). Compensatory "cavities" of identical or similar size to the large side chain(s) are created on the interface of the second antibody molecule by replacing amino acids containing large side chains with amino acids containing smaller side chains (e.g., alanine or threonine). This provides a mechanism for increasing the yield of heterodimer as compared to other unwanted end-products.

Bispecific antibodies include cross-linked or "heteroconjugate" antibodies. For example, one of the antibodies in the heteroconjugate can be coupled to avidin, and the other to biotin. Such antibodies can, for example, be used to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with various cross-linking techniques.

Techniques for producing bispecific antibodies from antibody fragments have also been described in the literature. For example, bispecific antibodies can be prepared using chemical binding. Brennan et al., Science 229:81 (1985) have described a procedure, according to which intact antibodies are proteolytically cleaved to produce F(ab')$_2$. These fragments are reduced in the presence of the dithiol complexing agent, such as sodium arsenite, to stabilize vicinal dithiols and prevent formation of intermolecular disulfide bonds. The Fab' fragments produced are then converted to thionitrobenzoate (TNB) derivative. One of the Fab'-TNB derivatives is then reconverted to Fab'-thiol by reduction with mercaptoethylamine and is mixed with an equimolar amount of another Fab'-TNB derivative to form the bispecific antibody. The bispecific antibodies produced can be used as agents for selective immobilization of enzymes.

Recent progress has facilitated the direct recovery of Fab'-SH fragments from $E.$ $coli$, which can be chemically coupled to produce bispecific antibodies. Shalaby et al., J. Exp. Med. 175:217-225 (1992) describe the production of F(ab')$_2$ of a fully humanized bispecific antibody molecule. Each Fab' was separately secreted from $E.$ $coli$ and subjected to direct chemical coupling in vitro to form the bispecific antibody.

Various techniques for producing and isolating bispecific antibody fragments directly from recombinant cell culture have also been described. For example, bispecific antibodies have been produced using leucine zippers (Kostelny et al, J. Immunol. 148(5):1547-1553 (1992). The leucine zipper peptides from Fos and Jun proteins were linked to the Fab' of two different antibodies by gene fusion. Antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) is an alternative mechanism for producing bispecific antibody fragments. The fragments comprise a VH region connected to a VL region by a linker which is too short to allow pairing between the two domains on the same chain. Accordingly, the VH and VL regions of one fragment have to pair with the complementary VL and VH regions of another fragment, thereby forming two antigen-binding sites. Another strategy for producing bispecific antibody fragments using single-chain (Fv)-(sFv) dimers has also been described (see Gruber et al., J. Immunol., 152: 5368 (1994).

The invention also provides antibodies with more than two valences. For example, trispecific or tetraspecific antibodies can be produced.

Polyvalent Antibodies

A polyvalent antibody may be internalized (and/or catabolized) by a cell expressing an antigen, to which the antibody binds, faster than a bivalent antibody. The proposed herein antibodies can be polyvalent antibodies (which are other than those of the IgM class) with three or more antigen binding sites (e.g. tetravalent antibodies), which can be readily produced by recombinant expression of nucleic acid encoding the polypeptide chains of the antibody. The polyvalent antibody can comprise a dimerization domain and three or more antigen binding sites. The preferred dimerization domain comprises (or consists of) an Fc fragment or a hinge region. In this scenario, the antibody will comprise an Fc fragment and three or more antigen binding sites at N-terminus to the Fc fragment. The preferred polyvalent antibody herein comprises (or consists of) 3 to about 8, but preferably 4, antigen binding sites. The polyvalent antibody comprises at least one polypeptide chain (and preferably two polypeptide chains), wherein the polypeptide chain(s) comprise two or more variable regions. For example, the polypeptide chain(s) may comprise VD1-(X1)n-VD2-(X2)n-Fc, wherein VD1 refers to a first variable region, VD2 refers to a second variable region, Fc refers to one polypeptide chain of an Fc fragment, X1 and X2 refer to an amino acid or polypeptide, and n is 0 or 1. For example, the polypeptide chain(s) may comprise the following chain: VH-CH 1-flexible linker-VH-CH1-Fc fragment; or VH-CH1-VH-CH1-Fc fragment. The polyvalent antibody herein preferably further comprises at least 2 (and preferably 4) light chain variable region polypeptides. The polyvalent antibody herein may, for example, comprise from about 2 to about 8 light chain variable region polypeptides. In the context of the present invention, the light chain variable region polypeptides comprise a light chain variable region and, optionally, further comprise a CL region.

Pharmaceutical Compositions

In another aspect, the invention provides a pharmaceutical composition comprising an IL-5Rα-specific antibody as an active ingredient (or as the only active ingredient). The pharmaceutical composition may include at least one antibody that is specific for IL-5Rα and/or one or more additional binding molecules (e.g., antibodies) that target one or more of the corresponding surface receptors, as described herein. In some embodiments, the compositions are intended to improve, prevent, or treat disorders that may be resulted from the interaction of IL-5 and cellular receptor thereof.

"Pharmaceutical composition" means a composition comprising an anti-IL-5Rα antibody of the present invention and at least one of components selected from the group consisting of pharmaceutically acceptable and pharmacologically compatible excipients, such as fillers, solvents, diluents, carriers, auxiliary, distributing agents, delivery agents, preservatives, stabilizers, emulsifiers, suspending agents, thickeners, prolonged delivery controllers, the choice and proportions of which depend on the type and route of administration and dosage. Pharmaceutical compositions of the present invention and methods of preparation thereof will be undoubtedly apparent to those skilled in the art. The pharmaceutical compositions should preferably be manufactured in compliance with the GMP (Good Manufacturing Practice) requirements. The composition may comprise a buffer composition, tonicity agents, stabilizers and solubilizers. Prolonged action of composition may be achieved by agents slowing down absorption of active pharmaceutical ingredient, for example, aluminum monostearate and gelatin. Examples of suitable carriers, solvents, diluents and delivery agents include water, ethanol, polyalcohols and their mixtures, oils, and organic esters for injections.

"Medicament (drug)"—is a compound or a mixture of compounds as a pharmaceutical composition in the form of tablets, capsules, powders, lyophilisates, injections, infusion, ointments and other ready forms intended for restoration, improvement or modification of physiological functions in humans and animals, and for treatment and preventing of diseases, for diagnostics, anesthesia, contraception, cosmetology and others. Any method for administering peptides, proteins or antibodies which is accepted in the art may be suitably employed for an anti-IL-5Rα antibody of the invention.

The term "pharmaceutically acceptable" refers to one or more compatible liquid or solid components that are suitable for administration in a mammal, preferably a human.

The term "excipient" is used herein to describe any ingredient other than the above ingredients of the invention. These are substances of inorganic or organic nature which are used in the pharmaceutical manufacturing in order to give drug products the necessary physicochemical properties.

As used herein, "buffer", "buffer composition", "buffering agent" refers to a solution, which is capable of resisting changes in pH by the action of its acid-base conjugate components, and which allows the anti-IL-5Rα antibody drug to resist changes in pH. Generally, the pharmaceutical composition preferably has a pH in the range from 4.0 to 8.0. Examples of buffers used include, but are not limited to, acetate, phosphate, citrate, histidine, succinate, etc. buffer solutions.

The terms "tonic agent", "osmolyte" or "osmotic agent", as used herein, refer to an excipient that can increase the osmotic pressure of a liquid antibody formulation. "Isotonic" drug is a drug that has an osmotic pressure equivalent to that of human blood. Isotonic drugs typically have an osmotic pressure from about 250 to 350 mOsm/kg. Isotonic agents used include, but are not limited to, polyols, saccharides and sucrose, amino acids, metal salts, for example, sodium chloride, etc.

"Stabilizer" refers to an excipient or a mixture of two or more excipients that provide the physical and/or chemical stability of the active agent. Stabilizers include amino acids, for example, but are not limited to, arginine, histidine, glycine, lysine, glutamine, proline; surfactants, for example, but are not limited to, polysorbate 20 (trade name: Tween 20), polysorbate 80 (trade name: Tween 80), polyethylene-polypropylene glycol and copolymers thereof (trade names: Poloxamer, Pluronic, sodium dodecyl sulfate (SDS); antioxidants, for example, but are not limited to, methionine, acetylcysteine, ascorbic acid, monothioglycerol, sulfurous acid salts, etc.; chelating agents, for example, but are not limited to, ethylenediaminetetraacetic acid (EDTA), diethylenetriaminepentaacetic acid (DTPA), sodium citrate, etc.

A pharmaceutical composition is "stable" if the active agent retains physical stability and/or chemical stability and/or biological activity thereof during the specified shelf life at storage temperature, for example, of 2-8° C. Preferably, the active agent retains both physical and chemical stability, as well as biological activity. Storage period is adjusted based on the results of stability test in accelerated or natural aging conditions.

A pharmaceutical composition of the invention can be manufactured, packaged, or widely sold in the form of a single unit dose or a plurality of single unit doses in the form of a ready formulation. The term "single unit dose", as used herein, refers to discrete quantity of a pharmaceutical composition containing a predetermined quantity of an active ingredient. The quantity of the active ingredient typically equals the dose of the active ingredient to be administered in a subject, or a convenient portion of such dose, for example, half or a third of such dose.

The pharmaceutical compositions according to the present invention are typically suitable for parenteral administration as sterile formulations intended for administration in a human body through the breach in skin or mucosal barriers, bypassing the gastrointestinal tract by virtue of injection, infusion and implantation. For example, parenteral administration includes, inter alia, subcutaneous, intraperitoneal, intramuscular, intrasternal, intravenous, intraarterial, intrathecal, intraventricular, intraurethral, intracranial, intrasynovial, transdermal injection or infusions; and kidney dialytic infusion techniques. Regional perfusion is also provided. Preferred embodiments include intravenous and subcutaneous routes. Any method for administering peptides or proteins accepted in the art may be suitably employed for an anti-IL-5Rα antibody of the invention.

Injectable formulations may be prepared, packaged, or sold, without limitation, in unit dosage form, such as in ampoules, vials, in plastic containers, pre-filled syringes, autoinjection devices. Formulations for parenteral administration include, inter alia, suspensions, solutions, emulsions in oily or aqueous bases, pastes, and the like.

In another embodiment, the invention provides a composition for parenteral administration comprising a pharmaceutical composition which is provided in dry (i.e. powder or granular) form for reconstitution with a suitable base (e.g., sterile pyrogen-free water) prior to administration. Such formulation may be prepared by, for example, lyophilisation process, which is known in the art as freeze drying, and which involves freezing a product followed by removal of solvent from frozen material.

The anti-IL-5Rα antibody of the invention can also be administered intranasally or by inhalation, either alone, as a mixture with a suitable pharmaceutically acceptable excipient from an inhaler, such as a pressurised aerosol container, pump, spray, atomiser, or nebuliser, wherein a suitable propellant is used or not used, or as nasal drops, or spray.

Dosage forms for parenteral administration may be formulated to be immediate or modified release. Modified release formulations include delayed-, sustained-, pulsed-, controlled-, targeted and programmed release.

Therapeutic Use of Anti-IL-5Rα Antibody of the Invention

In one aspect, an anti-IL-5Rα antibody of the invention is useful in the treatment of disorders that are associated with IL-5 activity.

In one aspect, an anti-IL-5Rα antibody of the invention is useful in the treatment of a disease or disorder, wherein a disease or disorder is selected from the group: asthma, for example, eosinophilic asthma (atopic asthma), for example, severe eosinophilic asthma (atopic asthma); COPD (chronic obstructive pulmonary disease); Churg-Strauss syndrome; eosinophilic esophagitis; eosinophilic gastroenteritis or hypereosinophilic syndrome.

In one aspect, the subject of treatment, or patient, is a mammal, preferably a human subject. Said subject may be either male or female, of any age.

As used herein, the terms "co-administration", "co-administered" and "in combination with", referring to anti-IL-5Rα antibodies and one or more other therapeutic agents, are expected to mean, refer to or include the following:

1) simultaneous administration of such combination of an anti-IL-5Rα antibody of the invention and therapeutic agent to a patient in need of treatment, when such components are formulated together into a single dosage form which releases said components at substantially the same time to said patient, 2) substantially simultaneous administration of such combination of an anti-IL-5Rα antibody of the invention and therapeutic agent to a patient in need of treatment, when such components are formulated apart from each other into separate dosage forms which are taken at substantially the same time by said patient, whereupon said components are released at substantially the same time to said patient, 3) sequential administration of such combination of an anti-IL-5Rα antibody of the invention and therapeutic agent to a patient in need of treatment, when such components are formulated apart from each other into separate dosage forms which are taken at consecutive times by said patient with a significant time interval between each administration, whereupon said components are released at substantially different times to said patient; and 4) sequential administration of such combination of an anti-IL-5Rα antibody of the invention and therapeutic agent to a patient in need of treatment, when such components are formulated together into a single dosage form which releases said components in a controlled manner, whereupon they are concurrently, consecutively, or jointly released at the same and/or different times to said patient, where each portion may be administered by either the same or different routes.

The anti-IL-5Rα antibodies of the invention can be administered without further therapeutic treatment, i.e., as an independent therapy. Furthermore, treatment by the anti-IL-5Rα antibodies of the invention may comprise at least one additional therapeutic treatment (combination therapy). In some embodiments, the anti-IL-5Rα antibody may be administered with or in combination with a different medicament/autoimmune disease drug.

In treatment of the above autoimmune diseases or related autoimmune conditions, the anti-IL-5Rα antibodies proposed herein in combination with a different therapeutic agent may be administered in a patient, using a multidrug regimen. The anti-IL-5Rα antibody can be administered simultaneously, sequentially, sequentially or alternately with an immunosuppressor, or after showing resistance to a different therapy. The same or lower immunosuppressor dosages may be used, as compared to those used in the art. Many factors, including type of disease to be treated and patient's medical record, should be taken into account when choosing a preferred immunosuppressor.

As used herein, the term "therapeutic agent" used in add-on therapy refers to substances directed to suppress or mask a patient's immune system, for example, to small molecules, antibodies or steroid hormones, such as corticosteroids. Such agents can be substances that inhibit cytokine production, down-regulate or suppress self-antigen expression or mask major histocompatibility complex (MHC) antigens. Examples of such agents include steroids, such as glucocorticoids, for example prednisone, methylprednisolone and dexamethasone; 2-amino-6-aryl-5-substituted pyrimidines (see U.S. Pat. No. 4,665,077), azathioprine (or cyclophosphamide, in case of adverse reaction to azathioprine); bromocryptine; glutaraldehyde (which masks MHC antigens, as described in U.S. Pat. No. 4,120,649); anti-idiotypic antibodies against MHC antigens and MHC fragments; cyclosporine A; cytokine and cytokine receptor antagonists including interferon-gamma, -beta, or -alpha antibodies; anti-tumor necrosis factor antibodies; anti-interleukine-2 antibodies and anti-IL-2 receptor antibodies; anti-L3T4 antibodies, heterologous anti-lymphocyte globulin, pan-T antibodies, preferably anti-CD3 or anti-CD4/CD4a antibodies; soluble peptide containing a LFA-3 binding domain (WO 90/08187, published Jun. 26, 1990); streptokinase; TGF-p; streptodomase; host DNA/RNA; FK506; RS-61443; deoxyspergualin; rapamycin; T cell receptor (U.S. Pat. No. 5,114,721); T cell receptor fragments (Offner et al, Science 251:430-432 (1991); WO 90/11294; and WO 91/01133); and T cell receptor antibodies (EP 340109), such as T10B9.

It is meant that the anti-IL-5Rα antibodies of the invention may be used in the methods of treatment as described above, may be used in the treatment as described above, and/or may be used in the manufacture of a medication for treatment as described above.

Doses and Routes of Administration

The anti-IL-5Rα antibody of the invention will be administered in an amount that is effective in treatment of the condition in question, i.e. in doses and during the periods of time required to achieve the desired result. A therapeutically effective amount may vary according to factors such as the specific condition to be treated, age, sex, and weight of a patient, and whether the anti-IL-5Rα antibodies are administered alone or in combination with one or more additional anti-autoimmune or anti-inflammatory treatment techniques.

Dosage regimens may be adjusted to provide the optimum response. For example, a single bolus may be administered, several divided doses may be administered over time or the dose may be proportionally reduced or increased as indicated by the exigencies of the therapeutic situation. It is especially advantageous to formulate parenteral compositions in a unit dosage form for ease of administration and uniformity of dosage. A unit dosage form as used herein is intended to refer to physically discrete units suited as unitary dosages for patients/subjects to be treated; each unit contains a predetermined quantity of active compound calculated to produce the desired therapeutic effect in association with the desired pharmaceutical carrier. Specification for the unit dosage forms of the invention is typically dictated by and directly dependent on (a) the unique characteristics of a chemotherapeutic agent and particular therapeutic or prophylactic effect to be achieved, and (b) the limitations inherent in the art of compounding such an active compound for the treatment of sensitivity in the subjects.

Thus, a skilled artisan would appreciate, based upon the disclosure provided herein, that the doses and dosage regimen are adjusted in accordance with methods well-known in the therapeutic arts. That is, the maximum tolerable dose can be readily established, and the effective amount providing a detectable therapeutic effect to a patient may also be determined, as can the temporal requirements for administering each agent to provide a detectable therapeutic effect to a patient. Thus, while certain dose and administration regimens are exemplified herein, these examples in no way limit the doses and administration regimen that may be provided to a patient in practicing the embodiments of the invention.

It is to be noted that dosage values may vary with the type and severity of the condition to be alleviated, and may include single or multiple doses. Furthermore, it is to be understood that for any particular subject, specific dosage regimens should be adjusted over time according to the individual need and the judgment of a medical professional administering or supervising the administration of the compositions, and that dosage ranges set forth herein are exemplary only and are not intended to limit the scope or practice of the claimed compositions. Further, the dosage regimen with the compositions of this invention may be based on a variety of factors, including the type of disease, the age, weight, sex, medical condition of the patient, the severity of the condition, the route of administration, and the particular anti-IL-5Rα antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the person skilled in the art. Methods for determining appropriate dosages and regimens are well-known in the art and would be understood by a skilled artisan once provided the ideas disclosed herein.

Examples of suitable administration methods are provided above.

It is believed that a suitable dose of an anti-IL-5Rα antibody of the invention will be in the range of 0.1-200 mg/kg, preferably 0.1-100 mg/kg, including about 0.5-50 mg/kg, for example about 1-20 mg/kg. The anti-IL-5Rα antibody may be administered, e.g., in a dose of at least 0.25 mg/kg, such as at least 0.5 mg/kg, including at least 1 mg/kg, e.g., at least 1, 5 mg/kg, such as at least 2 mg/kg, e.g., at least 3 mg/kg, including at least 4 mg/kg, e.g., at least 5 mg/kg; and for example up to a maximum of 50 mg/kg, including up to a maximum of 30 mg/kg, e.g., up to a maximum of 20 mg/kg, including up to a maximum of 15 mg/kg. The administration will typically be repeated in appropriate time intervals, such as once a week, once every two weeks, once every three weeks or once every four weeks, and for as long as deemed appropriate by a responsible physician, who may, in some cases, increase or reduce the dose if necessary.

Article of Manufacture (Products) and Kits

According to another embodiment, the present invention provides an article of manufacture comprising products intended to be used for treatment of autoimmune diseases and related conditions, such as asthma, for example, eosinophilic asthma (atopic asthma), for example, severe eosinophilic asthma (atopic asthma); COPD (chronic obstructive pulmonary disease); Churg-Strauss syndrome; eosinophilic esophagitis, eosinophilic gastroenteritis, or hypereosinophilic syndrome. The product is a container with a label and package insert, which can be in a blister and/or package. Suitable containers include, e.g., vials, ampoules, syringes, etc. The containers may be made of various materials such as glass or polymer material. The container comprises a composition which is effective for treating a certain condition, and can have a sterile access port. At least one active ingredient in the composition is an anti-IL-5Rα antibody according to the invention. The label and package insert indicates that the drug is intended to be used to treat a certain condition. The label and/or package insert additionally contain instructions for administering the antibody composition in a patient, including indications, frequency, dose, route of administration, contraindications and/or precautions for such therapeutic products. In one embodiment, the package insert indicates that the composition is intended to be used for treatment of asthma, for example, eosinophilic asthma (atopic asthma), for example, severe eosinophilic asthma (atopic asthma); COPD (chronic obstructive pulmonary disease); Churg-Strauss syndrome; eosinophilic esophagitis; eosinophilic gastroenteritis, or hypereosinophilic syndrome.

Furthermore, an article of manufacture may comprise, without limitation, other products necessary for commercial purposes or necessary for a consumer, such as solvents, diluents, filters, needles and syringes.

The invention also relates to kits that can be used for various purposes, for example, to purify or immunoprecipitate IL-5Rα from cells, to isolate IL-5Rα-carrying cells. A kit for isolation and purification of anti-IL-5Rα antibodies or IL-5Rα-carrying cells. A kit may comprise an anti-IL-5Rα antibody associated with granules (e.g., sepharose granules or magnetic particles). A kit contains a container, a label and a package insert.

Diagnostic Use and Compositions

The anti-IL-5Rα antibodies of the invention are also used in diagnostic processes (e.g., in vitro, ex vivo). For example, the anti-IL-5Rα antibody can be used for detecting or measuring the level of IL-5Rα in samples obtained from a patient (e.g., tissue sample or a sample of body fluid, such as an inflammatory exudate, blood, serum, intestinal fluid, saliva or urine). Suitable methods for detection and measurement include immunoassays, such as flow cytometry, enzyme-linked immunosorbent assay (ELISA), chemiluminescent assay, radioimmunoassay, and immunohistology. The invention further includes kits, for example, diagnostic kits comprising an anti-IL-5Rα antibody described herein.

EXAMPLES

The following examples are provided for better understanding of the invention. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended embodiments.

Materials and General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991). Amino acids of antibody chains are numbered and referred to according to EU numbering (Edelman, G. M., et al., Proc. Natl. Acad. Sci. Natl. Acad. Sci. USA 63 (1969) 78-85; Kabat, E. A., et al., Sequences of Proteins of Immunological Interest, 5th ed., Public Health Service, National Institutes of Health, Bethesda, MD, (1991).

Recombinant DNA Techniques

Standard methods were used to manipulate DNA as described in Sambrook, J. et al, Molecular cloning: A laboratory manual; Cold Spring Harbor Laboratory Press, Cold Spring Harbor, New York, 1989. The molecular biological reagents were used according to the manufacturer's instructions.

Gene Synthesis

Desired gene segments were prepared from oligonucleotides made by chemical synthesis. The gene segments of 300-4000 kb long, which were flanked by singular restriction sites, were assembled by annealing and ligation of oligonucleotides including PCR amplification and subsequently cloned via the indicated restriction sites. The DNA sequences of the subcloned gene fragments were confirmed by DNA sequencing.

DNA Sequence Determination

DNA sequences were determined by Sanger sequencing. DNA and Protein Sequence Analysis and Sequence Data Management The Infomax's Vector NT1 Advance suite version 8.0 was used for sequence creation, mapping, analysis, annotation and illustration.

Expression Vectors

For the expression of the described antibodies and antigens, variants of expression plasmids intended for expression in prokaryotic cells (*E. coli*), transient expression in eukaryotic cells (e.g., in CHO cells) were applied. Beside the antibody expression cassette the vectors contained: an origin of replication which allows replication of said plasmid in *E. coli*, genes which confer resistance in *E. coli* to various antibiotics (e.g., to ampicillin and kanamycin).

The fusion genes comprising the described antibody chains as described below were generated by PCR and/or gene synthesis and assembled with known recombinant methods and techniques by connection of the according nucleic acid segments, e.g., using unique restriction sites in the corresponding vectors. The subcloned nucleic acid sequences were verified by DNA sequencing. For transient transfections, larger quantities of the plasmids were prepared by plasmid preparation from transformed *E. coli* cultures.

Example 1

Production of Recombinant Antigens and Antibodies in Suspension Mammalian Cell Culture A sequence encoding the extracellular domain of human and animal IL-5Rα was cloned into the plasmid pEE with EPEA, FC and H6F tags to produce protein (FIG. 1, 2, 3) at SalI/NotI restriction sites. The required quantities of the plasmid were produced in *E. Coli* cells and purified using Qiagen kit.

Antigens were produced in the cells of established cell line obtained from Chinese hamster ovary cells (CHO-T cell line), antibodies were produced in CHO, according to published protocols [Cytotechnology (2012) 64:613-622]. Suspension culture was conducted in flasks on orbital shaker using serum-free media from HyCell TransFx-C supplemented with 8 mM L-glutamine and 1 g/l pluronic 68. For transient expression, cells at a concentration of 2-2,2*$10^6$ c/ml were transfected by means of linear polyethyleneimine (PEI MAX, Polysciences). DNA/PEI ratio was 1:3/1:10. In 5-7 days after transfection, cell culture was centrifuged under 2000 g for 20 min and filtered through 0.22 μm filter. Target proteins were isolated from culture liquid by affine HPLC.

Recombinant protein comprising an EPEA-tag (glutamic acid-proline-glutamic acid-alanine) at the C-terminus of protein was isolated using sorbent CaptureSelect C-tag Affinity Matrix. The culture fluid was passed through a chromatographic column pre-filled with 5 ml of C-tag sorbent, the column was then washed with 25 ml of PBS to remove any non-specifically binding components. The bound antigen was eluted under mild conditions using 20 mM Tris, 2 M $MgCl_2$ (pH 7.0-7.4). Protein was then dialyzed into PBS (pH 7.4) using a semi permeable dialysis membrane, filtered (0.22 μm), transferred into tubes and stored at −70° C.

Recombinant Fc proteins were isolated using sorbent 5 ml HiTrap rProtein A Sepharose FF (GE Healthcare). Column was equilibrated and then washed with 5 volumes of PBS to remove non-specific bound components. Bound antigen was eluted with 0.1 M glycine buffer (pH 3). The principal protein elution peak was collected and brought to neutral pH with 1 M Tris buffer (pH 8). All stages were conducted under 110 cm/h flow rate. Protein was then dialyzed into PBS (pH 7.4) using SnakeSkin Dialysis Tubing technique, filtered (0.22 μm), transferred into tubes and stored at −70° C.

Recombinant His-tagged proteins were isolated using a Ni-NTA (QIAGEN) column, sorbent was washed three times with equilibration buffer (50 mM $NaH_2PO_4$, 300 mM NaCl, 10 mM imidazole (pH 8.0). The culture liquid pH was adjusted to 8.0, $NiCl_2$ was added to a final concentration of 1 mM. Sorbent was transferred into the culture fluid, incubated for 2 hour at 4° C. with stirring, and washed with ten column volumes of buffer (50 mM $NaH_2PO_4$, 300 mM NaCl, 10 mM imidazole), washed with twenty column volumes (50 mM Na$_2$HPO4, 1 M NaCl, 20 mM imidazole), washed with ten volumes of PBS (pH 7.4), eluted with 50 mM NaH$_2$PO$_4$ 300 mM NaCl, 250 mM imidazole (pH 8.0). Protein solution was converted into PBS (pH 7.4) and frozen at −70° C.

Figure 4:
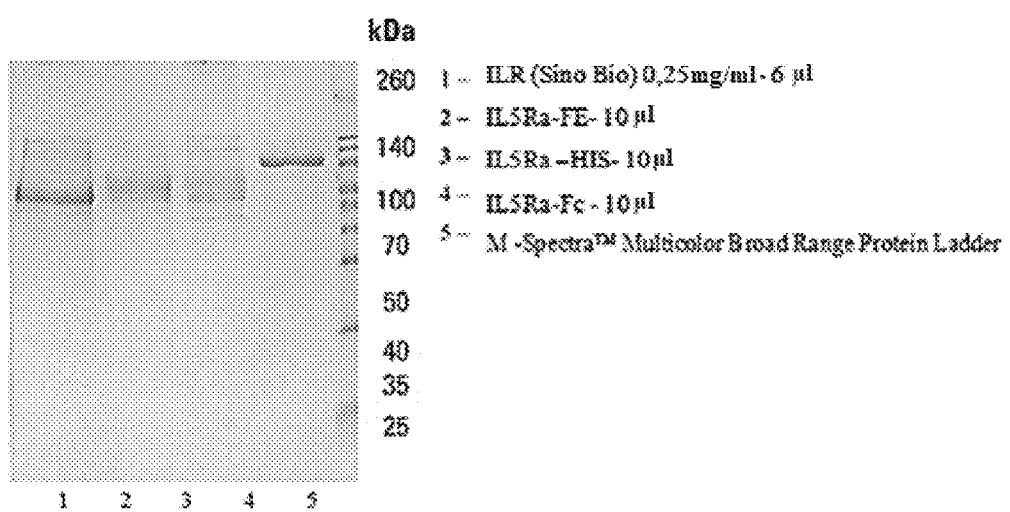
FIG. 4. Electrophoregram antigens under reducing conditions 10% SDS-PAGE
Figure 5:
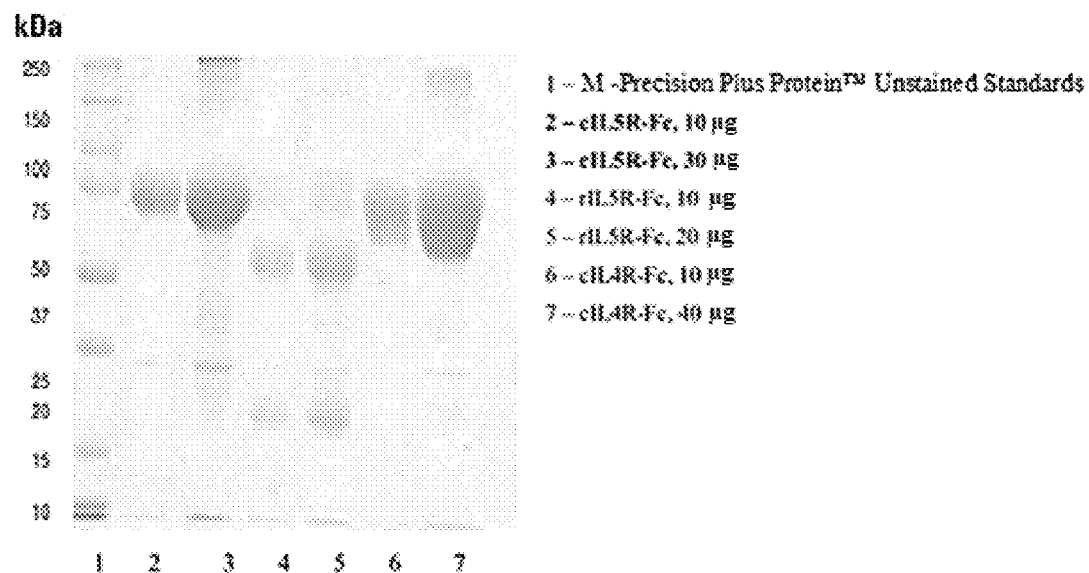
FIG. 5. Electrophoregram of antigens under reducing conditions 10% SDS-PAGE

Purity of protein solution obtained was evaluated by reducing and non-reducing SDS-PAGE (FIG. 4,5,6).

Example 2

Engineering of a Naive Human Fab Phage Library MeganLib™

Total RNA of B lymphocytes from blood samples of more than one thousand individual human donors was isolated using RNeasy Mini Kit (QIAGEN) according to the suggested protocol. RNA concentration assay was performed using Nanovue kit (GE Healthcare); the quality of isolated RNA was tested by means of 1.5% agarose gel electrophoresis.

Reverse transcription reaction was conducted using MMLV RT kit (Evrogen) according to the recommended protocol with MMuLV reverse transcriptase and random hexamer oligonucleotides as primers.

Reverse transcription products were used as a matrix in a two-stage polymerase chain reaction to obtain the genes of variable domains flanked with restriction sites; reaction was performed using oligonucleotide kit according to protocols by [J Biol Chem. 1999 Jun. 25; 274(26): 18218-30].

Figure 3:
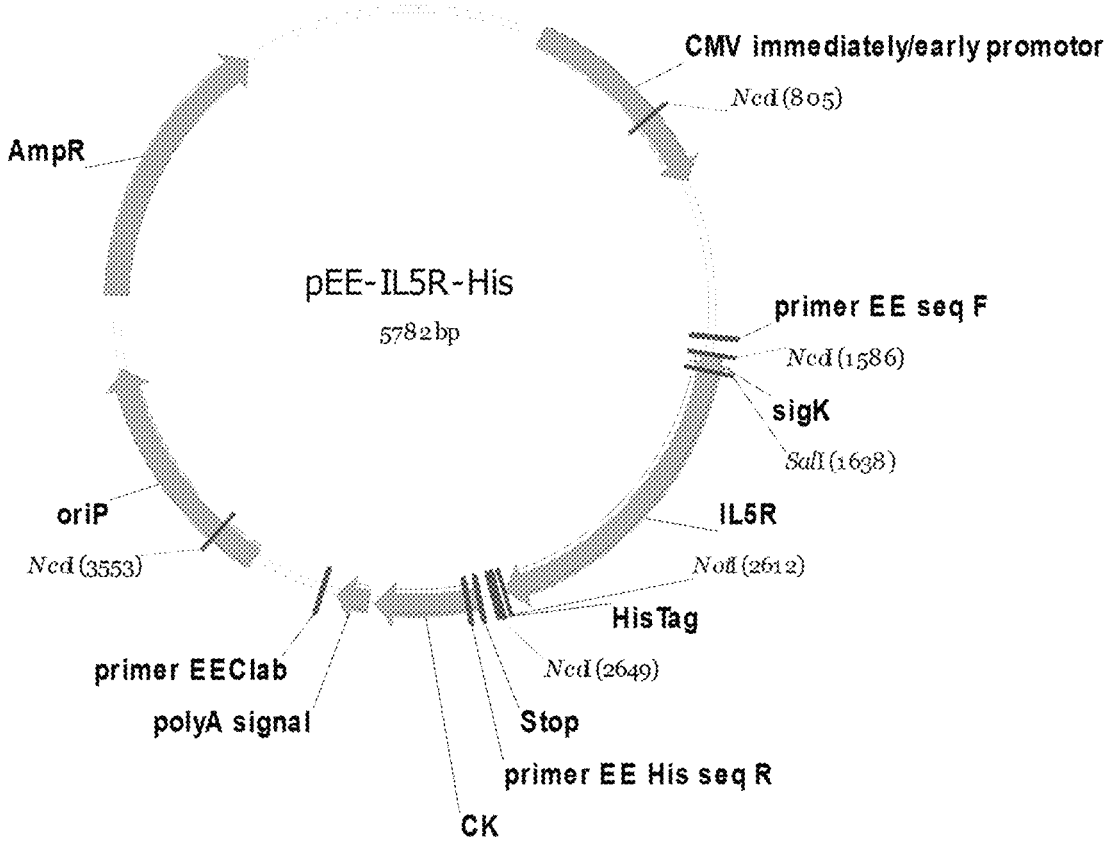
FIG. 3. Plasmid map for transient generation of antigens with His-b tag.

Obtained DNA preparation VL-CK-VH (FIG. 3) was treated with NheI/Eco91I restriction endonucleases and ligated into the original phagemid pH5 (FIG. 4). Ligation products were transformed into SS320 *E. coli* electrocompetent cells prepared in accordance with protocols [Methods Enzymol. 2000; 328: 333-63.]. Repertoire of combinatorial Fab phage display library MeganLib™ was $10^{11}$ transformants. Preparations of Fab phage libraries were prepared in accordance with the earlier described procedure [J Mol Biol. 1991 Dec. 5; 222(3): 581-97].

Example 3

Production of Human Anti-IL-5Rα Fabs by Phage Display

Specific anti-IL-5Rα human phage Fabs were obtained from the combinatorial Fab phage display library MeganLib™. Biopanning was performed on human IL-5Rα by phage display [Nat Biotechnol. 1996 March; 14(3):309-14; J Mol Biol. 1991 Dec. 5; 222(3): 581-97], but using magnetic beads and KingFisher Flex device, due to the fact that this technique allows performing up to 96 different schemes and variants simultaneously.

Human biotinylated IL-5Rα antigen (Fc, EPEA) was purposely immobilized onto the surface of streptavidin magnetic beads (NEB) at a concentration of 10 μg/ml for the first round, 2 μg/ml for the second round, 0.4 and 0.2 μg/ml for the third round and fourth round, respectively. Antigen was incubated with the beads for 1 hour at room temperature on a rotator. The beads were then washed with PBS (pH 7.4), bead surface was blocked with a solution of 2% fat-free milk or 1% BSA in PBS (pH 7.4) for 1 hour. Human phage library MeganLib™ was diluted at a concentration of $2*10^{13}$ phage particles/ml in PBS (pH 7.4) with 2% fat-free milk and non-target antigen containing a target antigen tag, and preselected by magnetic beads containing no antigen on the surface, in order to remove nonspecific binding phages. IL-5Rα-coated magnetic beads were then incubated with MeganLib™ for 1-2 hours at room temperature.

Unbound phages were removed by several cycles of washing of magnetic beads with a solution of PBS (pH 7.4) with 0.1% Tween 20. Number of washing cycles was increased from round to round (3 washing cycles in the first round, 9 washing cycles in the second round, and 15 washing cycles in the fourth round). Phages which bound to antigen on the surface of magnetic beads were eluted from beads with 100 mM Gly-HCl solution (pH 2.2) for 15 min while stirring, the solution was then neutralized with 1M Tris-HCl (pH 7.6). *E. coli* TG1 bacteria were infected with phages, grown in culture medium and used in the next selection cycle. After three or four rounds, phagemid DNA was isolated from *E. coli* TG1 culture according to the manufacturer's (Qiagen) protocol. Polyclonal phage enzyme immunoassay (ELISA) was used for enrichment of library against target antigens and assessment of presence of non-specifically binding phage particles.

Example 4

ELISA of Polyclonal Phage Against Specific and Nonspecific Antigens

Target antigen IL-5Rα-Fc and non-target one with Fc-fusion protein were immobilized on high absorption plates (Greiner-Bio) in order to perform ELISA. Protein was added at a concentration of 1 μg/ml and 5 μg/ml, respectively, in 0.1 M NaHCO$_3$ (pH 9.0) and titrated with an increment of 2 to 7 dilutions, sealed plates were then incubated overnight at 4° C. All subsequent steps were conducted in accordance with the standard ELISA protocol using a high-performance automated Tecan Freedom EVO 200-based robotic platform (Tecan). To block non-specific binding, blocking buffer comprising 2% fat-free milk or 1% BSA in PBS (pH 7.4) was added to plate wells. Plates were incubated for 1 h at room temperature. After several washing cycles with phosphate-saline buffer containing Tween 20 (PBST), 50 μl/well of polyclonal phage under test was added. After washing, each well was coated (50 μl/well) with anti-M13 HRP-conjugated secondary antibody (Pierce-ThermoScientific) in PBST (1:7500). After 50 minute incubation at room temperature, plates were three times washed with PBST. Colorimetric signal was obtained by adding substrate solution (H$_2$O$_2$-0.02% and TMB in CH$_3$COONa pH 5.5) for 10 minutes; color development was then blocked by adding 1% sulfuric acid (20 μl). Color signal was measured at 450 nm using a suitable Tecan-Sunrise plate reader (Tecan).

Figure 10:
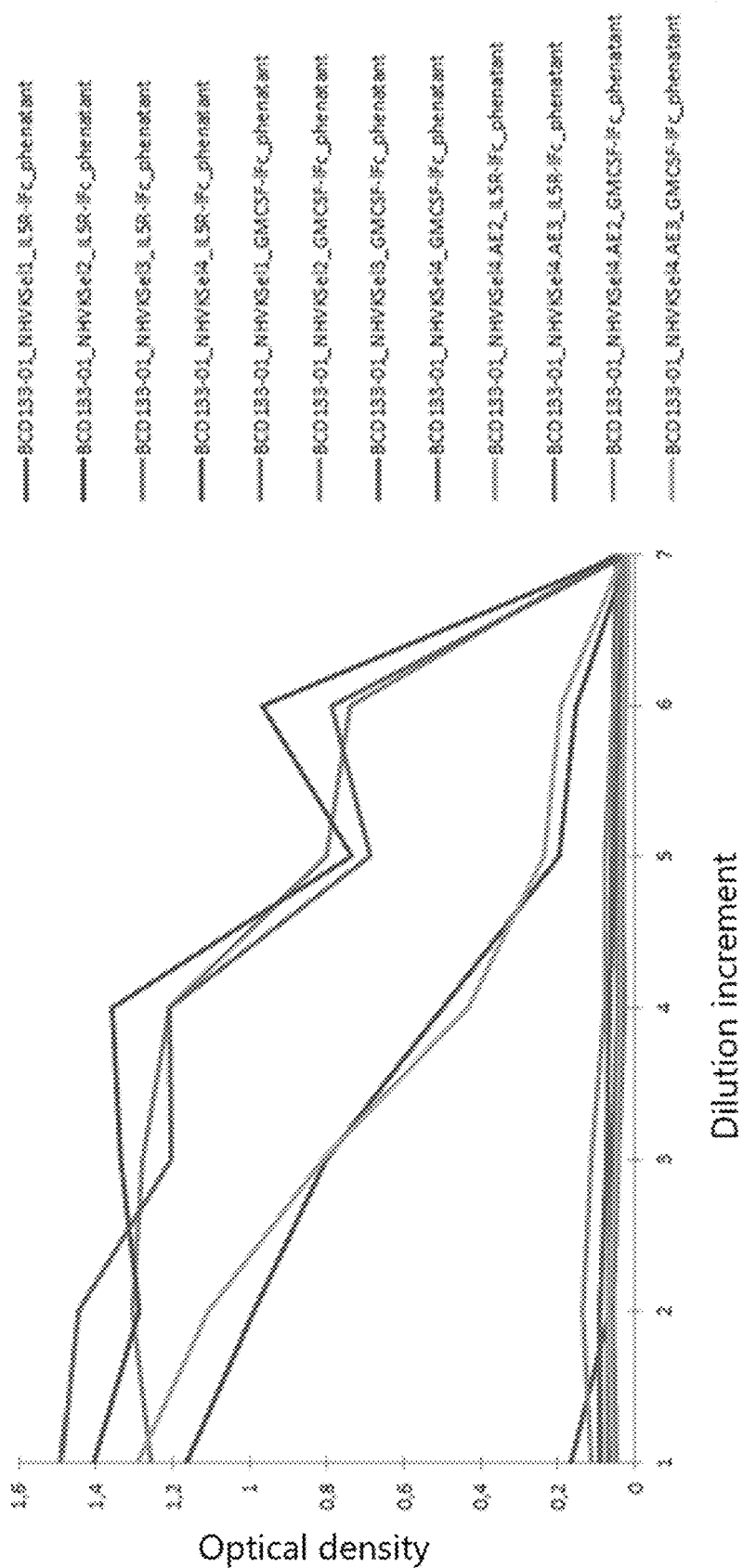
FIG. 10. Immunoenzyme analysis of polyclonal phage of post-selection libraries for specific and nonspecific antigens.

ELISA of polyclonal phage preparation showed significant enrichment after third and fourth rounds of selection on target antigen (FIG. 10). Libraries were selected for recloning and further screening, in which the signal was observed to exceed 5 times at minimal dilution of phage libraries to non-homologous control antigens.

Example 5

Recloning of Genes of Antibody Variable Domains into Expression Plasmid

Figure 9:
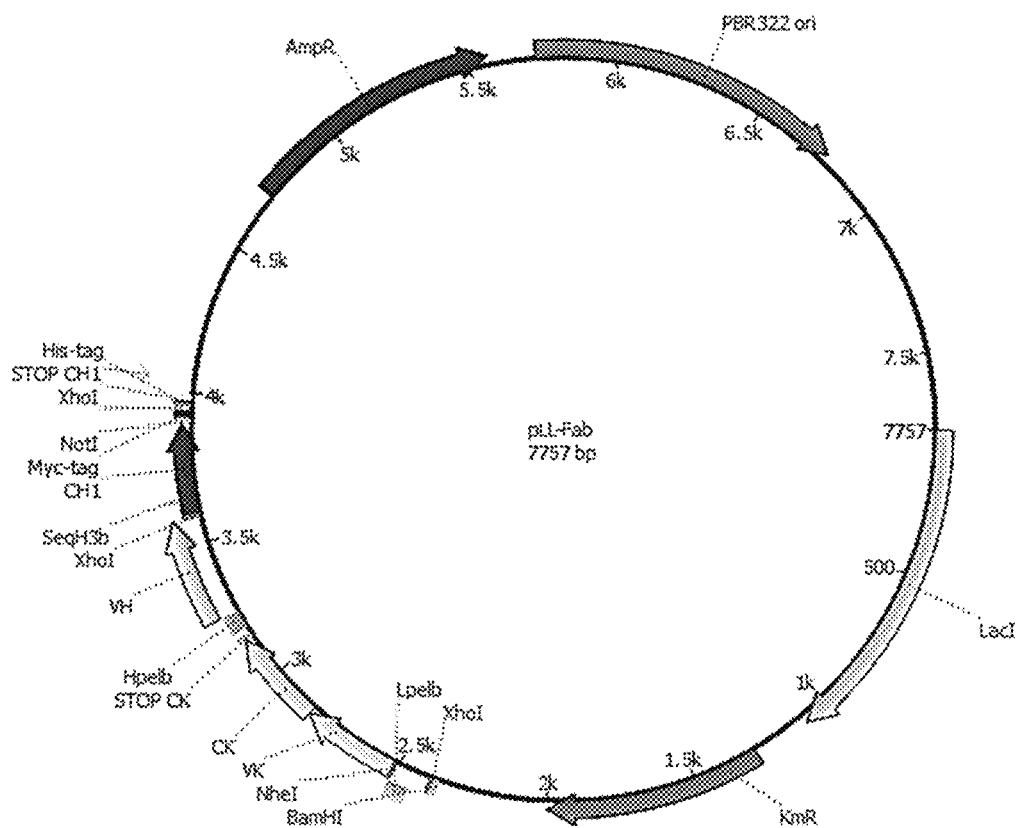
FIG. 9. Expression plasmid map for Fab production.

Recloning of genes of antibody variable domains into an expression plasmid (FIG. 9) from phagemid vector after successful rounds of selection was carried out according to a standard protocol using restriction ligation technique.

Subsequently, expression vectors comprising antibody fragments were transformed into *E. coli* BL21-Gold strain for comparative analysis of affinity of variable antibody fragments from display libraries to antigen by ELISA using Mabnext Flow Chart platform.

Example 6

Selection of High-Affinity Clones from Post-Selection Libraries, which Specifically Bind Human IL-5Rα

Fabs were produced according to the standard technique: E. coli BL21-Gold bacterial cells were transformed with expression vectors containing Fab genes, and subsequent addition of inducer triggered transcription of lac operon, thereby, when culturing resulting transformants, causing expression of Fabs which were exported into periplasmic space. ELISA was then performed to verify binding of Fab to substrate-immobilized IL-5Rα-EPEA antigen at a concentration of 0.2 µg/ml on plates (medium binding from Greiner bio one) in 0.1 M NaHCO$_3$ (pH 9.0) (antigen was immobilized overnight at 4° C.). Fab Benralizumab (Medimmune) sequence inserted into expression plasmid pLL was used as a positive control. All further steps were conducted at room temperature in accordance with the standard ELISA protocol using a high-performance automated platform based on robotic systems Genetix Qpix2xt (Molecular Devices) and Tecan Freedom EVO 200 (Tecan). Washing was performed after each step, with 300 µl/well 1× PBST in three replications. Non-specific binding sites on the plate were blocked with 1% fat-free milk in 1×PBS, analyte (60 µl/well of E. coli supernatants) represented by E. coli supernatants was added after washing. Immune complexes were detected using peroxidase-conjugated goat anti-Fab antibodies (Pierce-ThermoScientific) (1:7500). Substrate-chromogenic mixture was stained by adding 50 µl of substrate solution (H$_2$O$_2$-0.02% and TMB in CH$_3$COONa (pH 5.5)) for 15 minutes. 25 µl of 1% H$_2$SO$_4$ were used to stop the reaction. Color signal was measured at 450 nm using a suitable Tecan-Sunrise plate reader (Tecan). Antibody binding was proportional to the signal produced. Clones in which a colour signal exceeded the signal from control antibody were tested by ELISA against non-specific binding.

Example 7

Analysis of Non-Specific Binding of Selected Fabs to Different Antigens

ELISA was also employed to analyze non-specific binding of Fabs in question to different antigens. Analysis was performed as described above, but IL6R-Fc, PCSK9-VG-FE in 0.1 M NaHCO$_3$ (pH 9.0) were used as antigens for immobilization (antigen was immobilized overnight at 4° C.). IL-5Rα-FE, IL-5Rα-Fc were used as specific binding control (antigen was immobilized overnight at 4° C.). All further stages were conducted in accordance with the standard ELISA protocol with a high-performance automated platform based on robotic systems such as Genetix Qpix2xt (Molecular Devices) and Tecan Freedom EVO 200 (Tecan). Clones in which colour signal did not exceed the control signal were tested by competitive ELISA to identify Fabs blocking receptor-ligand interaction.

Example 8

Selection of High-Affinity Fabs that Block Interaction of IL-5Rα with Ligand IL-5

Competitive ELISA was used to test previously selected anti-human specific Fabs against the ability to block interaction of IL-5Rα with the ligand IL-5 (Sino Biological). Fab with published sequence, Benralizumab (Medimmune), was used as a positive control.

50 µl/well IL-5 (1 µg/ml solution in NaHCO$_3$, pH 9.0) was immobilized in ELISA well plates (medium binding, Greiner bio one) and incubated overnight at 4° C. All further stages were performed in accordance with standard ELISA protocols at room temperature using a high-performance automated platform based on robotic systems Genetix Qpix2xt (Molecular Devices) and Tecan Freedom EVO 200 (Tecan). Non-specific binding was blocked by adding a blocking buffer (200 µl 1% fat-free milk in PBS).

In parallel, cell supernatant comprising the test Fab and IL-5Rα (at a final concentration of 1 µg/ml in PBST) was mixed at a 1:1 ratio in non-absorbent plates, incubated for 45 minutes at room temperature.

After washing from blocking buffer, preincubated mixture was transferred to the plate. All further steps were similar to those described in example 6. Clones that showed blocking at the level of control Fab Benralizumab were noted as positive and used in further assays.

Genes of variable domains of positive clones were sequenced according to standard protocols on Applied Biosystems 3130 Genetic Analyzer (Applied Biosystems) and analyzed.

Example 9

Selection of High-Affinity Fabs by Dissociation Rate

Koff screening was performed using Pall Forte Bio Octet Red 96. Anti-FABCH1 biosensors were rehydrated for 30 min in a working buffer comprising 10 mM PBS (pH 7.2-7.4), 0.1% Tween 20 and 0.1% BSA. Working buffer was added to test samples of E. coli supernatants up to 10% final concentration. Anti-FABCH1 biosensors were then steeped into E. coli supernatants containing Fabs of candidate antibodies and incubated for 12 hours at 4° C. Sensors with surface immobilized Fabs were transferred to wells with a working buffer, where a baseline was recorded (60 sec). The sensors were then transferred to wells with an analyte solution (IL-5Rα-Fc, 30 µg/ml) to achieve antigen-antibody association (300 sec). The sensors were then returned into wells containing working buffer for further dissociation (600 sec). Used sensors were subject to regeneration after each test: they were three times placed into regenerating buffer (10 mM Gly-HCl, pH 1.7) and then used in further experiments. The curves obtained were analyzed using Octet Data Analysis (version 9.0) according to the standard procedure with 1:1 Local interaction model.

Example 10

Preparation of Full-Length Antibodies

Figure 6:
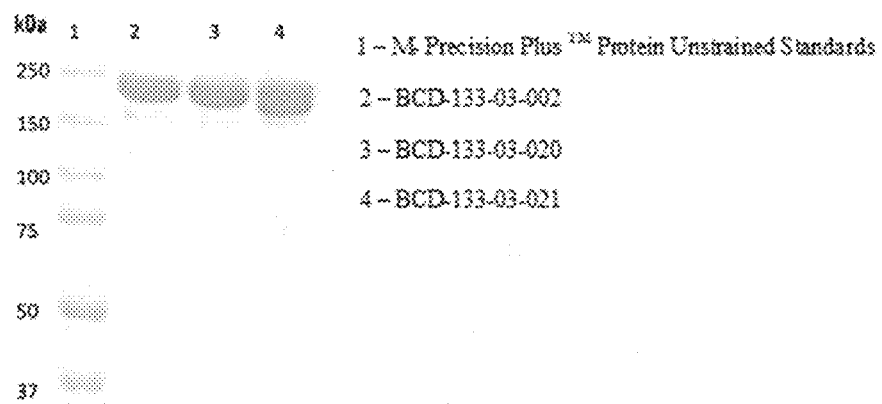
FIG. 6. Electrophoregram antigens in and antibodies in non-reducing conditions (7.5% SDS-PAGE).
Figure 7:
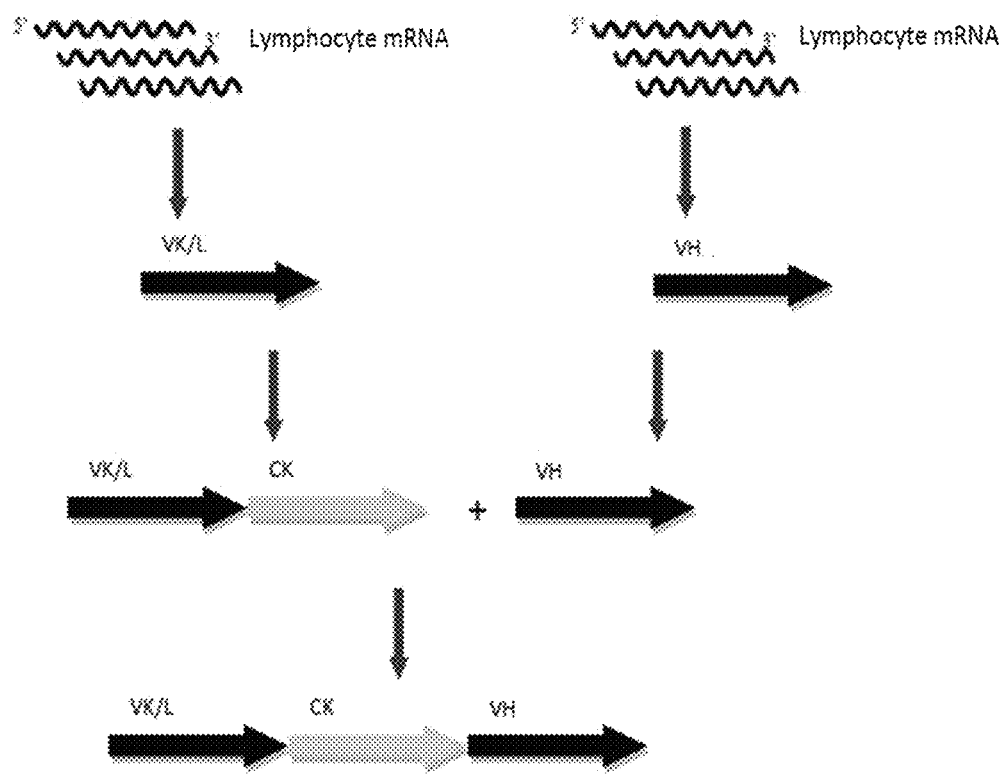
FIG. 7. Synthesis scheme of combinatorial naive human library.
Figure 8:
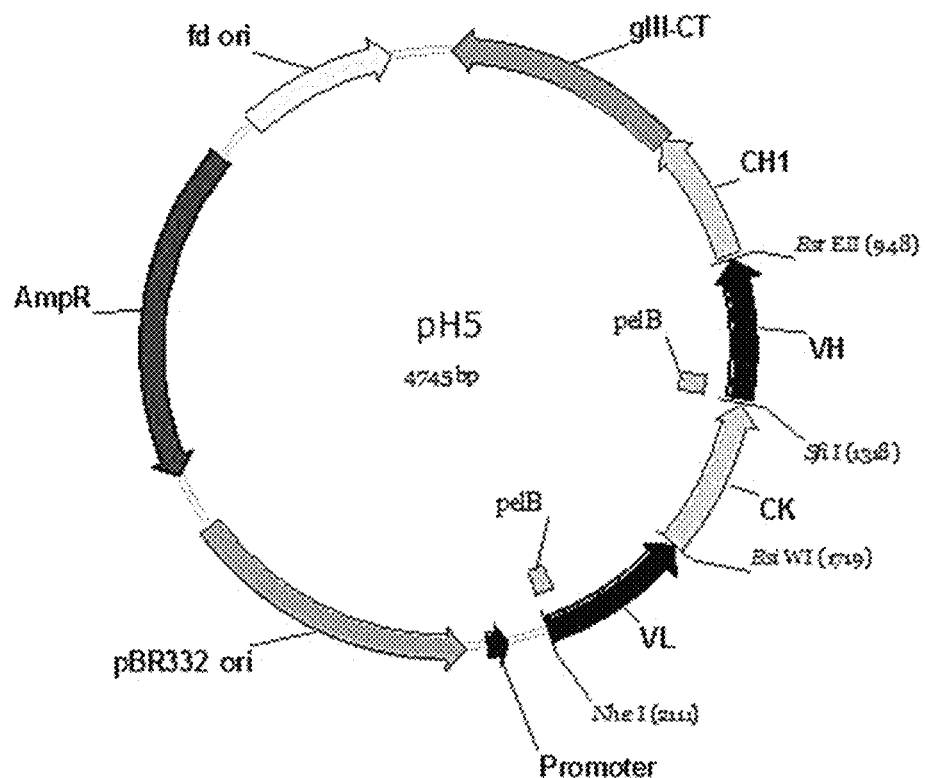
FIG. 8. Phagemid map for cloning Fab phage display libraries.

Cloning was performed by the standard technique. A heavy chain variable domain sequence was cloned into vector pEE-Hc IgG1 at Sal1/Nhe1 restriction sites. A light chain variable domain was cloned into vector pEE-CK at Sal1/BsiW1 restriction sites. Gene constructs obtained were transferred for transient production of proteins in CHO cell line. Proteins were isolated and purified according to standard methods by affinity chromatography on bacterial Protein A as described in example 1. Electrophoresis was performed in denaturing 12% PAGE supplemented with mercaptoethanol and native 8% PAGE (FIG. 6).

Example 11

Determination of Affinity of Full-Length Antibodies on Forte Bio Octert RED 384

Experimental study of binding affinity of antibodies to human IL-5Rα antigen was performed on Forte Bio Octert RED 384. Human IL-5Rα at a concentration of 20 µg/ml was immobilized on the surface of AR2G sensors (ForteBio) according to a standard protocol and manufacturer's instructions. Analysis was conducted at 30° C. using PBS comprising 0.1% Tween 20 and 0.1% BSA as a working buffer. After baseline recording, the sensors were immersed into wells containing antibody solution for 300 seconds, where the complex was associated. Complex dissociation in buffer solution was then detected for 600 seconds.

Figure 11:
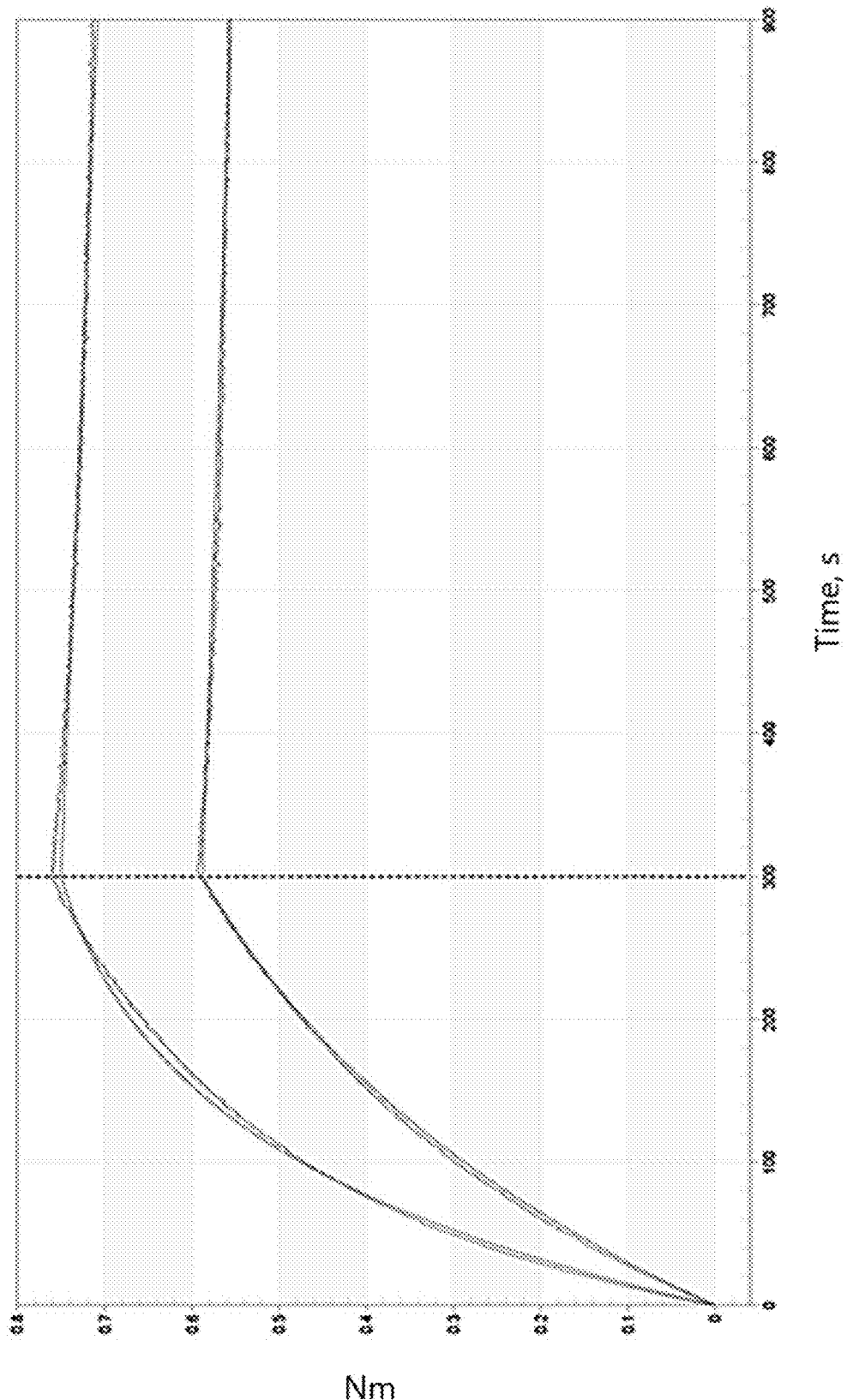
FIG. 11. Sensogram of antibody interaction with IL-5Ra on an Octet RED 384 device (BCD 133-03-002).
Figure 12:
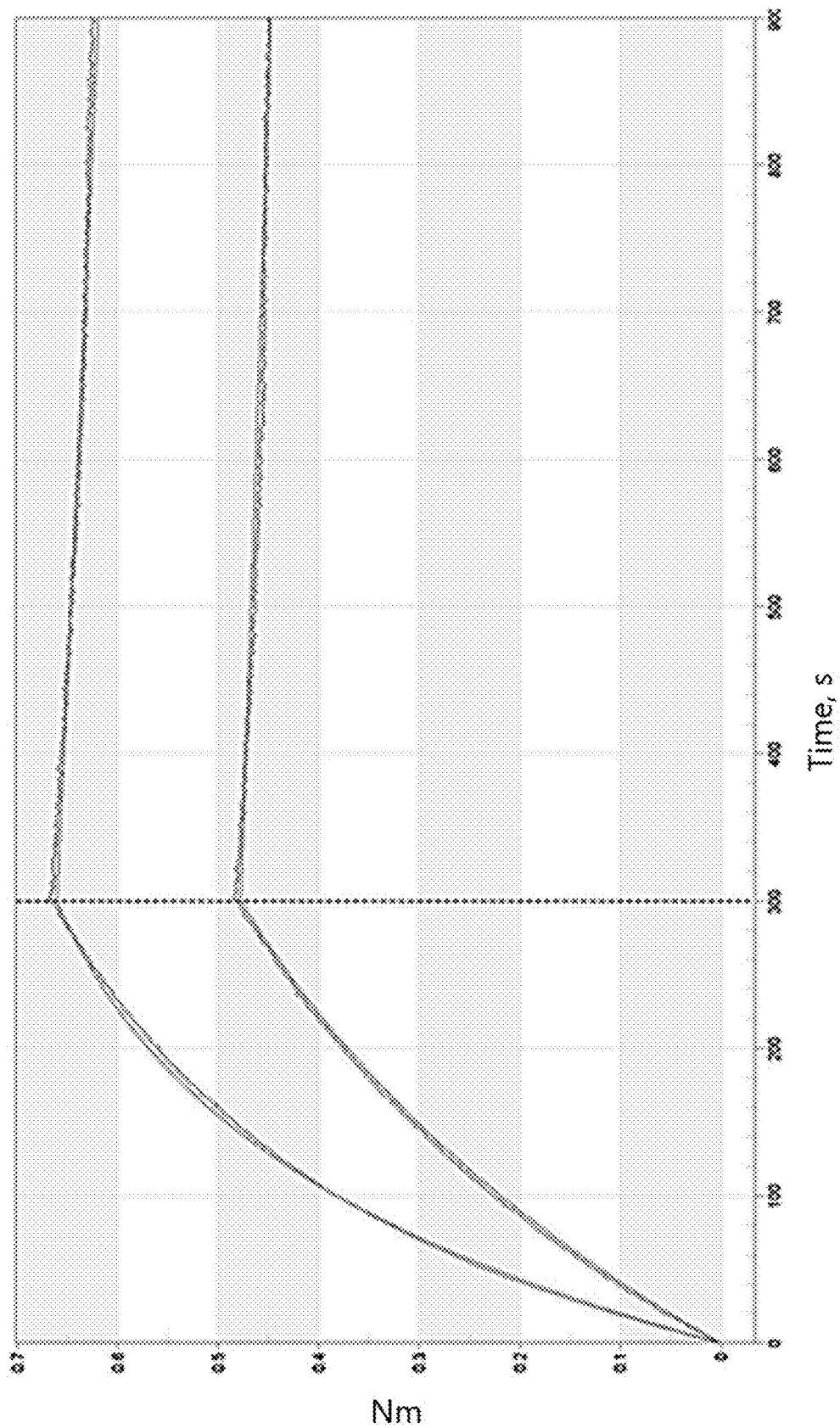
FIG. 12. Sensogram of antibody interaction with IL-5Ra on an Octet RED 384 device (BCD 133-03-020).
Figure 13:
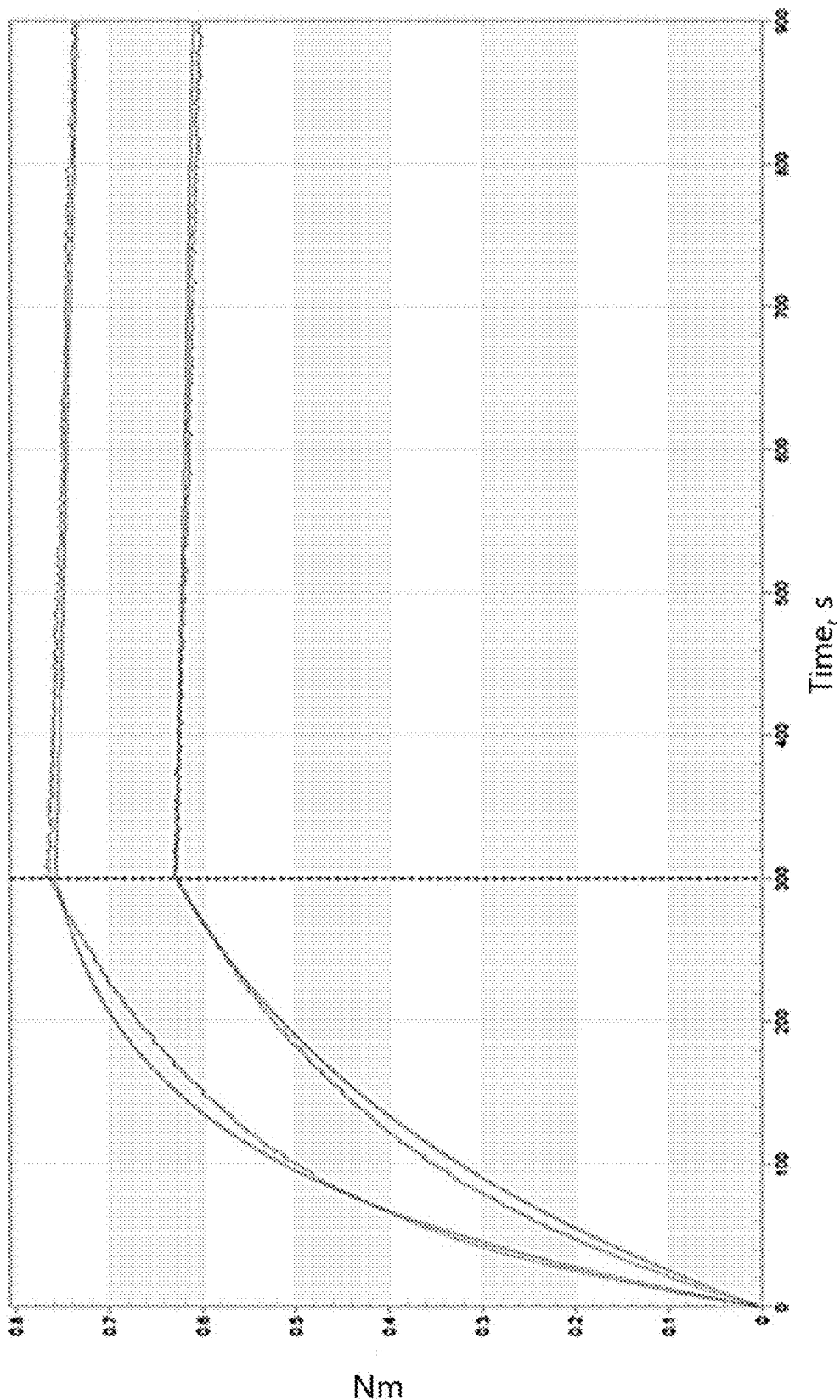
FIG. 13. Sensograms of antibody interaction with IL-5Ra on an Octet RED 384 device (BCD133-03-021).

Binding curves, after subtracting a reference signal, were analyzed using Octet Data Analysis (Version 9.0) software in accordance with the standard procedure and using 1:1 Global interaction model. Anti-IL-5Rα antibodies specifically bind to human antigen with high affinity. Table A (FIG. 11, 12, 13)

TABLE A

BCD-133(03-002, 03-020, 03-021) dissociation constants.

| Name | KD (M) | KD Error |
|---|---|---|
| BCD133-03-002 | 5.27E−10 | 3.94E−12 |
| BCD133-03-020 | 6.67E−10 | 6.03E−12 |
| BCD133-03-021 | 2.24E−11 | 1.29E−12 |

Example 12

Preparation of a Stable Cell Line Expressing IL-5Rα

CHO-K1 cell line was cultured in DMEM/F12 medium with 5% FBS. Transfection of gene construct comprising DNA encoding IL-5Rα was performed using TurboFect according to the manufacturer's protocol.

3 days after transfection, the transfected culture was selected for 14 days by adding hygromycin B to the medium to a final concentration of 250 µg/ml. Cell population obtained after selection was cloned. A cell clone expressing IL-5Rα was selected based on the results of analysis of IL-5R expression level/homogeneity, taking into account growth rate, population homogeneity, and absence of morphological changes.

Example 13

Comparison of Control Reproducible Afucosylated Antibody and Candidate Anti-IL-5Rα Antibodies in ADCC Assay on CHO-IL-5R Cells.

CHO-IL-5R cell line stably expressing IL-5Rα, and spherical blood mononuclear cells (PBMC) of healthy donors were used in ADCC assay. CHO-IL-5R cells were cultured in DMEM/F12 medium comprising 2 mM glutamine, 5% FBS (fetal bovine serum), 0.05 mg/ml gentamicin and 0.4 mg/ml hygromycin B at 37° C. with 5% $CO_2$. Cells were removed from the surface by treatment with trypsin, washed twice in RPMI-1640 with 2 mM glutamine, 10% FBS. Viability and cell number were assessed using a hemocytometer after staining with trypan blue. A suspension of cells at a concentration of $4*10^5$/ml was prepared in RPMI-1640 medium with 10% FBS.

Peripheral blood mononuclear cells (PBMC) were isolated from the venous blood of healthy donors with Ficoll by density gradient separation. Cells were then washed twice in DPBS and resuspended in RPMI-1640 medium with 2 mM glutamine, 10% FBS at a density of $2*10^6$/ml.

A series of 50 µl dilutions of antibodies at concentrations from 0.005 ng/ml to 300 ng/ml were added to the wells of a 96-well plate in order to conduct ADCC assay. 50 µl/well of target cell suspension was then added, the plate was incubated for 30 min at 37° C. and 5% $CO_2$. 50 µl/well of effector cell suspension was added. The plate was incubated for 16 hours at 37° C. with 5% $CO_2$. After incubation, cytotoxicity assay was performed using CytoTox96® Non-Radio Cytotoxicity Assay kit.

ADCC efficacy was calculated using the following formula:

$$ADCC = \frac{\text{Experimental data} - \text{background}}{\text{Complete lysis} - \text{background}} \times 100\%$$

Figure 14:
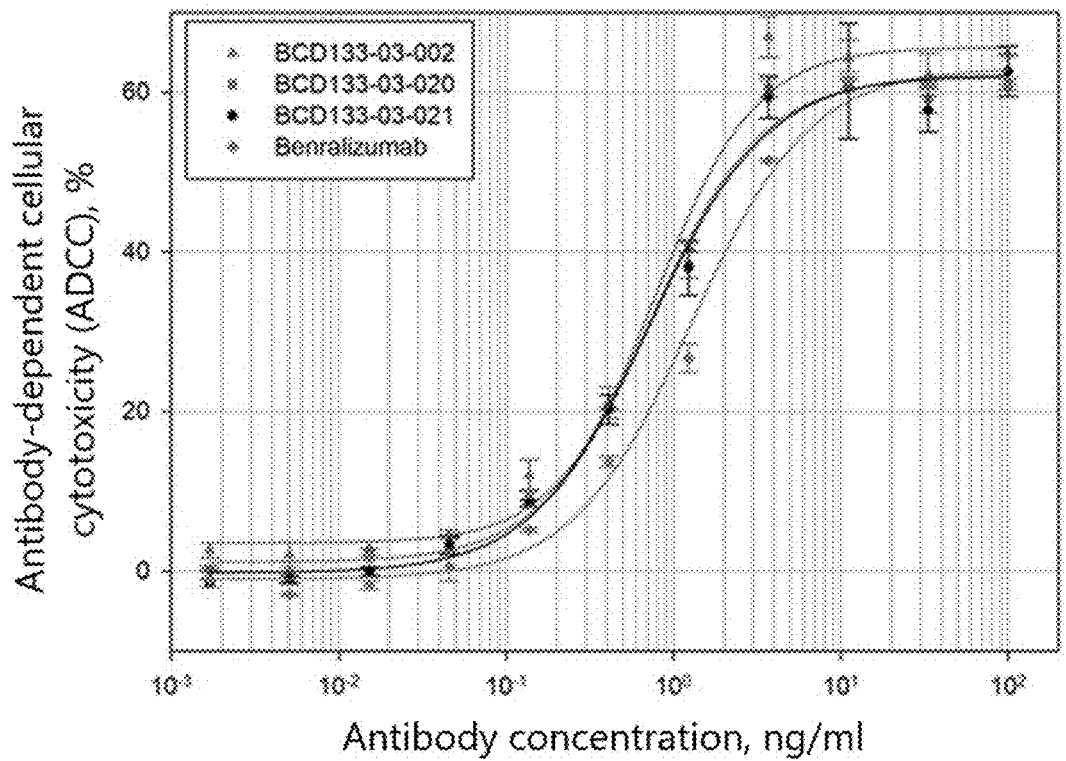
FIG. 14. Dependence of antibody-dependent cellular cytotoxicity on antibody concentration.
Figure 15:
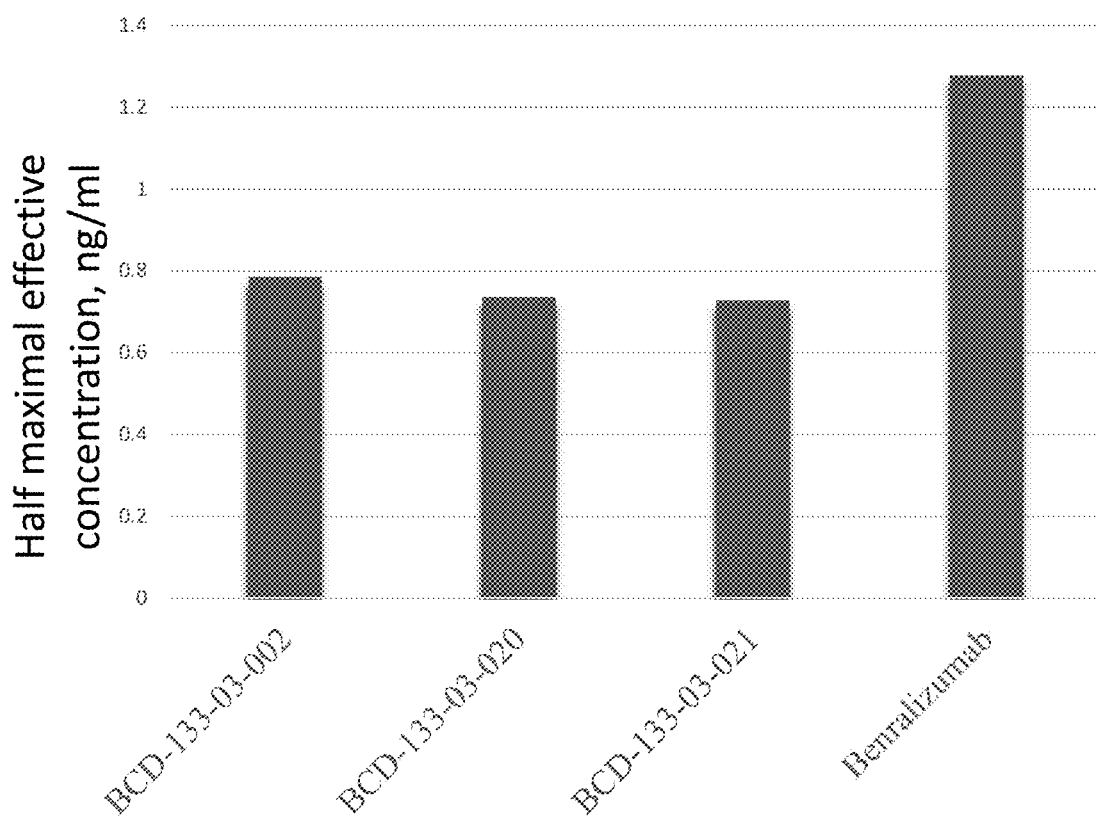
FIG. 15. The values of the half-maximal effective concentration (EC50) in the comparative analysis with the antibody Benralizumab.

Half maximal effective concentration (EC50) was calculated using GraphPad Prism 6.0. According to the experiment, efficacy of candidate anti-IL-5Rα antibodies BCD-133-03-002, BCD-133-03-020, BCD-133-03-021 is 1.6 times higher than that of antibody Benralizumab (BCD-133-018-200617). Candidates do not show significant difference in efficacy against each other in relation to Benralizumab. Results are shown in FIG. 14,15.

Example 14

Analysis of Interactions with Cynomolgus Monkey/Rabbit/Mouse IL-5Rα Receptors on Forte Bio Octet RED 384

Experimental study of binding affinity of antibodies to animal IL-5Rα antigen was performed on Forte Bio Octert RED 384. Antibodies at a concentration of 20 µg/ml were immobilized on the surface of AR2G sensors (Forte Bio) according to a standard protocol and manufacturer's instructions. Analysis was conducted at 30° C. using PBS comprising 0.1% Tween 20 and 0.1% BSA as a working buffer. After baseline recording, the sensors were immersed into wells containing antigen solution (animal IL-5Rα) for 300 seconds, where the complex was associated. Complex dissociation in buffer solution was then detected for 600 seconds.

Figure 16:
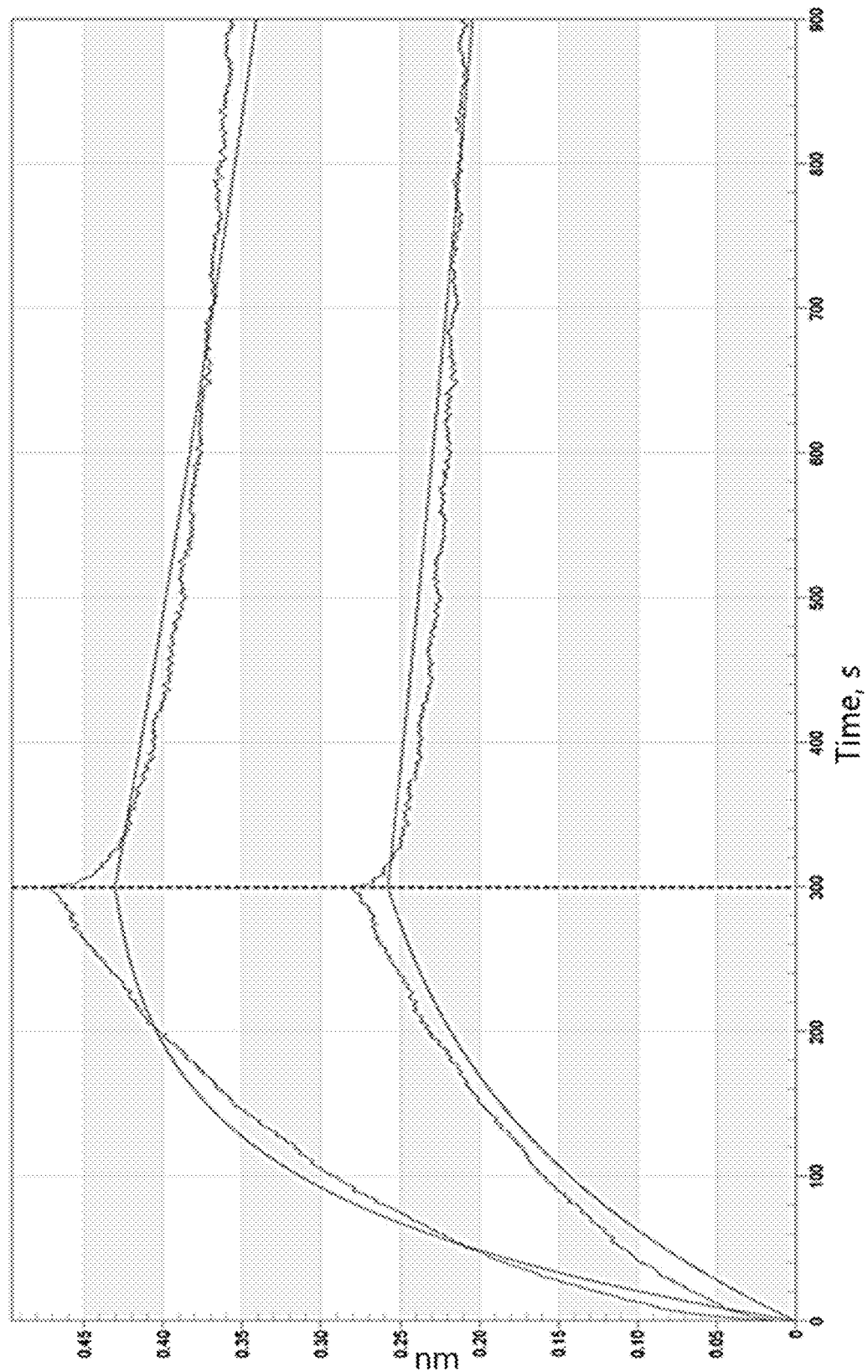
FIG. 16. Sensogram of antibody interaction with macaque IL-5Ra using an Octet RED 384 device (BCD133-03-002).
Figure 17:
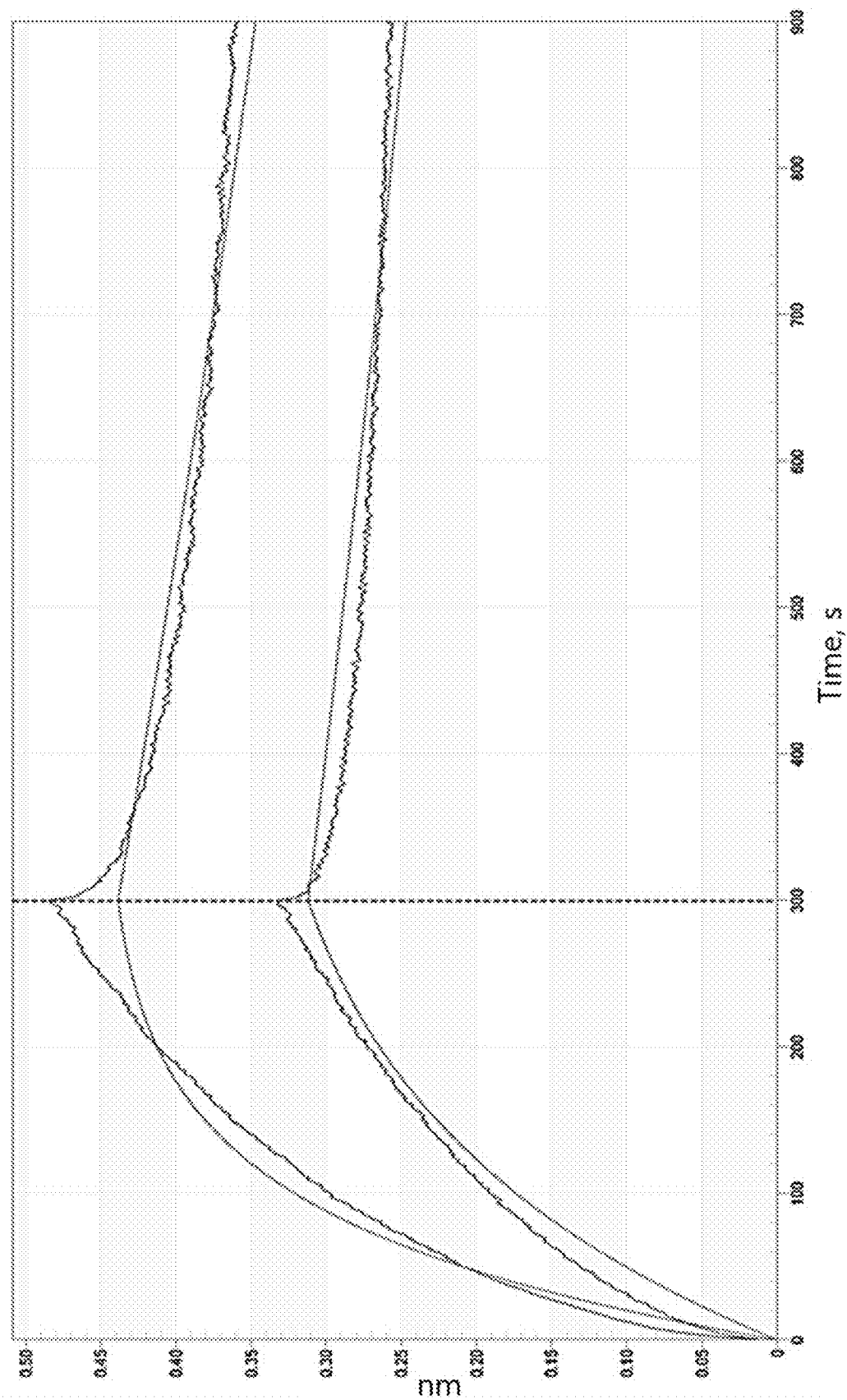
FIG. 17. Sensogram of antibody interaction with macaque IL-5Ra on an Octet RED 384 device (BCD133-03-020).
Figure 18:
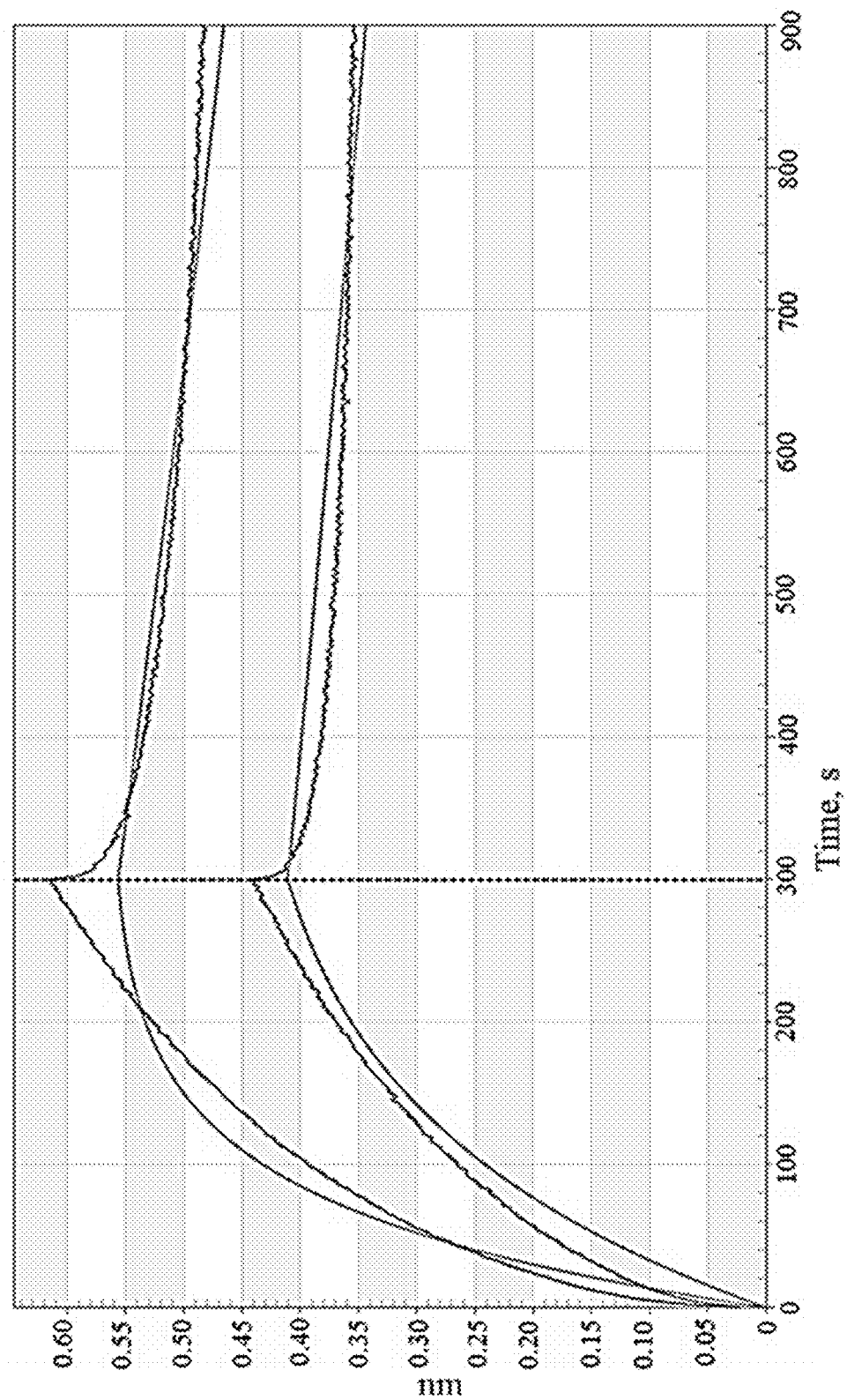
FIG. 18. Sensogram of antibody interaction with macaque IL-5Ra on an Octet RED 384 device (BCD133-03-021).
Figure 19:
FIG. 19. 3D spatial model of the BCD-133 and IL-5Ra complex.
Figure 20:
FIG. 20. 3D spatial model of the BCD-133 and IL-5Ra complex.

Binding curves, after subtracting a reference signal, were analyzed using Octet Data Analysis (Version 9.0) software in accordance with the standard procedure and using 1:1 Global interaction model. Anti-IL-5Rα antibodies specifically bind to cynomolgus monkey antigen. Table B. FIG. 16,17,18.

TABLE B

Table shows dissociation constants of antibodies against cynomolgus monkey antigen (IL-5Rα).

| Name | KD (M) | KD Error |
|---|---|---|
| BCD133-03-002 | 5.53E−09 | 1.21E−10 |
| BCD133-03-020 | 1.22E−08 | 2.30E−10 |
| BCD133-03-021 | 1.68E−08 | 4.55E−10 |

Antibodies do not interact with mouse and rabbit IL-5Rα.

Example 15

Generation of a Stable Cell Line, Production and Purification of Anti-IL-5R Antibody A stable cell line producing monoclonal antibody BCD-133 was obtained by transfecting with electroporation using 4D Nucleofector (Lonza) the parental suspension CHO-K1-S cell line with vector constructs that comprised the optimum ratio of light and heavy antibody chains. High level clonal lineages (over 1000 mg/l) were obtained using ClonePix robotic platform (Molecular Devices) and preliminary minipool selection steps using antibiotics in different cultivation formats. Quantitative analysis was performed using the Octet QK System (Pall Life Sciences) analytical system. Base medium and culture scheme were selected on an automated system Tecan Genesis Workstation RSP 200/8 Automatic Liquid Handling System (Tecan) followed by mathematical processing in MODDE software. Producer was cultured using serum-free media and feedings which do not contain animal-derived protein. BCD-133 for preclinical studies was prepared in HyClone single-use bioreactor (Thermo Fisher Scientific) 50 L fermenter.

Culture fluid was clarified on Millistak COHC (Merck-Millipore) depth filter. Primary purification of the antibody from the clarified culture medium was performed on Protein A affinity sorbent. Target protein was specifically eluted with glycine buffer pH 3.3-3.8 under acidic conditions. Collected eluate was exposed to acidic pH for 30-60 min for the purpose of viral inactivation, and then neutralized with 1M Tris-OH solution to pH 6.5-7.0. Final chromatographic purification to remove residual DNA, producer cell proteins, released affine sorbent's ligand, aggregates and antibody fragments was performed using CaptoAdhere sorbent (GE HealthCare LifeSciences) in a flow-through mode. To this end, protein solution was flowed through prepared sorbent at pH 6.5-7.0, under low conductivity (<3 msec/cm2). Purified protein was then subject to virus-removing filtration using Viresolve PRO filter kit (Millipore), concentrating and diafiltration against the final buffer containing acetate buffer (pH 5.0-5.5) and trehalose. Protein concentration was 50 mg/ml and higher.

Example 16

In Silico Modeling of Antibody BCD-133/Human IL-5Rα Complex

To create mutant antibodies BCD-133 specific against IL-5Rα, 3D structural analysis was performed using Schrodinger Suite version 2017-1 (Schrodinger) software. A structure deposited in Protein Data Bank under the ID code: 3VA2 was selected as a target crystal structure. Docking was performed using PIPER tool from Schrodinger Suite software. The selection of optimal positions was carried out using the free energy estimate (MM-GBSA method) at the 25 nanosecond molecular dynamics interval (Desmond instrument by D.E. Shaw Research). The structure obtained was visualized using Maestro (Schrodinger) tool. FIG. 19,20 show a model which includes variable domains of BCD-133

TABLE C

The middle column shows amino acid residues of antibody BCD-133, which form interaction with human IL-5Rα. The right hand side column shows the corresponding amino acid residues of IL-5Rα antigen, which interact with antibody BCD-133.

| | Positions involved in interaction with human IL-5Ra | Human IL-5Ra positions involved in interaction with BCD-133 |
|---|---|---|
| VH BCD-133 | Lys55 | Asn104 |
| | Ser56 | Gln103 |
| | | Leu108 |
| | Thr57 | His106 |
| | | Ser107 |
| | Thr97 | Asp76 |
| | Asn98 | |
| | Val100A | |
| | Tyr99 | Glu74 |
| | | Asn70 |

TABLE C-continued

The middle column shows amino acid residues of antibody BCD-133, which form interaction with human IL-5Rα. The right hand side column shows the corresponding amino acid residues of IL-5Rα antigen, which interact with antibody BCD-133.

| | Positions involved in interaction with human IL-5Ra | Human IL-5Ra positions involved in interaction with BCD-133 |
|---|---|---|
| | Gly100 | Lys68 |
| | Tyr99 | Ile69 |
| VL | Ser95A | Leu108 |
| BCD-133 | | |
| | Gly95B | |
| | Ser95A | Ser107 |
| | Asp50 | Glu74 |
| | Asp32 | Lys68 |
| | Ser30B | Ser112 |
| | Tyr31 | |
| | Ser30B | Trp113 |
| | Gly30C | |
| | Tyr31 | Arg99 |
| | Tyr91 | |
| | Tyr31 | Ser111 |
| | Tyr91 | Ala110 |
| | Ser93 | Ala110 |
| | Ser95A | Leu109 |

Example 17

Construction of Library of Mutant Antibodies BCD-133 Specific for Human IL-5Rα

To create mutant antibodies BCD-133 specific for IL-5Rα, 3D structural analysis was performed using Schrodinger Suite version 2017-1 (Schrodinger) software and IL-5Rα model (PDB 3VA2) (see also Example 16). Based on a computational model, a set of 3D structures of antibody/IL-5Rα complex was created, each 3D structure containing no more than 6 amino acid substitutions for modifying antibody affinity and complex stability. In the next step, the resulting set of structures formed a library, including variants in which the substitutions resulted in increased complex stability and increased antibody affinity.

In the table below, CDRs were determined using Chothia Canonical Assignment, and not using the more common Kabat classification, as indicated by CDRs comprising sequences of SEQ ID NOs: 1-3, 6-8, this clustering algorithm defines loops on antibody structure better as compared to other variants. Therefore, said clustering method, namely, was used for modifying antibody affinity.

An antibody library obtained according to the above protocol includes 71 antibody sequences. 16 positions were substituted. 9 of 16 are light chain CDR regions, and the other 7 positions are heavy chain CDR regions. The number of unique substitutions is 60. Table D shows CDR sequences of original candidate loops, as well as a set of amino acid substitutions shown by each of the 71 mutant sequences. Sequences of mutant CDR loops from the library can be summarized as follows:

TABLE D

Sequences of original candidate/substitution CDR loops

| | H1 | H2 | H3 | L1 | L2 | L3 |
|---|---|---|---|---|---|---|
| Initial sequence | GFTFSNY | NSGGKS | YATNYGVPYFGS | SGSRSNIGSGYDVH | DDNNRPS | QSYDSSLSGHVV |
| Mutant1 | ------- | -L-T-- | --R-------L- | I------------- | ------- | ----W------- |
| Mutant2 | ------- | -W---- | ----------H- | --E----------- | ---H--- | ----HY------ |
| Mutant3 | ------- | -W---- | ----------H- | --C----------- | ---H--- | ----LY------ |
| Mutant4 | ------- | -W---- | ----------H- | --H----------- | ---H--- | ----LY------ |
| Mutant5 | ------- | -W---- | ----------H- | --L----------- | ---H--- | ----LY------ |
| Mutant6 | ------- | -W---- | ----------H- | --E----------- | ---H--- | ----NY------ |
| Mutant7 | ------- | -W-T-- | --R-------L- | W------------- | ------- | ----E------- |
| Mutant8 | ------- | -W-T-- | --R-------L- | R------------- | ------- | ----E------- |
| Mutant9 | ------- | -F---- | ----------H- | --E----------- | ---H--- | ----LY------ |
| Mutant10 | ------- | -W---- | ----------H- | --E----------- | ---H--- | ----FY------ |
| Mutant11 | ------- | -W---- | ----------H- | --E----------- | ---H--- | ----EY------ |
| Mutant12 | ------- | -W-T-- | --L-------L- | W------------- | ------- | ----E------- |
| Mutant13 | ------- | ---H-- | ----------R- | I--IQ--------- | ------- | ------R----- |
| Mutant14 | ------- | -H-T-- | --L---H---L- | W------------- | ------- | ------------ |
| Mutant15 | ----Q-- | --M--- | ----------Y- | W-R----------- | ---R--- | ------------ |
| Mutant16 | ------- | -W---- | ----------H- | --E----------- | ------- | ----LY------ |
| Mutant17 | ------- | -L---- | ----------H- | --E----------- | ---H--- | ----LY------ |
| Mutant18 | ------- | -H---- | ----------H- | --E----------- | ---H--- | ----LY------ |
| Mutant19 | ------- | -MH--- | ----------Y- | F-R----------- | ---R--- | ------------ |
| Mutant20 | ------- | -H-T-- | --L-------L- | W------------- | ------- | ----E------- |
| Mutant21 | ------- | -MH--- | ----------Y- | V-R----------- | ---R--- | ------------ |
| Mutant22 | ------- | -Q---- | ----------H- | --E----------- | ---H--- | ----LY------ |
| Mutant23 | ------- | --H--- | ----------Y- | W-R----------- | ---R--- | ----H------- |
| Mutant24 | ------- | -MQ--- | ----------Y- | V------------- | ---R--- | ------------ |
| Mutant25 | ------- | -MQ--- | ----------Y- | Q------------- | ---R--- | ------------ |
| Mutant26 | ------- | -MQ--- | ------------ | Q-R----------- | ---R--- | ------------ |
| Mutant27 | ------- | -MQ--- | ----------Y- | V-R----------- | ---R--- | ------------ |
| Mutant28 | ------- | --MM-- | ----------Y- | F------------- | ---R--- | ------------ |
| Mutant29 | ------- | -MQ--- | ----------Y- | E-R----------- | ---R--- | ------------ |
| Mutant30 | ----Q-- | --M--- | ----------Y- | H------------- | ---R--- | ------------ |
| Mutant31 | ----Q-- | --H--- | ----------Y- | H-R----------- | ---R--- | ------------ |
| Mutant32 | ------- | -MC--- | ----------Y- | W-R----------- | ---R--- | ------------ |
| Mutant33 | ------- | -MV--- | ----------Y- | F-R----------- | ---R--- | ------------ |
| Mutant34 | ------- | -W-T-- | --R-------L- | I------------- | ------- | ----E------- |
| Mutant35 | ------- | -MQ--- | ----------Y- | Q-R----------- | ---R--- | ------------ |
| Mutant36 | ------- | -MQ--- | ----------Y- | V-R----------- | ---R--- | ------------ |
| Mutant37 | ------- | -MQ--- | ----------Y- | N-R----------- | ---R--- | ------------ |

TABLE D-continued

Sequences of original candidate/substitution CDR loops

| | H1 | H2 | H3 | L1 | L2 | L3 |
|---|---|---|---|---|---|---|
| Mutant38 | ------- | -MS--- | ----------Y- | V-R---------- | ---R--- | ------------ |
| Mutant39 | ------- | -MM--- | ----------Y- | F-R---------- | ---R--- | ------------ |
| Mutant40 | ----Q-- | --I--- | ----------Y- | H-R---------- | ---R--- | ------------ |
| Mutant41 | ------- | --M--- | ----------Y- | H-R---------- | ---R--- | ------------ |
| Mutant42 | ----Q-- | --M--- | ----------Y- | H-R---------- | ---R--- | ------------ |
| Mutant43 | ----Q-- | --L--- | ----------Y- | F-R---------- | ---R--- | ------------ |
| Mutant44 | ----Q-- | --M--- | ----------Y- | F-R---------- | ---R--- | ------------ |
| Mutant45 | ------- | -YH--- | ------------ | W-RI--------- | ------- | ----M------- |
| Mutant46 | ------- | -MQ--- | ----------Y- | H-R---------- | ---R--- | ------------ |
| Mutant47 | ----Q-- | --M--- | ----------Y- | C-R---------- | ---R--- | ------------ |
| Mutant48 | ------- | -ME--- | ----------Y- | W------------ | ---R--- | ------------ |
| Mutant49 | ----Q-- | --M--- | ----------Y- | L-R---------- | ---R--- | ------------ |
| Mutant50 | ------- | -ME--- | ------------ | W-R---------- | ---R--- | ------------ |
| Mutant51 | ------- | --M--- | ----------Y- | F-R---------- | ---R--- | ------------ |
| Mutant52 | ------- | --Q--- | ----------Y- | Q-R---------- | ---R--- | ------------ |
| Mutant53 | ----Q-- | --S--- | ----------Y- | H-R---------- | ---R--- | ------------ |
| Mutant54 | ------- | --Q--- | ----------Y- | V-R---------- | ---R--- | ------------ |
| Mutant55 | ------- | -W---- | ----------H- | --E---------- | ---H--- | ----L------- |
| Mutant56 | ----Q-- | --S--- | ----------Y- | F-R---------- | ---R--- | ------------ |
| Mutant57 | ------- | -ME--- | ----------Y- | Q-R---------- | ---R--- | ------------ |
| Mutant58 | ------- | -ME--- | ----------Y- | V-R---------- | ---R--- | ------------ |
| Mutant59 | ----Q-- | --H--- | ----------Y- | W-R---------- | ---R--- | ------------ |
| Mutant60 | ------- | -F---- | ----------H- | --E---------- | ---H--- | ----HY------ |
| Mutant61 | ------- | --E--- | ----------Y- | W-R---------- | ---R--- | ------------ |
| Mutant62 | ------- | -ME--- | ----------Y- | W-R---------- | ---R--- | ------------ |
| Mutant63 | ------- | --E--- | ----------Y- | Q-R---------- | ---R--- | ------------ |
| Mutant64 | ------- | --E--- | ----------Y- | V-R---------- | ---R--- | ------------ |
| Mutant65 | ------- | --H--- | ----------Y- | M-R---------- | ---R--- | ------------ |
| Mutant66 | ------- | -W---- | ----------H- | --E---------- | ---H--- | ----LY------ |
| Mutant67 | ------- | --H--- | ----------Y- | W-R---------- | ---R--- | ------------ |
| Mutant68 | ------- | --M--- | ----------Y- | F-R-Y-------- | ---R--- | ------------ |
| Mutant69 | ------- | -L-T-- | --R-------L- | I--------L--- | ------- | ------------ |
| Mutant70 | ------- | -W---- | ----------H- | --F---------- | ---H--- | ----LY------ |
| Mutant71 | ------- | -W---- | ----------H- | --N---------- | ---H--- | ----LY------ |

Example 18

Determination of Colloidal Stability by Protein Aggregation Point Using Dynamic Light Scattering

Figure 21:
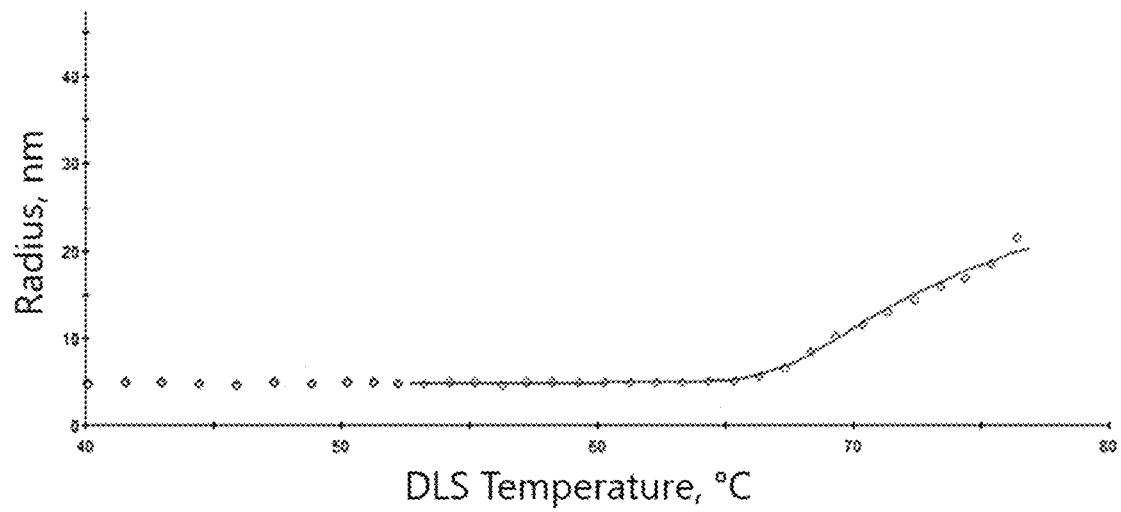
FIG. 21. Graph of average particle size (Z-average) versus temperature.
Figure 22:
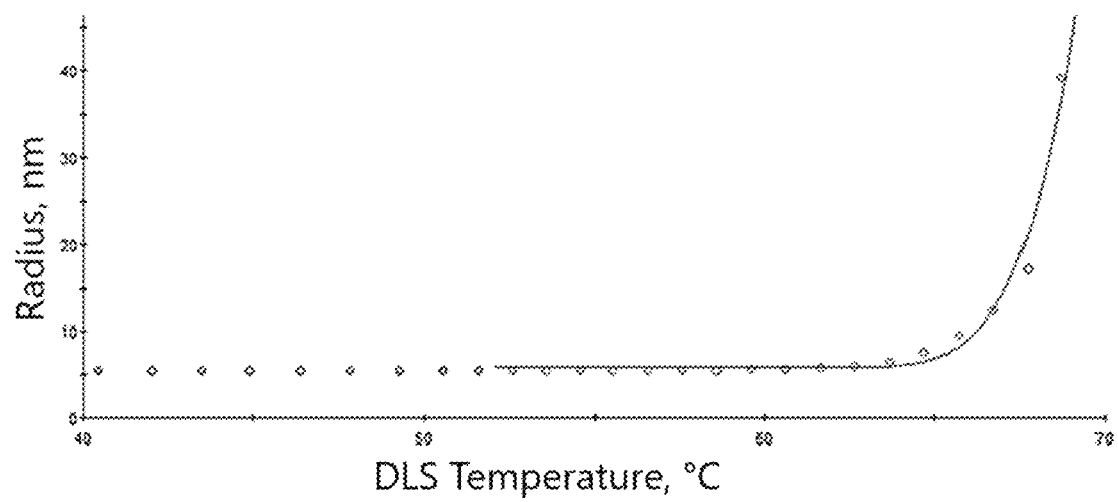
FIG. 22. Graph of average particle size (Z-average) versus temperature.

In order to determine the aggregation temperature of the samples under study by dynamic light scattering, dependence of particle size in the medium on temperature was obtained using DynaPro® Plate Reader II (Wyatt Technology Corp.) with gradual heating from 40 to 85° C. The results are shown in table E. FIG. 21 and FIG. 22 show the profiles of aggregation curves for the antibody under study in 20 mM Acetate, pH=5.0 and 20 mM Citrate, pH=5.0 buffer solutions.

TABLE E

BCD-133 aggregation point

| Test specimens | | Aggregation point |
|---|---|---|
| BCD-133 | 20 mM Acetate, pH = 5.0 | 66.4° C. ± 0.5° C. |
|  | 20 mM Cit, pH = 5.0 | 65.1° C. ± 0.5° C. |

One may conclude that molecule BCD-133 has a high thermo-colloid stability (aggregation point in 20 mM Acetate, pH=5.0 and 20 mM Cit, pH=5.0 buffer solutions is >65).

Example 19

Determination of Thermal Stability Under Thermal Stress at 50° C.

The test samples were placed in a thermostated air bath and thermostated at 50° C. for 72 hours. After heating, intact and stressed samples were analyzed by size-exclusion HPLC (SEC HPLC) with a UV detector and by electrophoresis under non-reducing conditions. Chromatography was performed on Agilent 1100 HPLC system on Tosoh TSK-Gel G3000SWXL column, and detection was performed at a wavelength of 220 nm. Electrophoresis was performed on Caliper Labchip GX II. Preparation of working solutions and preparation of a chip was performed according to standard procedure using HT Protein Express Reagent Kit.

Figure 23:
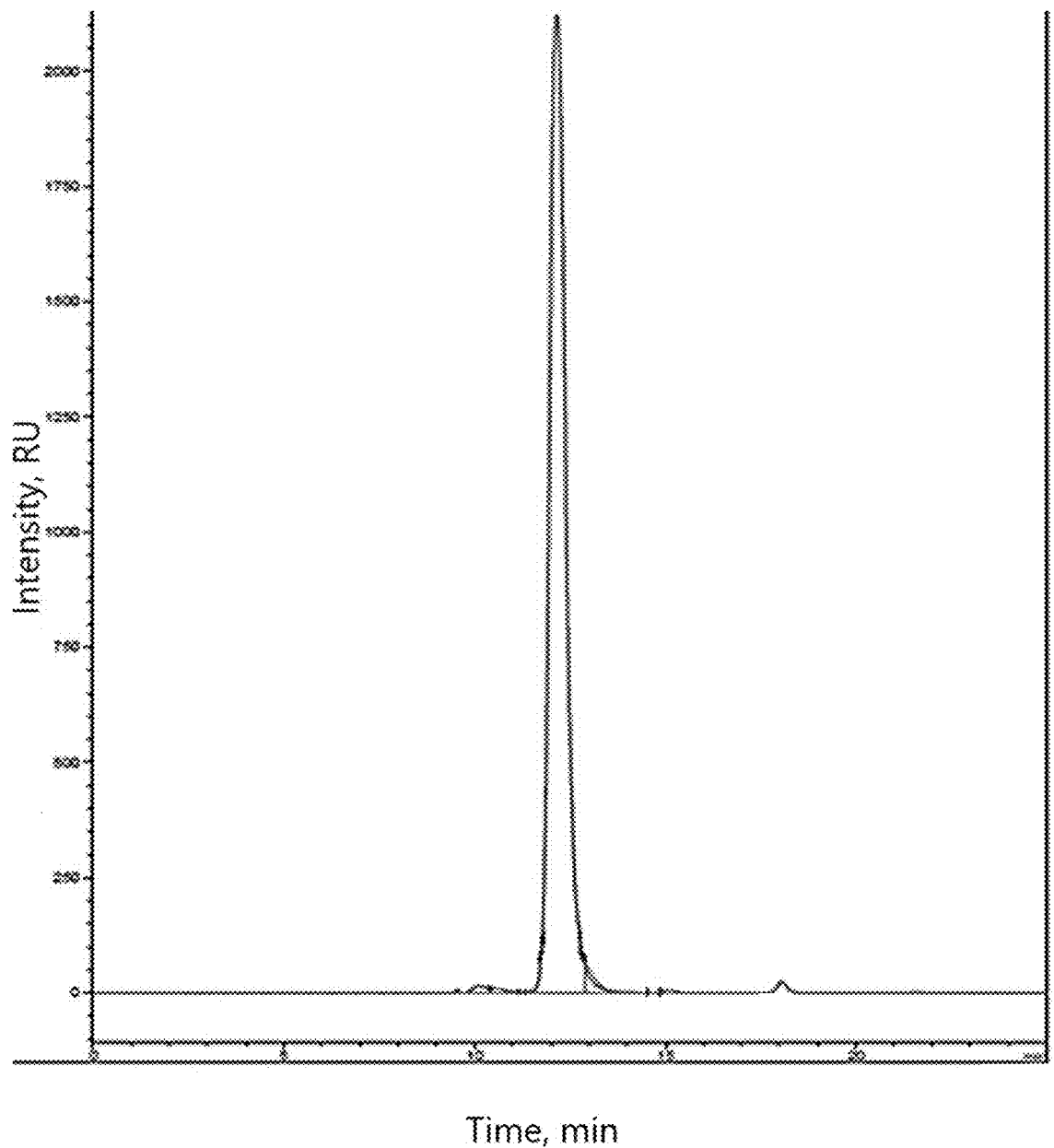
FIG. 23. Combined chromatograms of BCD-133 on a reduced scale. Blue-intact, red—72 hours of incubation at 50° C. in 20 mM Acetate, pH=5.0. The wavelength is 220 nm.
Figure 24:
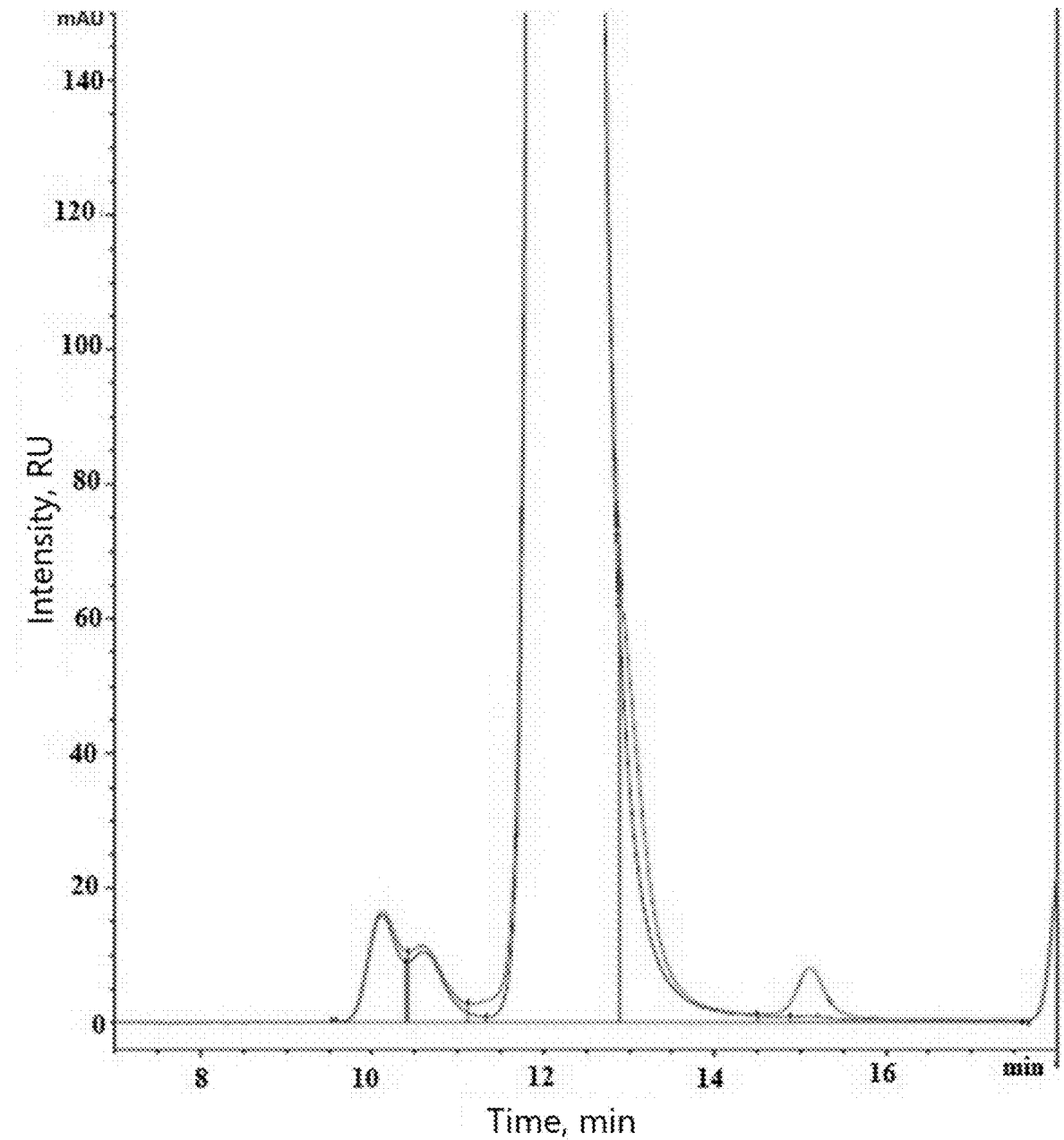
FIG. 24. Combined chromatograms of BCD-133 on an enlarged scale. Blue-intact, red—72 hours of incubation at 50° C. in 20 mM Acetate, rGH=5.0. The wavelength is 220 nm.

Resulting data on stability of BCD-133 when incubated at 50° C. is shown in Table F, FIG. 23, 24 show combined chromatograms: blue—intact; red—72 hour incubation at 50° C.

TABLE F

Dependence of monomer content by size-exclusion HPLC and electrophoresis for BCD-133.

| Buffer solution | specimen conditions | GF HPLC | | | EP |
|---|---|---|---|---|---|
| | | Aggregate content, % | Monomer content, % | Fragment content, % | Main fraction, % |
| 20 mM Acetate, pH = 5.0 | Input control | 1.09 | 97.37 | 1.54 | 88.4 |
| | 72 h at 50° C. | 1.54 | 96.59 | 1.87 | 87.6 |
| | Δ* | 0.45 | −0.78 | 0.33 | −0.8 |
| 20 mM Cit, pH = 5.0 | Input control | 1.429 | 97.281 | 1.289 | 91.3 |
| | 72 h at 50° C. | 1.79 | 96.03 | 2.179 | 89.7 |
| | Δ* | 0.361 | −1.251 | 0.89 | −1.6 |

*Δ is the difference between purity of a stressed sample and purity of an intact sample (input control), %.

---

What is claimed is:

1. A monoclonal antibody or antigen-binding fragment thereof, which specifically binds to IL-5Rα, wherein said monoclonal antibody comprises:
   a heavy chain variable domain comprising HCDR1 comprising the amino acid sequence of SEQ ID NO: 1, HCDR2 comprising the amino acid sequence of SEQ ID NO: 2, and HCDR3 comprising the amino acid sequence of SEQ ID NO: 3; and
   a light chain variable domain comprising LCDR1 comprising the amino acid sequence of SEQ ID NO: 6, LCDR2 comprising the amino acid sequence of SEQ ID NO: 7, and LCDR3 comprising the amino acid sequence of SEQ ID NO: 8.

2. The monoclonal antibody or antigen-binding fragment thereof according to claim 1, wherein the heavy chain variable domain comprises an amino acid sequence that is at least 90% homologous to an amino acid sequence selected from the group consisting of SEQ ID NOs: 4 and 5.

3. The monoclonal antibody or antigen-binding fragment thereof according to claim 1, wherein the heavy chain variable domain comprises an amino acid sequence selected from the group consisting of SEQ ID NOs: 4 and 5.

4. The monoclonal antibody or antigen-binding fragment thereof according to claim 1, wherein the light chain variable domain comprises an amino acid sequence that is at least 90% homologous to an amino acid sequence selected from the group consisting of SEQ ID NOs: 9 and 10.

5. The monoclonal antibody or antigen-binding fragment thereof according to claim 1, wherein the light chain variable domain comprises an amino acid sequence selected from the group consisting of SEQ ID NOs: 9 and 10.

6. A monoclonal antibody or antigen-binding fragment thereof according to claim 1, wherein
   a) the heavy chain variable domain comprises an amino acid sequence selected from the group consisting of SEQ ID NOs: 4 and 5; and
   b) the light chain variable domain comprises an amino acid sequence selected from the group consisting of SEQ ID NOs: 9 and 10.

7. A monoclonal antibody according to claim 1, which comprises:
   a) a heavy chain comprising an amino acid sequence that is at least 90% homologous to a sequence selected from the group consisting of SEQ ID NOs: 11 and 12; and
   b) a light chain comprising an amino acid sequence that is at least 90% homologous to a sequence selected from the group consisting of SEQ ID NOs: 13 and 14.

8. A monoclonal antibody according to claim 1, which comprises:
   a) a heavy chain comprising an amino acid sequence selected from the group consisting of SEQ ID NOs: 11 and 12; and
   b) a light chain comprising an amino acid sequence selected from the group consisting of SEQ ID NOs: 13 and 14.

9. A monoclonal antibody according to claim 1, wherein the IL-5Rα-specific antibody is a full IgG antibody.

10. A monoclonal antibody according to claim 9, wherein the full IgG antibody is of human IgG1, IgG2, IgG3 or IgG4 isotype.

11. A nucleic acid encoding an antibody or antigen-binding fragment thereof according to claim 1.

12. The nucleic acid according to claim 11, wherein the nucleic acid is DNA.

13. A nucleic acid which comprises:
   a) a nucleotide sequence encoding the heavy chain of an antibody according to claim 1 and being at least 90% homologous to a sequence selected from the group consisting of SEQ ID NOs: 15 and 16, and/or a nucleotide sequence encoding the light chain of an antibody according to claim 1 and being at least 90% homologous to a sequence selected from the group consisting of SEQ ID NOs: 17 and 18; or
  b) a nucleotide sequence selected from the group consisting of SEQ ID NOs: 15 and 16, said nucleotide sequence encoding the heavy chain of an antibody according to claim 1, and/or a nucleotide sequence selected from the group consisting of SEQ ID NOs: 17 and 18, said nucleotide sequence encoding the light chain of an antibody according to claim 1.

14. An expression vector comprising a nucleic acid according to claim 11.

15. A method for producing a host cell for preparing an antibody or antigen-binding fragment thereof according to claim 1, which comprises transformation of a cell with an expression vector comprising a nucleic acid encoding the antibody or antigen-binding fragment thereof.

16. A host cell comprising a nucleic acid encoding the antibody or antigen-binding fragment thereof according to claim 1.

17. A method for preparing an antibody or antigen-binding fragment thereof, the method comprising culturing a host cell comprising a nucleic acid encoding the antibody or antigen-binding fragment according to claim 1 in a growth medium under conditions sufficient to produce said antibody and optionally isolating and purifying the obtained antibody or fragment thereof.

18. A pharmaceutical composition for prevention or treatment of a disease or disorder mediated by IL-5Rα, said pharmaceutical composition comprising an antibody or antigen-binding fragment thereof according to claim 1, in combination with one or more pharmaceutically acceptable excipients.

19. The pharmaceutical composition according to claim 18, wherein the disease or disorder mediated by IL-5Rα is selected from the group consisting of: asthma, eosinophilic asthma, severe eosinophilic asthma, atopic asthma; COPD (chronic obstructive pulmonary disease); Churg-Strauss syndrome; eosinophilic esophagitis; and eosinophilic gastroenteritis.

20. A pharmaceutical combination for prevention or treatment of a disease or disorder mediated by IL-5Rα, said pharmaceutical combination comprising an antibody or antigen-binding fragment thereof according to claim 1, and at least one different therapeutically active compound.

21. The pharmaceutical combination according to claim 20, wherein the disease or disorder mediated by IL-5Rα is selected from the group consisting of: eosinophilic asthma, severe eosinophilic asthma, atopic asthma; COPD (chronic obstructive pulmonary disease); Churg-Strauss syndrome; eosinophilic esophagitis; and eosinophilic gastroenteritis.

22. The pharmaceutical combination according to claim 20, wherein the different therapeutically active compound is selected from a small molecule, antibody or steroid hormones.

23. A method for inhibiting the biological activity of IL-5Rα in a subject in need of such inhibition, which comprises administering an effective amount of an antibody or antigen-binding fragment thereof according to claim 1.

24. A method for treatment of a disease or disorder mediated by IL-5Rα, which comprises administering in a subject in need of such treatment an antibody or antigen-binding fragment thereof according to claim 1—in a therapeutically effective amount, wherein the disease or disorder is selected from the consisting of: asthma, eosinophilic asthma, atopic asthma or COPD (chronic obstructive pulmonary disease).

25. The monoclonal antibody or antigen-binding fragment thereof according to claim 1, wherein:
  i)
    1) the heavy chain variable domain comprises an amino acid sequence of SEQ ID NO: 4; and
    2) the light chain variable domain comprises an amino acid sequence of SEQ ID NO: 9;
  ii)
    1) The heavy chain variable domain comprises an amino acid sequence of SEQ ID NO: 5; and
    2) the light chain variable domain comprises an amino acid sequence of SEQ ID NO: 9; or
  iii)
    1) The heavy chain variable domain comprises an amino acid sequence of SEQ ID NO: 5; and
    2) the light chain variable domain comprises an amino acid sequence of SEQ ID NO: 10.

26. The monoclonal antibody or antigen-binding fragment thereof according to claim 1, comprising:
  i)
    1) a heavy chain comprising an amino acid sequence of SEQ ID NO: 11; and
    2) a light chain comprising an amino acid of SEQ ID NO: 13;
  ii)
    1) A heavy chain comprising an amino acid sequence of SEQ ID NO: 12; and
    2) a light chain comprising an amino acid of SEQ ID NO: 13; or
  iii)
    1) a heavy chain comprising an amino acid sequence of SEQ ID NO: 12; and
    2) a light chain comprising an amino acid of SEQ ID NO: 14.

* * * * *

SEQUENCE LISTING

<160> NUMBER OF SEQ ID NOS: 30

<210> SEQ ID NO 1
<211> LENGTH: 5
<212> TYPE: PRT
<213> ORGANISM: Artificial Sequence
<220> FEATURE:
<223> OTHER INFORMATION: Synthesized Sequence

<400> SEQUENCE: 1

Asn Tyr Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthesized Sequence

<400> SEQUENCE: 2

Ala Ile Asn Ser Gly Gly Lys Ser Thr Asn Tyr Ala Asp Ser Val Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Synthesized Sequence

<400> SEQUENCE: 3

Asp Tyr Ala Thr Asn Tyr Gly Val Pro Tyr Phe Gly Ser
1               5                   10

<210> SEQ ID NO 4
<211> LENGTH: 121
<212> TYPE: PRT
<213> ORGANISM: Artificial Sequence
<220> FEATURE:
<223> OTHER INFORMATION: Synthesized Sequence

<400> SEQUENCE: 4

Gln Val Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Asn Ser Gly Gly Lys Ser Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asp Tyr Ala Thr Asn Tyr Gly Val Pro Tyr Phe Gly Ser Trp Gly
            100                 105                 110

Gln Gly Thr Thr Val Thr Val Ser Ser
        115                 120

<210> SEQ ID NO 5
<211> LENGTH: 121
<212> TYPE: PRT
<213> ORGANISM: Artificial Sequence
<220> FEATURE:
<223> OTHER INFORMATION: Synthesized Sequence

<400> SEQUENCE: 5

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Asn Ser Gly Gly Lys Ser Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asp Tyr Ala Thr Asn Tyr Gly Val Pro Tyr Phe Gly Ser Trp Gly
            100                 105                 110

Gln Gly Thr Met Val Thr Val Ser Ser
        115                 120

<210> SEQ ID NO 6
<211> LENGTH: 14
<212> TYPE: PRT
<213> ORGANISM: Artificial Sequence
<220> FEATURE:
<223> OTHER INFORMATION: Synthesized Sequence

<400> SEQUENCE: 6

Ser Gly Ser Arg Ser Asn Ile Gly Ser Gly Tyr Asp Val His
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 7

Asp Asp Asn Asn Arg Pro Ser
1               5

<210> SEQ ID NO 8
<211> LENGTH: 12
<212> TYPE: PRT
<213> ORGANISM: Artificial Sequence
<220> FEATURE:
<223> OTHER INFORMATION: Synthesized Sequence

<400> SEQUENCE: 8

Gln Ser Tyr Asp Ser Ser Leu Ser Gly His Val Val
1               5                   10

<210> SEQ ID NO 9
<211> LENGTH: 112
<212> TYPE: PRT
<213> ORGANISM: Artificial Sequence
<220> FEATURE:
<223> OTHER INFORMATION: Synthesized Sequence

<400> SEQUENCE: 9

Gln Ala Gly Leu Thr Gln Pro Pro Ser Val Ser Ala Ala Pro Gly Gln
1               5                   10                  15

Arg Val Thr Ile Ser Cys Ser Gly Ser Arg Ser Asn Ile Gly Ser Gly
            20                  25                  30

Tyr Asp Val His Trp Tyr Gln Gln Val Pro Gly Thr Ala Pro Lys Leu
        35                  40                  45

Leu Ile Phe Asp Asp Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly His Val Val Phe Gly Gly Gly Thr Lys Leu Thr Val Leu
            100                 105                 110

<210> SEQ ID NO 10
<211> LENGTH: 112
<212> TYPE: PRT
<213> ORGANISM: Artificial Sequence
<220> FEATURE:

<223> OTHER INFORMATION: Synthesized Sequence

<400> SEQUENCE: 10

Gln Ser Val Leu Thr Gln Pro Pro Ser Val Ser Ala Ala Pro Gly Gln
1               5                   10                  15

Arg Val Thr Ile Ser Cys Ser Gly Ser Arg Ser Asn Ile Gly Ser Gly
            20                  25                  30

Tyr Asp Val His Trp Tyr Gln Gln Leu Pro Gly Thr Ala Pro Lys Leu
        35                  40                  45

Leu Ile Tyr Asp Asp Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly His Val Val Phe Gly Gly Gly Thr Lys Leu Thr Val Leu
            100                 105                 110

<210> SEQ ID NO 11
<211> LENGTH: 451
<212> TYPE: PRT
<213> ORGANISM: Artificial Sequence
<220> FEATURE:
<223> OTHER INFORMATION: Synthesized Sequence

<400> SEQUENCE: 11

Gln Val Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Asn Ser Gly Gly Lys Ser Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asp Tyr Ala Thr Asn Tyr Gly Val Pro Tyr Phe Gly Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

```
Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 12
<211> LENGTH: 451
<212> TYPE: PRT
<213> ORGANISM: Artificial Sequence
<220> FEATURE:
<223> OTHER INFORMATION: Synthesized Sequence

<400> SEQUENCE: 12

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
            35                  40                  45

Ser Ala Ile Asn Ser Gly Gly Lys Ser Thr Asn Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asp Tyr Ala Thr Asn Tyr Gly Val Pro Tyr Phe Gly Ser Trp Gly
            100                 105                 110

Gln Gly Thr Met Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Thr Val
        180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 13
<211> LENGTH: 219
<212> TYPE: PRT
<213> ORGANISM: Artificial Sequence
<220> FEATURE:
<223> OTHER INFORMATION: Synthesized Sequence

<400> SEQUENCE: 13

Gln Ala Gly Leu Thr Gln Pro Pro Ser Val Ser Ala Ala Pro Gly Gln
1               5                   10                  15

Arg Val Thr Ile Ser Cys Ser Gly Ser Arg Ser Asn Ile Gly Ser Gly
            20                  25                  30

Tyr Asp Val His Trp Tyr Gln Gln Val Pro Gly Thr Ala Pro Lys Leu
        35                  40                  45
```

```
Leu Ile Phe Asp Asp Asn Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly His Val Val Phe Gly Gly Gly Thr Lys Leu Thr Val Leu
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 14
<211> LENGTH: 219
<212> TYPE: PRT
<213> ORGANISM: Artificial Sequence
<220> FEATURE:
<223> OTHER INFORMATION: Synthesized Sequence

<400> SEQUENCE: 14

```
Gln Ser Val Leu Thr Gln Pro Pro Ser Val Ser Ala Ala Pro Gly Gln
  1               5                  10                  15

Arg Val Thr Ile Ser Cys Ser Gly Ser Arg Ser Asn Ile Gly Ser Gly
             20                  25                  30

Tyr Asp Val His Trp Tyr Gln Gln Leu Pro Gly Thr Ala Pro Lys Leu
         35                  40                  45

Leu Ile Tyr Asp Asp Asn Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly His Val Val Phe Gly Gly Gly Thr Lys Leu Thr Val Leu
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 15
<211> LENGTH: 1353
<212> TYPE: DNA
<213> ORGANISM: Artificial Sequence
<220> FEATURE:
<223> OTHER INFORMATION: Synthesized Sequence

<400> SEQUENCE: 15
caagtaaccc taaaggaaag tggaggagga cttgtccaac ccggcggcag tttaagactt    60
agctgtgctg cttctggctt tacttttagc aactatgcta tgtcgtgggt gcgtcaagcg   120
ccaggaaagg gcctagaatg ggtgagcgct atcaatagcg gcggaaaaag cactaactac   180
gcggacagcg tgaaaggccg cttcactata agtcgggaca tgctaaaaa cacactgtac   240 ctccagatga actccctaag agctgaggac acggctgtgt actactgcgc tgattatgcg   300
actaactatg gagtgccata cttcggaagc tggggccagg gaacgaccgt aactgtgagt   360
agtgctagca ccaagggccc atcggtcttc cccctggcac cctcctccaa gagcacctct   420
gggggcacag cggccctggg ctgcctggtc aaggactact tccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gagagttgag   660
cccaaatctt gtgacaaaac tcacacatgc ccaccgtgcc cagcacctga actcctgggg   720
ggaccgtcag tcttcctctt ccccccaaaa cccaaggaca cctcatgat ctcccggacc   780 cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgtgtggt cagcgtcctc accgtcctgc accaggactg gctgaatggc   960
aaggagtaca agtgcaaggt ctccaacaaa gccctcccag ccccatcga gaaaaccatc  1020 tccaaagcca agggcagccc cgagaaccag gtgtaca ccctgccccc atcccgggag  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tatagcaagc tcaccgtgga caagagcagg  1260
tggcagcagg ggaacgtctt ctcatgctcc gtgatgcatg aggctctgca caaccactac  1320
acgcagaaaa gcctctccct gtccccgggt aaa                              1353

<210> SEQ ID NO 16
<211> LENGTH: 1353
<212> TYPE: DNA
<213> ORGANISM: Artificial Sequence
<220> FEATURE:
<223> OTHER INFORMATION: Synthesized Sequence

<400> SEQUENCE: 16
caagtacaac tacaggaaag tggaggagga cttgtccaac ccggcggcag tttaagactt    60
agctgtgctg cttctggctt tacttttagc aactatgcta tgtcgtgggt gcgtcaagcg   120
ccaggaaagg gcctagaatg ggtgagcgct atcaatagcg gcggaaaaag cactaactac   180

| | |
|---|---|
| gcggacagcg tgaaaggccg cttcactata agtcgggaca atgctaaaaa cacactgtac | 240 |
| ctccagatga actccctaag agctgaggac acggctgtgt actactgcgc tgattatgcg | 300 |
| actaactatg gagtgccata cttcggaagc tggggccagg gaacgatggt aactgtgagt | 360 |
| agtgctagca ccaagggccc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gagagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgtgtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tatagcaagc tcaccgtgga caagagcagg | 1260 |
| tggcagcagg ggaacgtctt ctcatgctcc gtgatgcatg aggctctgca caaccactac | 1320 |
| acgcagaaaa gcctctccct gtccccgggt aaa | 1353 |

<210> SEQ ID NO 17
<211> LENGTH: 657
<212> TYPE: DNA
<213> ORGANISM: Artificial Sequence
<220> FEATURE:
<223> OTHER INFORMATION: Synthesized Sequence

<400> SEQUENCE: 17

| | |
|---|---|
| caggctggac tgacgcaacc gccatctgtg agtgcggctc caggacaacg ggtgactata | 60 |
| agctgcagcg gaagcagaag caacataggc agtggatacg acgtacattg gtaccaacaa | 120 |
| gtaccgggga cggctccgaa actactgata tttgacgata taatagacc gagcggcgta | 180 |
| ccagaccgtt ttagcggaag caaaagtgga acgagtgcct ctttagccat aactggcctg | 240 |
| caagctgaag atgaagctga ttattactgt cagagctacg acagcagtct gagtggacac | 300 |
| gtagtgtttg gaggaggaac gaagctgacg gtattacgta cggtggctgc accatctgtc | 360 |
| ttcatcttcc cgccatctga tgagcagttg aaatctggaa ctgcctctgt tgtgtgcctg | 420 |
| ctgaataact cctatcccag agaggccaaa gtacagtgga aggtggataa cgccctccaa | 480 |
| tcgggtaact cccaggagag tgtcacagag caggacagca aggacagcac ctacagcctc | 540 |
| agcagcaccc tgacgctgag caaagcagac tacgagaaac acaaagtcta cgcctgcgaa | 600 |
| gtcacccatc agggcctgag ctcgcccgtc acaaagagct tcaacagggg agagtgt | 657 |

<210> SEQ ID NO 18
<211> LENGTH: 657
<212> TYPE: DNA
<213> ORGANISM: Artificial Sequence
<220> FEATURE:
<223> OTHER INFORMATION: Synthesized Sequence

<400> SEQUENCE: 18

```
cagagtgtgc tgacgcaacc gccatctgtg agtgcggctc caggacaacg ggtgactata      60
agctgcagcg gaagcagaag caacataggc agtggatacg acgtacattg gtaccaacaa     120
ctaccgggga cggctccgaa actactgata tacgacgata ataatagacc gagcggcgta     180
ccagaccgtt ttagcggaag caaaagtgga acgagtgcct ctttagccat aactggcctg     240
caagctgaag atgaagctga ttattactgt cagagctacg acagcagtct gagtggacac     300
gtagtgtttg gaggaggaac gaagctgacg gtattacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt       657
```

<210> SEQ ID NO 19
<211> LENGTH: 121
<212> TYPE: PRT
<213> ORGANISM: Artificial Sequence
<220> FEATURE:
<223> OTHER INFORMATION: Synthesized Sequence

<400> SEQUENCE: 19

```
Gln Val Thr Leu Lys Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Ala Met Ser Trp Val Arg Gln Ala Pro Gly Lys Gly Leu Glu Trp Val
        35                  40                  45
Ser Ala Ile Asn Ser Gly Gly Lys Ser Thr Asn Tyr Ala Asp Ser Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Asp Tyr Ala Thr Asn Tyr Gly Val Pro Tyr Phe Gly Ser Trp Gly
            100                 105                 110
Gln Gly Thr Thr Val Thr Val Ser Ser
        115                 120
```

<210> SEQ ID NO 20
<211> LENGTH: 112
<212> TYPE: PRT
<213> ORGANISM: Artificial Sequence
<220> FEATURE:
<223> OTHER INFORMATION: Synthesized Sequence

<400> SEQUENCE: 20

```
Gln Ala Gly Leu Thr Gln Pro Pro Ser Val Ser Ala Ala Pro Gly Gln
1               5                   10                  15
Arg Val Thr Ile Ser Cys Ser Gly Ser Arg Ser Asn Ile Gly Ser Gly
            20                  25                  30
Tyr Asp Val His Trp Tyr Gln Gln Val Pro Gly Thr Ala Pro Lys Leu
        35                  40                  45
Leu Ile Phe Asp Asp Asn Asn Arg Pro Ser Gly Val Pro Asp Arg Phe
```

```
                     50                  55                  60
Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                     85                  90                  95

Leu Ser Gly His Val Val Phe Gly Gly Gly Thr Lys Leu Thr Val Leu
                100                 105                 110

<210> SEQ ID NO 21
<211> LENGTH: 121
<212> TYPE: PRT
<213> ORGANISM: Artificial Sequence
<220> FEATURE:
<223> OTHER INFORMATION: Synthesized Sequence

<400> SEQUENCE: 21

Gln Val Gln Leu Gln Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Ala Met Ser Trp Val Arg Gln Ala Pro Gly Lys Gly Leu Glu Trp Val
             35                  40                  45

Ser Ala Ile Asn Ser Gly Gly Lys Ser Thr Asn Tyr Ala Asp Ser Val
         50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Asp Tyr Ala Thr Asn Tyr Gly Val Pro Tyr Phe Gly Ser Trp Gly
                100                 105                 110

Gln Gly Thr Met Val Thr Val Ser Ser
            115                 120

<210> SEQ ID NO 22
<211> LENGTH: 112
<212> TYPE: PRT
<213> ORGANISM: Artificial Sequence
<220> FEATURE:
<223> OTHER INFORMATION: Synthesized Sequence

<400> SEQUENCE: 22

Gln Ala Gly Leu Thr Gln Pro Pro Ser Val Ser Ala Ala Pro Gly Gln
  1               5                  10                  15

Arg Val Thr Ile Ser Cys Ser Gly Ser Arg Ser Asn Ile Gly Ser Gly
                 20                  25                  30

Tyr Asp Val His Trp Tyr Gln Gln Val Pro Gly Thr Ala Pro Lys Leu
             35                  40                  45

Leu Ile Phe Asp Asp Asn Asn Arg Pro Ser Gly Val Pro Asp Arg Phe
         50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly His Val Val Phe Gly Gly Gly Thr Lys Leu Thr Val Leu
                100                 105                 110

<210> SEQ ID NO 23
<211> LENGTH: 121
```

```
<212> TYPE: PRT
<213> ORGANISM: Artificial Sequence
<220> FEATURE:
<223> OTHER INFORMATION: Synthesized Sequence

<400> SEQUENCE: 23

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Asn Ser Gly Gly Lys Ser Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asp Tyr Ala Thr Asn Tyr Gly Val Pro Tyr Phe Gly Ser Trp Gly
            100                 105                 110

Gln Gly Thr Met Val Thr Val Ser Ser
        115                 120

<210> SEQ ID NO 24
<211> LENGTH: 112
<212> TYPE: PRT
<213> ORGANISM: Artificial Sequence
<220> FEATURE:
<223> OTHER INFORMATION: Synthesized Sequence

<400> SEQUENCE: 24

Gln Ser Val Leu Thr Gln Pro Pro Ser Val Ser Ala Ala Pro Gly Gln
1               5                   10                  15

Arg Val Thr Ile Ser Cys Ser Gly Ser Arg Ser Asn Ile Gly Ser Gly
            20                  25                  30

Tyr Asp Val His Trp Tyr Gln Gln Leu Pro Gly Thr Ala Pro Lys Leu
        35                  40                  45

Leu Ile Tyr Asp Asp Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly His Val Val Phe Gly Gly Gly Thr Lys Leu Thr Val Leu
            100                 105                 110

<210> SEQ ID NO 25
<211> LENGTH: 451
<212> TYPE: PRT
<213> ORGANISM: Artificial Sequence
<220> FEATURE:
<223> OTHER INFORMATION: Synthesized Sequence

<400> SEQUENCE: 25

Gln Val Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
```

```
            35                  40                  45
Ser Ala Ile Asn Ser Gly Gly Lys Ser Thr Asn Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Asp Tyr Ala Thr Asn Tyr Gly Val Pro Tyr Phe Gly Ser Trp Gly
                100                 105                 110

Gln Gly Thr Thr Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
450
```

<210> SEQ ID NO 26
<211> LENGTH: 219
<212> TYPE: PRT
<213> ORGANISM: Artificial Sequence
<220> FEATURE:
<223> OTHER INFORMATION: Synthesized Sequence

<400> SEQUENCE: 26

```
Gln Ala Gly Leu Thr Gln Pro Pro Ser Val Ser Ala Ala Pro Gly Gln
1               5                   10                  15

Arg Val Thr Ile Ser Cys Ser Gly Ser Arg Ser Asn Ile Gly Ser Gly
            20                  25                  30

Tyr Asp Val His Trp Tyr Gln Gln Val Pro Gly Thr Ala Pro Lys Leu
        35                  40                  45

Leu Ile Phe Asp Asp Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly His Val Val Phe Gly Gly Gly Thr Lys Leu Thr Val Leu
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 27
<211> LENGTH: 451
<212> TYPE: PRT
<213> ORGANISM: Artificial Sequence
<220> FEATURE:
<223> OTHER INFORMATION: Synthesized Sequence

<400> SEQUENCE: 27

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Asn Ser Gly Gly Lys Ser Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
```

```
                85                  90                  95
Ala Asp Tyr Ala Thr Asn Tyr Gly Val Pro Tyr Phe Gly Ser Trp Gly
            100                 105                 110

Gln Gly Thr Met Val Thr Val Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 28
<211> LENGTH: 219
<212> TYPE: PRT
<213> ORGANISM: Artificial Sequence
<220> FEATURE:
<223> OTHER INFORMATION: Synthesized Sequence
```

<400> SEQUENCE: 28

```
Gln Ala Gly Leu Thr Gln Pro Pro Ser Val Ser Ala Ala Pro Gly Gln
1               5                   10                  15

Arg Val Thr Ile Ser Cys Ser Gly Ser Arg Ser Asn Ile Gly Ser Gly
            20                  25                  30

Tyr Asp Val His Trp Tyr Gln Gln Val Pro Gly Thr Ala Pro Lys Leu
        35                  40                  45

Leu Ile Phe Asp Asp Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly His Val Val Phe Gly Gly Thr Lys Leu Thr Val Leu
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 29
<211> LENGTH: 451
<212> TYPE: PRT
<213> ORGANISM: Artificial Sequence
<220> FEATURE:
<223> OTHER INFORMATION: Synthesized Sequence

<400> SEQUENCE: 29

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Asn Ser Gly Gly Lys Ser Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asp Tyr Ala Thr Asn Tyr Gly Val Pro Tyr Phe Gly Ser Trp Gly
            100                 105                 110

Gln Gly Thr Met Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
```

```
                130               135               140
Ala Leu Gly Cys Leu Val Lys Asp Tyr Phe Pro Glu Pro Val Thr Val
145                 150               155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                    420                 425                 430

His Glu Ala Leu His Asn His Tyr Thr Gln Lys Ser Leu Ser Leu Ser
                    435                 440                 445

Pro Gly Lys
    450

<210> SEQ ID NO 30
<211> LENGTH: 219
<212> TYPE: PRT
<213> ORGANISM: Artificial Sequence
<220> FEATURE:
<223> OTHER INFORMATION: Synthesized Sequence

<400> SEQUENCE: 30

Gln Ser Val Leu Thr Gln Pro Pro Ser Val Ser Ala Ala Pro Gly Gln
1               5                   10                  15

Arg Val Thr Ile Ser Cys Ser Gly Ser Arg Ser Asn Ile Gly Ser Gly
                20                  25                  30

Tyr Asp Val His Trp Tyr Gln Gln Leu Pro Gly Thr Ala Pro Lys Leu
```

-continued

```
                35                    40                    45
Leu Ile Tyr Asp Asp Asn Asn Arg Pro Ser Gly Val Pro Asp Arg Phe
        50                    55                    60

Ser Gly Ser Lys Ser Gly Thr Ser Ala Ser Leu Ala Ile Thr Gly Leu
65                    70                    75                    80

Gln Ala Glu Asp Glu Ala Asp Tyr Tyr Cys Gln Ser Tyr Asp Ser Ser
                85                    90                    95

Leu Ser Gly His Val Val Phe Gly Gly Gly Thr Lys Leu Thr Val Leu
                100                   105                   110

Arg Thr Val Ala Ala Pro Ser Val Phe Ile Phe Pro Pro Ser Asp Glu
            115                   120                   125

Gln Leu Lys Ser Gly Thr Ala Ser Val Val Cys Leu Leu Asn Asn Phe
            130                   135                   140

Tyr Pro Arg Glu Ala Lys Val Gln Trp Lys Val Asp Asn Ala Leu Gln
145                   150                   155                   160

Ser Gly Asn Ser Gln Glu Ser Val Thr Glu Gln Asp Ser Lys Asp Ser
                165                   170                   175

Thr Tyr Ser Leu Ser Ser Thr Leu Thr Leu Ser Lys Ala Asp Tyr Glu
                180                   185                   190

Lys His Lys Val Tyr Ala Cys Glu Val Thr His Gln Gly Leu Ser Ser
            195                   200                   205

Pro Val Thr Lys Ser Phe Asn Arg Gly Glu Cys
210                   215
```